(12) United States Patent  
Tong

(10) Patent No.: US 9,244,005 B2
(45) Date of Patent: Jan. 26, 2016

(54) ULTRASENSITIVE DETECTION OF ISOTOPES, CHEMICAL SUBSTANCES AND BIOLOGICAL SUBSTANCES USING LASER WAVE MIXING DETECTORS

(75) Inventor: William G. Tong, La Jolla, CA (US)

(73) Assignee: SAN DIEGO STATE UNIVERSITY FOUNDATION, San Diego, CA (US)

( * ) Notice: Subject to any disclaimer, the term of this patent is extended or adjusted under 35 U.S.C. 154(b) by 289 days.

(21) Appl. No.: 13/144,062

(22) PCT Filed: Jan. 11, 2010

(86) PCT No.: PCT/US2010/020682
§ 371 (c)(1),
(2), (4) Date: Jul. 11, 2011

(87) PCT Pub. No.: WO2010/120391
PCT Pub. Date: Oct. 21, 2010

(65) Prior Publication Data
US 2011/0273708 A1   Nov. 10, 2011

Related U.S. Application Data

(60) Provisional application No. 61/143,746, filed on Jan. 9, 2009, provisional application No. 61/147,406, filed on Jan. 26, 2009.

(51) Int. Cl.
*G01B 9/02* (2006.01)
*G01N 21/39* (2006.01)
*G01N 21/19* (2006.01)
*G01N 21/31* (2006.01)
*G01N 21/359* (2014.01)
*G01N 21/3504* (2014.01)
*G01N 21/74* (2006.01)
*G02F 1/35* (2006.01)

(52) U.S. Cl.
CPC .............. *G01N 21/39* (2013.01); *G01N 21/19* (2013.01); *G01N 21/3103* (2013.01); *G01N 21/3504* (2013.01); *G01N 21/359* (2013.01); *G01N 21/74* (2013.01); *G02F 1/3536* (2013.01)

(58) Field of Classification Search
USPC ........................................................ 356/450
See application file for complete search history.

(56) References Cited

U.S. PATENT DOCUMENTS

| | | | |
|---|---|---|---|
| 4,284,354 A | 8/1981 | Liao | |
| 4,355,897 A | 10/1982 | Kaye | |
| 4,540,283 A | 9/1985 | Bachalo | |
| 4,622,642 A | 11/1986 | Bajard et al. | |
| 4,728,165 A * | 3/1988 | Powell et al. | 359/7 |
| 4,854,705 A | 8/1989 | Bachalo | |
| 5,166,507 A | 11/1992 | Davis et al. | |
| 5,262,947 A * | 11/1993 | Boudan et al. | 250/366 |

(Continued)

OTHER PUBLICATIONS

Andrews, J.M., et al., "Atomic flame spectrometry based on polarization-modulated optical phase conjugation by resonant degenerate four-wave mixing," Spectrochimica Acta Part B: Atomic Spectroscopy 44B(1):101-107, 1989.

(Continued)

*Primary Examiner* — Tarifur Chowdhury
*Assistant Examiner* — Omar Nixon
(74) *Attorney, Agent, or Firm* — Perkins Coie LLP

(57) ABSTRACT

Devices and techniques for using four wave mixing in optical sensing of various materials, including isotopes, chemical and biological substances.

14 Claims, 24 Drawing Sheets

(56) References Cited

U.S. PATENT DOCUMENTS

| | | |
|---|---|---|
| 5,600,444 A | 2/1997 | Tong |
| 6,141,094 A | 10/2000 | Tong |
| 6,248,540 B1 | 6/2001 | Weinberg et al. |
| 8,268,551 B2 | 9/2012 | Tong |
| 2001/0033375 A1 | 10/2001 | McFarland et al. |
| 2002/0015150 A1 | 2/2002 | Armstrong et al. |
| 2003/0174324 A1 | 9/2003 | Sandstrom |
| 2006/0263777 A1* | 11/2006 | Tong ............................ 435/6 |
| 2008/0212166 A1* | 9/2008 | Lett et al. ...................... 359/326 |
| 2008/0264792 A1* | 10/2008 | Moon et al. ................... 204/452 |

OTHER PUBLICATIONS

Andrews, J.M., et al., "Doppler-Free Spectrum of the Barium 1S0-1P1 Transition by Degenerate Four-Wave Mixing Using an Air/Acetylene Flame," Applied Spectroscopy, 45(4):697-700, 1991.

Atherton, A.A., et al., "Ultrasensitive absorption detection of protein and DNA microarrays based on nonlinear multi-photon wave-mixing spectroscopy," Proc. SPIE, 5969:59690, Sep. 2005.

Bao, X., et al., "Excited-state optical storage study in a dye-doped film using four-wave mixing spectroscopy," Proc. SPIE, 2998:343-347, Jan. 1997.

Bao, X., et al., "Optical Nonlinearity and Multiplex Holographic Storage in Azo Side-Chain Liquid Crystalline Polymer," Proc. SPIE, 3474:183-189, Oct. 1998.

Berniolles, S., et al., "Diode laser-based nonlinear degenerate four-wave mixing analytical spectrometry," Spectrochimica Acta Part B: Atomic Spectroscopy, 49B(12-14):1473-1481, Oct.-Dec. 1994.

Berniolles, S., et al., "Low-power compact laser-based nonlinear degenerate four-wave mixing detection for flowing liquids," Proc. SPIE, 2546:145-151, Sep. 1995.

Berniolles, S., et al., "Sensitive absorbance measurement for gas-phase analytes based on multiwave mixing spectroscopy," Proc. SPIE, 2835:248-254, Nov. 1996.

Berniolles, S., et al., "Sensitive Capillary-Based On-Column Detection Method by Laser Wave Mixing," Proc. SPIE, 2980:127-132, May 1997.

Berniolles, S., et al., "Sensitive On-Column Absorbance Detection of Native Molecules," Proc. SPIE, 3270:200-206, May 1998.

Briggs, R., et al., "Sub-Doppler high-resolution wave-mixing detection method for isotopes in environmental applications," Proc. SPIE, 5586:54-59, Dec. 2004.

Chen, D.A., et al., "High-resolution Laser Spectroscopy Based on Polarisation-modulated Optical Phase Conjugation in a Demountable Cathode Discharge," J. Anal. Atomic Spectrometry, 3:531-535, Jun. 1988.

International Search Report and Written Opinion dated Oct. 29, 2010 for International Application No. PCT/US2010/020682, filed Jan. 11, 2010 (11 pages).

Kan, H., et al., "Sensitive wave-mixing detectors for capillary electrophoresis and liquid chromatography," Proc. SPIE, 2835:135-142, Nov. 1996.

Knittle, J.E., et al., "Sensitive detection of enzyme activity by multi-photon nonlinear laser spectroscopy," Proc. SPIE, 5587:177-182, Nov. 2004.

Lopez, M.M., et al., "Laser wave-mixing optical method for sensitive detection of analytes in microarrays and microchips," Proc. SPIE, 5591:185-189, Dec. 2004.

Luena, G.A., et al., "Doppler-Free Laser Polarization Spectroscopy Using a Demountable DC Cathode Discharge Cell as a Trace Concentration Atomizer," Applied Spectroscopy, 44(10):1668-1672, Nov. 1990.

Lyons, W., et al., "Nonlinear wave-mixing spectroscopy for sub-Doppler isotope analysis with trace-level detection sensitivity," Proc. SPIE, 5971:597109, Sep. 2005.

Maniaci, M.J., et al., "Multiphoton laser wave-mixing absorption spectroscopy for samarium using a graphite furnace atomizer," Spectrochimica Acta Part B, 59(7):967-973, Jul. 2004.

Mann, B.A., et al., "Detection and imaging of nitrogen dioxide with the degenerate four-wave-mixing and laser-induced-fluorescence techniques," Applied Optics, 35(3):475-481, Jan. 1996.

Mickadeit, F., et al., "Sensitive Sub-Doppler Nonlinear Spectroscopy for Hyperfine Structure Analysis Using Simple Atomizers," Proc. SPIE, 3270:168-173, May 1998.

Mickadeit, F.K., et al., "Sub-Parts-Per-Quadrillion-Level Graphite Furnace Atomic Absorption Spectrophotometry Based on Laser Wave Mixing," Anal. Chem., 76(6):1788-1792, Mar. 2004.

Neyer, D.W., et al., "Circular Dichroism Spectroscopy Using Coherent Laser-Induced Thermal Gratings," J. American Chemical Society, 119(35):8293-8300, 1997.

Nunes, J.A., et al., "Circular Dichroism Spectroscopy by Four-Wave Mixing Using Polarization Grating-Induced Thermal Gratings," J. Phys. Chem. A, 101(18):3279-3283, 1997.

Nunes, J.A., et al., "Optical Fiber-Based Wave Mixing as a Convenient and Sensitive Laser Analytical Tool for Condensed-Phase Analytes," Applied Spectroscopy, 52(5):763-769, 1998.

Nunes, J., et al., "Optical Fiber-Based Wave-Mixing Probe," Proc. SPIE, 2980:429-433, May 1997.

Nunes, J.A., et al., "Sensitive Circular Dichroism Spectroscopy Based on Nonlinear Degenerate Four-Wave Mixing," Anal. Chem., 65(21):2990-2994, Nov. 1993.

Nunes, J.A., et al., "Sensitive laser wave-mixing detection methods for biomedical applications," Proc. SPIE, 2388:205-212, May 1995.

Tong, W.G., et al., "Doppler-Free Spectroscopy Based on Phase Conjugation by Degenerate Four-Wave Mixing in Hollow Cathode Discharge," Applied Spectroscopy, 41(4):586-590, 1987.

Tong, W.G., et al., "Laser Spectrometry Based on Phase Conjugation by Resonant Degenerate Four-Wave Mixing in an Analytical Flame," Anal. Chem., 59(6):896-899, Mar. 1987.

Weed, K.M., et al., "Sensitive sub-Doppler multi wave-mixing spectroscopy for flame and graphite furnace atomizers," Proc. SPIE, 2385:157-164, Apr. 1995.

Weed, K.M., et al., "Trace Analysis of Rubidium Hyperfine Structure in a Flame Atomizer Using Sub-Doppler Laser Wave-Mixing Spectroscopy," Applied Spectroscopy, 57(12):1455-1460, Dec. 2003.

Wu, Z., et al., "Absorbance detection of amino acids by laser wave mixing in microbore liquid chromatography," J. of Chromatography A, 805(1-2):63-69, May 1998.

Wu, Z., et al., "Doppler-free measurement of the calcium 4s2 1S0-4s4p 1p1 transition at 422.673 nm by degenerate four-wave mixing in a demountavle cathode discharge atomizer," Spectrochimica Acta Part B, 47B(3):449-457, Mar. 1992.

Wu, Z., et al., "Forward-Scattering Degenerate Four-Wave Mixing as a Simple Sub-Attomole-Sensitive Nonlinear Laser Analytical Spectrometric Method." Anal. Chem., 65(2):112-117, Jan. 1993.

Wu, Z., et al., "Laser Analytical Spectrometry Based on Optical Phase Conjugation by Degenerate Four-Wave Mixing in a Flowing Liquid Analyte Cell," Anal. Chem., 61(9):998-1001, May 1989.

Wu, Z., et al., "Sensitive absorbance detection method for capillary electrophoresis based on laser wave-mixing," J. of Chromatography A, 773:291-298, 1997.

Wu, Z., et al., "Sensitive absorbance measurement method based on laser multi-wave mixing," Spectrochimica Acta Part B, 49B(12-14):1483-1489, Oct.-Dec. 1994.

Wu, Z., et al., "Stable Isotope Ratio Analysis at Trace Concentrations Using Degenerate Four-Wave Mixing with a Circularly Polarized Pulsed Probe Beam," Anal. Chem., 63(9):899-903, May 1991.

Wu, Z., et al., "Trace-Concentration Detection of Cobalt in a Liquid Flow Cell by Degenerate Four-Wave Mixing Using Low-Power Off-Resonant Laser Excitation," Anal. Chem., 63(18):1943-1947, Sep. 1991.

* cited by examiner

US 9,244,005 B2

ULTRASENSITIVE DETECTION OF ISOTOPES, CHEMICAL SUBSTANCES AND BIOLOGICAL SUBSTANCES USING LASER WAVE MIXING DETECTORS

PRIORITY CLAIMS AND RELATED PATENT APPLICATIONS

This patent document claims priorities under 35 USC §119 (e) to U.S. Provisional Application Ser. No. 61/143,746 entitled "Parts-Per-Quadrillion-Level Detection of Cesium Using Graphite Furnace-Coupled Laser Wave-Mixing Spectroscopy" and filed on Jan. 9, 2009, and U.S. Provisional Application Ser. No. 61/147,406 entitled "Detection of Biological and Chemical Substances in Liquids Using Optical Nonlinear Wave-Mixing" and filed on Jan. 26, 2009. The entire contents of the above patent applications are incorporated by reference as part of the disclosure of this document.

FEDERALLY SPONSORED RESEARCH OR DEVELOPMENT

This invention was made with governmental support under Grant No. 5-R01GM41032 awarded by the National Institute of General Medical Sciences, National Institutes of Health. The government has certain rights in the invention.

BACKGROUND

This document relates to optical sensing of various materials, including isotopes, chemical and biological substances.

Nonlinear four wave mixing is an optical process in an optical medium where three coherent optical waves interact with one another through nonlinear coupling to produce a fourth coherent signal wave. The nonlinearities of the medium, primarily the third-order nonlinear susceptibility of the medium in some implementations, contribute to such nonlinear coupling. The signal wave includes information on optically-excited atoms or molecules present in the medium where the three input optical waves intersect and hence can be collected to extract information about the medium. The strength of the signal wave is associated with the population of atoms or molecules and the spectral characteristics of the signal wave can be analyzed to reveal the structure of the atoms or molecules of interest. The coherent characteristics of the four-wave mixing signal beam have a number of advantages, including a laser-like signal beam, efficient signal collection, excellent spatial resolution, and sub-Doppler spectral resolution. Hence, four-wave mixing has been widely used as a highly sensitive tool in spectroscopic measurements.

SUMMARY

This document includes devices and techniques for using four wave mixing in optical sensing of various materials, including isotopes, chemical and biological substances.

In one implementation, a method is provided for using optical four wave mixing to detect cesium isotopes under ambient conditions to include operating an atomizer under ambient conditions without a high vacuum chamber to vaporize an analyte solution containing a sample to be measured for presence of one or more cesium isotopes; operating a tunable diode laser to produce a laser beam tuned at different wavelengths within a laser frequency tuning range for interacting with the sample in the atomizer; using optical components arranged to split the laser beam from the tunable diode laser into a first pump beam, a second pump beam and a probe beam in a four wave mixing configuration and to direct the probe beam and the first and second pump beams to overlap with one another at a location in the vaporized analyte solution produced by the atomizer; using an optical detector to receive light in a selected direction of a four wave mixing signal generated at the location in the vaporized analyte solution; and processing spectral components of a detector output of the optical detector corresponding to different wavelengths within the laser frequency tuning range to determine presence of one or more cesium isotopes in the sample.

In another implementation, a device is provided for using optical four wave mixing to detect cesium isotopes under ambient condition. This device includes an atomizer that vaporizes an analyte solution containing a sample to be measured for presence of one or more cesium isotopes under ambient conditions; a tunable diode laser that produces a laser beam tuned at different wavelengths within a laser frequency tuning range for interacting with the sample in the atomizer; optical components arranged to split the laser beam from the tunable diode laser into a first pump beam, a second pump beam and a probe beam in a four wave mixing configuration and to direct the probe beam and the first and second pump beams to overlap with one another at a location in the vaporized analyte solution produced by the atomizer; an optical detector that is positioned to receive light in a selected direction of a four wave mixing signal generated at the location in the vaporized analyte solution; and a signal detection module that processes spectral components of a detector output of the optical detector corresponding to different wavelengths within the laser frequency tuning range to determine presence of one or more cesium isotopes in the sample.

In another implementation, a method is provided for using optical four wave mixing to detect circular dichroism of a sample material. This method includes operating a capillary cell to provide an analyte solution containing a sample material to be measured for circular dichroism; operating a pump laser to produce a pump laser beam at a pump laser wavelength; using optical components arranged to split the pump laser beam into a first pump beam in a first pump linear polarization and a second pump beam in a second pump linear polarization orthogonal to the first pump linear polarization in a four wave mixing configuration to overlap with each another at a location in the analyte solution at the capillary cell; operating a probe laser to produce a probe laser beam at a probe laser wavelength different from the pump laser wavelength; directing the probe laser beam to the location in the in the analyte solution at the capillary cell in a direction for the four wave mixing configuration where the probe laser beam, the overlapped first and second pump beams and a four wave mixing signal beam at the probe laser wavelength interact to convert energy from the first and second pump beams into the four wave mixing signal beam; modulating the first pump beam in the first pump linear polarization at a modulation frequency to be alternatively in a right circularly polarized light state and a left circularly polarized light state; using an optical detector to receive light in a selected direction of the four wave mixing signal generated at the location in the analyte solution; and processing a detector output of the optical detector corresponding to the modulation frequency to measure different optical absorptions associated with the alternatively right circularly polarized light state and left circularly polarized light state and to determine circular dichroism of the sample material.

In another implementation, a device is provided for using optical four wave mixing to detect circular dichroism of a sample material. This device includes a capillary cell to provide an analyte solution containing a sample material to be measured for circular dichroism; a pump laser to produce a pump laser beam at a pump laser wavelength; pump optical components arranged to split the pump laser beam into a first pump beam in a first pump linear polarization and a second pump beam in a second pump linear polarization in a four wave mixing configuration to overlap with each another at a location in the analyte solution at the capillary cell; a probe laser to produce a probe laser beam at a probe laser wavelength different from the pump laser wavelength; one or more pump optical components that direct the probe laser beam to the location in the in the analyte solution at the capillary cell in a direction for the four wave mixing configuration where the probe laser beam, the overlapped first and second pump beams and a four wave mixing signal beam at the probe laser wavelength interact to convert energy from the first and second pump beams into the four wave mixing signal beam; a polarization modulation unit that modulates the first pump beam in the first pump linear polarization at a modulation frequency to be alternatively in a right circularly polarized light state and a left circularly polarized light state; an optical detector to receive light in a selected direction of the four wave mixing signal generated at the location in the analyte solution; and a signal processing module processing a detector output of the optical detector corresponding to the modulation frequency to measure different optical absorptions associated with the alternatively right circularly polarized light state and left circularly polarized light state and to determine circular dichroism of the sample material.

In another implementation, a method is provided for using optical four wave mixing to detect circular dichroism of a sample material. This method includes operating a capillary cell to provide an analyte solution containing a sample material to be measured for circular dichroism; operating a pump laser to produce a pump laser beam at a pump laser wavelength; using optical components arranged to split the pump laser beam into a first pump beam in a first pump linear polarization and a second pump beam in a second pump linear polarization in a four wave mixing configuration to overlap with each another at a location in the analyte solution at the capillary cell; operating a probe laser to produce a probe laser beam at a probe laser wavelength different from the pump laser wavelength; directing the probe laser beam to the location in the in the analyte solution at the capillary cell in a direction for the four wave mixing configuration where the probe laser beam, the overlapped first and second pump beams and a four wave mixing signal beam at the probe laser wavelength interact to convert energy from the first and second pump beams into the four wave mixing signal beam; modulating the first pump beam in the first pump linear polarization at a modulation frequency to be alternatively in the first pump linear polarization and in the second pump linear polarization; using an optical detector to receive light in a selected direction of the four wave mixing signal generated at the location in the analyte solution; and processing a detector output of the optical detector corresponding to the modulation frequency to measure different optical absorptions associated with the alternatively the first pump linear polarization and the second pump linear polarization and to determine circular dichroism of the sample material.

In another implementation, a method is provided for using optical four wave mixing to measure optical absorption of an analyte solution. This method includes using a capillary cell to hold an analyte solution containing a sample to be measured; operating a tunable laser to produce a laser beam tuned at different wavelengths within a laser frequency tuning range for interacting with the sample in the capillary cell; using optical components arranged to split the laser beam from the tunable laser into a first pump beam, a second pump beam and a probe beam in a four wave mixing configuration and to direct the probe beam and the first and second pump beams to overlap with one another at a location in the analyte solution; using an optical detector to receive light in a selected direction of a four wave mixing signal generated at the location in the analyte solution; and processing spectral components of a detector output of the optical detector corresponding to different wavelengths within the laser frequency tuning range to measure optical absorption of the sample within the laser frequency tuning range.

In another implementation, a device is provided for using optical four wave mixing to measure optical absorption of an analyte solution. This device includes a capillary cell to hold an analyte solution containing a sample to be measured; a tunable laser to produce a laser beam tuned at different wavelengths within a laser frequency tuning range for interacting with the sample in the capillary cell; optical components arranged to split the laser beam from the tunable laser into a first pump beam, a second pump beam and a probe beam in a four wave mixing configuration and to direct the probe beam and the first and second pump beams to overlap with one another at a location in the analyte solution; an optical detector to receive light in a selected direction of a four wave mixing signal generated at the location in the analyte solution; and a signal processing module processing spectral components of a detector output of the optical detector corresponding to different wavelengths within the laser frequency tuning range to measure optical absorption of the sample within the laser frequency tuning range.

In yet another implementation, a method is provided for using optical four wave mixing to measure a substance using a chromophore label. This method includes using a capillary cell to hold an analyte solution containing a chromophore label material which absorbs light at a first optical wavelength and a target substance to be measured to which the chromophore label material binds, wherein binding of the target substance and the chromophor label material causes the bounded material to absorb light at a second optical wavelength that is shifted from the first optical wavelength; operating a tunable laser to produce a laser beam tuned at different wavelengths within a laser frequency tuning range for interacting with the sample in the capillary cell; using optical components arranged to split the laser beam from the tunable laser into a first pump beam, a second pump beam and a probe beam in a four wave mixing configuration and to direct the probe beam and the first and second pump beams to overlap with one another at a location in the analyte solution; using an optical detector to receive light in a selected direction of a four wave mixing signal generated at the location in the analyte solution; and processing spectral components of a detector output of the optical detector corresponding to different wavelengths within the laser frequency tuning range to measure a shift in one or more spectral components of the sample relative to one or more spectral components of optical absorption of the chromophore label material that is free from binding with the target substance and to use the measured shift to measure the target substance in the analyte solution.

These and other implementations and their advantages and benefits are described in greater detail in the drawings, the description and the claims.

DETAILED DESCRIPTION

Figure 1:
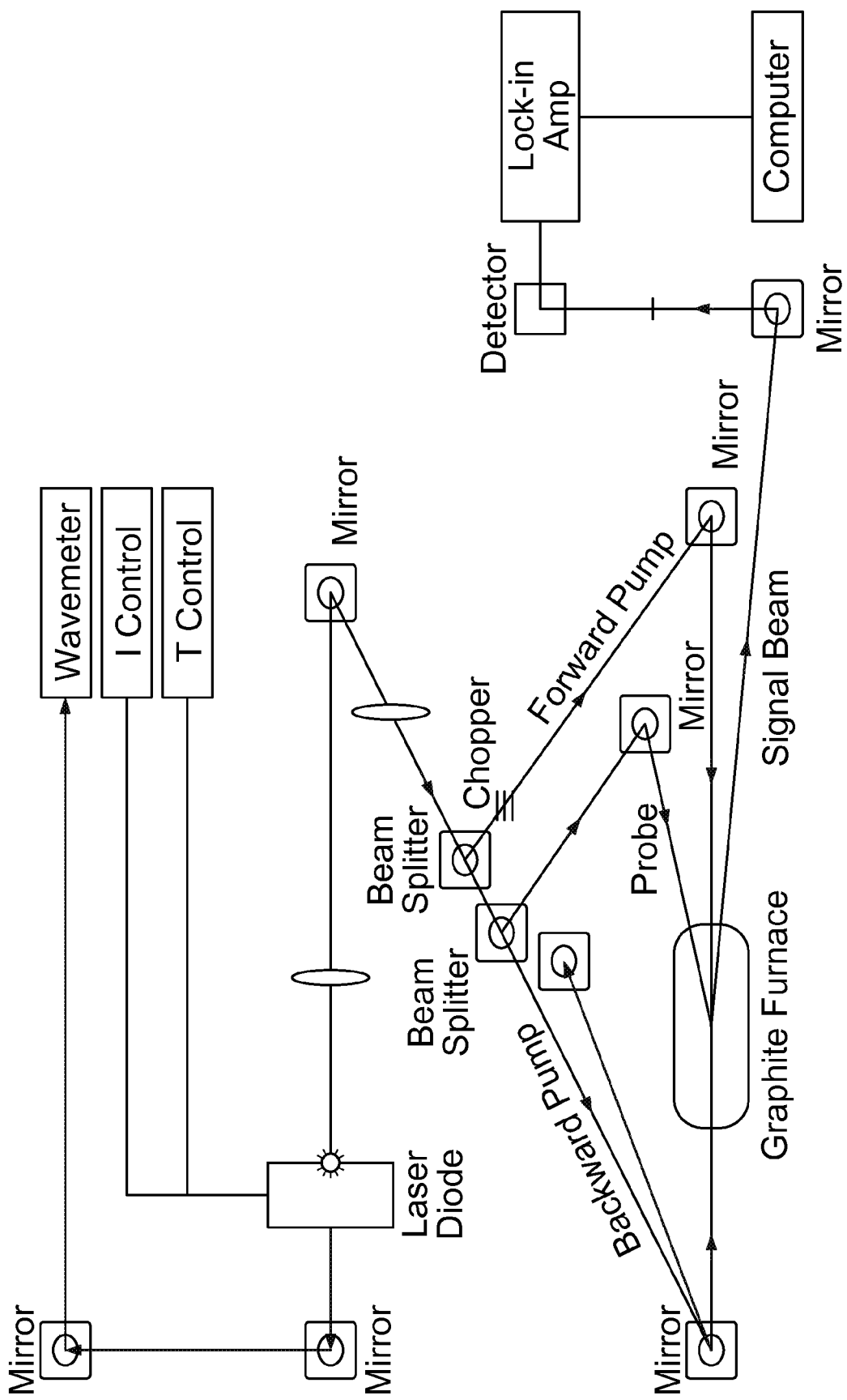
FIG. 1 shows an example of a backward-scattering laser wave-mixing optical detection device.

Optical sensing devices and techniques described in this document are designed for highly sensitive, selective and high-resolution sensing of various materials based on nonlinear laser wave mixing. Exemplary implementations of nonlinear wave mixing for measurements based on backward and forward scattering four wave mixing configurations are described.

Nonlinear optical wave mixing may be implemented in optical sensing systems with different configurations. Various four wave mixing systems may be used for detection of a minute amount of a substance. For example, U.S. Pat. No. 5,600,444 entitled "Detecting Analyte Light Absorption Utilizing Degenerate Four Wave Mixing" to Tong describes devices and techniques for using two-input-beam forward-scattering degenerate four-wave mixing to achieve ultrasensative analytical measurements of an analyte. Backward-scattering degenerate four-wave mixing has also be used for sensitive laser spectroscopic detection. See, e.g., U.S. Pat. No. 6,141,094 entitled "Sensitive Laser Spectroscopic Detection Based on Three-Dimensional Nonlinear Four-Wave Mixing" to Tong. U.S. patent application Ser. No. 10/540,224 entitled "Sensitive Sensing Based on Optical Nonlinear Wave Mixing" and published as U.S. Patent Publication No. US 2006-0263777 A1. The entire disclosures of the above referenced patent documents are incorporated by reference as part of the disclosure of this document. Techniques and features in the above-referenced patents may be used or combined with the techniques described in this document.

Nonlinear wave mixing techniques for sensitive high-resolution detection may be implemented with high temperature atomizers including graphite discharge plasmas, graphite furnace, inductively coupled plasma, and flame atomizers with detection sensitivity levels in the sub-parts-per-quadrillion levels. Applications to liquid-phase samples can achieve high detection sensitivity levels. The laser wave mixing methods offer many potential applications in many fields including chemistry, biology, and medicine. For example in biotechnology, laser wave mixing could be used for detecting biomolecules (e.g., proteins, DNAs, etc.) with or without labels or tags, for studying enzyme activities, for monitoring smaller chemical/biological changes more dramatically with less tedious procedures, for studying bio molecular structures, for analysis of small bio cells with high spatial resolution, for sensitive detection as sensors, and many other potential applications.

The laser wave mixing based detection methods may be useful for various applications in a wide range of fields for measuring atoms, isotopes (gas-phase) and molecules (liquid-phase) at detection levels that may be difficult to achieve with other sensing techniques. For example, laser wave mixing may be used to improve the detection sensitivity by a factor of about 1,000 to 1,000,000 relative to other sensing techniques. For example, preliminary detection limits for laser wave mixing may be obtained at sub-parts-per-quadrillion level, sub-attogram, sub-zeptomole, and sub-femto molar detection limits. Laser wave mixing may be effectively interfaced to popular gas-phase atomizers and liquid-phase flow systems for highly sensitive detection of e.g., gas-phase atoms and isotopes, at sub-Doppler spectral resolution and sensitive detection of liquid samples. In various implementations, laser wave mixing may be \ interfaced with a wide range of chemical instruments. Examples of the instruments include but are not limited to gas chromatographs (GC), liquid chromatographs (LC), mass spectrometers (MS), GC-MS, LC-MS, inductively coupled plasmas (ICP), ICP-MS, high performance/power capillary electrophoresis (HPCE) systems, flow injection analysis (FIA) systems.

In one aspect, nonlinear multi-photon laser wave-mixing spectroscopy is presented in this document as a sensitive and compact optical method for cesium isotope measurements in a wide range of atomizers including the graphite furnace atomizer and the inductively coupled plasma (ICP) atomizer. A backward-scattering wave-mixing optical setup is used to minimize Doppler broadening, i.e., to narrow spectral peaks and to yield spectral resolution that is suitable for isotope and hyperfine analyses. Spectral resolution is high enough to resolve not only individual isotopes of an element (atom), but also hyperfine lines of an isotope of an element. Utilizing a high-resolution compact tunable external cavity diode laser, the 6s $2S1/2 \rightarrow 2P3/2$ transition of cesium at 11,732.3 $cm^{-1}$ is measured. A detection limit of 3.75 parts-per-quadrillion is determined using the graphite furnace and an excellent fit to the theoretical hyperfine profile is obtained for effective spectra deconvolution, i.e., determination of isotope ratios and isotope identification. To our knowledge, our detection limit represents the lowest reported detection limits for cesium at room pressure. Hyperfine structure scans of these isotopes agree very well with theoretical hyperfine profiles, allowing effective monitoring of in-situ environmental and nuclear cesium 137 isotopes. While the graphite furnace atomizer offers better detection sensitivity levels, the ICP atomizer allows faster scans with less background noise.

Novel nonlinear multi-photon four-wave mixing spectroscopy is presented as an ultrasensitive parts-per-quadrillion-level detector for cesium isotopes, with up to a million times more sensitive detection sensitivity levels as compared to those from isotope-capable mass spectrometers. Sub-parts-per-quadrillion level detection of cesium isotopes demonstrated in room pressure, i.e., without using bulky and heavy vacuum chambers used in isotope capable mass spectrometers. Novel nonlinear multi-photon four-wave mixing spectroscopy is presented as a relatively compact and portable detector for cesium isotopes as compared to currently available methods including heavy, bulky, high-resolution, vacuum chamber-based isotope capable mass spectrometers (all small bench-top mass spectrometers are not isotope capable). Wave mixing allows rugged solid-state laser-based isotope detection, unlike fragile vacuum chamber-based mass spectrometers. Multi-photon backward-scattering four-wave mixing optical setup minimizes Doppler broadening, resulting in much narrower spectral peaks and much higher spectral resolution that is suitable for high-resolution isotope and hyperfine analyses. Spectral resolution is high enough to resolve not only individual isotopes of an element (atom), but also hyperfine lines of isotopes of an element. Unique combination of all three critical features (sensitivity, portability and specificity) yields effective and reliable application of wave mixing as on-site isotope detectors. Other isotope detectors offer just one or two of these three critical features. Portable, rugged and field usable isotope detectors offer new applications previously though impossible including those for security, environmental and biomedical applications where radioisotopes of cesium are used in non-invasive biological monitoring, cancer research and radiation therapy. Greater understanding of these isotopes will open doors to new and less dangerous applications of isotopic tracers and therapeutic agents.

Cesium and its isotopes offer many potential applications including environmental, biomedical and archaeometric studies. Of foremost importance is the fact that the heaviest isotope of this element, cesium 137, is a high energy $\beta^-$ and $\gamma$ emitter, and a pervasive environmental pollutant with a long half-life of 136.9 years. Along with cesium 134 and strontium 90 isotopes, it is considered to be one of the most dangerous isotopes resulting from nuclear fallouts (1). Radioactive cesium 137 is a by-product of fission reactions with uranium and plutonium that occur in nuclear reactors and weapon discharges. Prior to 1950, there was no measurable amount of radioactive cesium in the environment. With the dawn of the nuclear industry, this situation has radically changed. Mine tailings containing small radioactive particles may be swept away by winds to accumulate elsewhere or washed away by erosion and rain to accumulate in nearby lakes and rivers (2). The abrupt rise in the measurable amount of cesium has enabled some researchers to utilize cesium signatures in lake sediment to date nearby mine waste sites (3).

TABLE 1

Isotopes of Cesium

| Isotope | Mass | $\tau_{1/2}$ | % Natural Abundance | Nuclear Spin (I) |
|---|---|---|---|---|
| 133 | 132.905429 | Stable | 100 | 7/2 |
| 129 | 128.906060 | 1.336 d | 0 | 1/2 |
| 130 | 129.906710 | 29.21 m | 0 | 1 |
| 131 | 130.905460 | 9.69 d | 0 | 5/2 |
| 132 | 131.906430 | 6.48 d | 0 | 2 |
| 134 | 133.906714 | 2.065 y | 0 | 4 |
| 135 | 134.905972 | $2.3 \times 10^6$ y | 0 | 7/2 |
| 136 | 135.907307 | 13.16 d | 0 | 5 |
| 137 | 136.907085 | 30.2 y | 0 | 7/2 |

Further environmental accumulation has resulted from various nuclear weapon tests in the 1960s, hospital wastes due to the use of radioactive cesium as a medical diagnostic tracer, and nuclear reactor accidents such as those in Chernobyl and Three Mile Island. Although there were no significant amounts of cesium 137 before in the environment, there are now measurable amounts of this dangerous isotope in water, soils and even people (3). Cesium 134 is also found as an environmental pollutant, although it is much less abundant and has a much shorter half-life of 2.065 years, as shown in Table 1.

Cesium 137 mostly originates as a fission product of radioactive uranium. Once released into the environment, cesium acts much the same way as potassium due to their chemical similarities. Cesium 137 isotopes can replace potassium in bones, muscle and gonad tissue, as well as concentrate in the milk of both livestock and humans, which lends the added risk of this isotope being concentrated in the food chain. Once concentrated in the body, cesium 137 can deposit its Gamma and Beta energy into living cells, resulting in cell damage, mutation and deleterious reproductive effects (4, 5). Fallout measurements and their effects on humans and livestock have been studied in detail following large scale accidents, e.g., Chernobyl (5, 6) in 1986 and smaller scale accidents in Goiânia, Brazil, in 1987 (7).

Further interest in this isotope lies in the biomedical field where radioisotopes of cesium are used in non-invasive biological monitoring, cancer research and radiation therapy (4, 8). Greater understanding of this element and the development of new and more sensitive detection methods could open doors to new and less dangerous applications of isotopic tracers and therapeutic agents.

Cesium has also realized a metrological importance over the past few decades. Its atomic energy levels, both in a natural state or via a magneto-optical trap, can be measured with excellent precision. In 1967, the 13th Conference on Weights and Measures defined the SI unit of the second as the amount of time required for 9,192,631,770 Hz of light absorbed or emitted by an undisturbed hyperfine transition of ground-state cesium 133 atoms (9). Meteorological and physical interpretations of the electronic structure of cesium have led several research groups to study its fine and hyperfine structures as well as isotope shifts and line broadening (10-14).

Cesium has a very strong resonance transition in the near infrared region at 852 nm. The strength of this line offers not only excellent detection limits (15, 16), but also reliable measurements of its fine and hyperfine spectra (10-14). Cesium isotope and hyperfine structure measurements have been performed using atomic beams, heat-pipe ovens, magneto-optical traps and other highly concentrated or confined atomic sources. However, such methods are impractical for measurement of select isotopic species or hyperfine profiles in real-world applications at room pressure. Typical measurements of radioactive species are performed using nuclear detection methods such as neutron activation analysis (NAA), Gamma counting or other specialized instruments where high-energy particles are measured instead of the actual species of interest (17, 18). These methods carry the inherent disadvantages of poor detection sensitivity and complicated and expensive setups as compared to a direct optical absorption-based technique.

Hyperfine Structure of Cesium. There are nine cesium isotopes and only one of them, cesium 133, is naturally occurring. All Cs isotopes have non-zero nuclear spins (i.e., I≠0), and therefore, they show hyperfine structures, as shown in Table 1. The Cs ground state is a doublet state with the 2S1/2 term. Upon absorption of radiation at 11,732.3 cm$^{-1}$, an unpaired electron from the 6s shell is promoted to the 6p shell with an excited-state term symbol of 2P3/2. This particular transition is desirable for use in analytical applications for two reasons. First, it originates from a highly populated ground state so that a strong absorption-based signal can be obtained. Secondly, the transition lies in the near-IR wavelength range that is well suited to the utilization of a compact semiconductor diode laser.

Compact diode lasers offer several advantages over conventional light sources such as hollow-cathode lamps and other bulky laser sources such as pulsed dye laser systems. Unlike fixed-frequency sources such as conventional hollow-cathode lamps, a semiconductor diode laser is tunable over a few nanometers, enough to probe the entire isotope and hyperfine profiles of an element. Additional features, including low cost, durability, narrow line width (kHz range) and ease of use, make diode lasers attractive as compared to bulky dye, OPO and Ti:Sapphire-based lasers available in the UV, visible and near-IR wavelength regions (19, 20).

In order to minimize common problems associated with conventional diode lasers, such as mode hopping and poor beam divergence, it is advantageous to employ an external cavity tunable diode laser (ECDL). In the following sections, an ECDL is used as an excitation source for Cs wave-mixing detection in the graphite furnace atomizer and the ICP. In addition to minimum frequency instabilities and shifts and cleaner spatial beam profiles, the ECDL also offers a much narrower line width as compared to those of conventional diode lasers.

Laser Wave Mixing. Degenerate four-wave mixing is a resonant nonlinear technique that offers several advantages over both conventional spectroscopic methods and other popular analytical techniques. In wave mixing, two light waves interact inside an absorbing analyte. One of these beams is designated the probe beam while the other may be either the backward or the forward pump beam depending on which two of the beams will interact and generate a stronger grating. When two of these beams are allowed to interact inside an absorbing analyte, constructive and destructive interferences form population gratings (21, 22). The spacing between the grating fringes is given by:

$$d = \frac{\lambda}{2\sin\left(\frac{\theta}{2}\right)} \qquad (1)$$

where d is the distance between each fringe, $\lambda$ is the wavelength of the input radiation and $\theta$ is the angle of overlap between each beam. A larger overlap angle results in fringe spacings that are much less defined and they tend to wash out with random motion and thermal effects. Such a situation is encountered with the overlap of the probe beam and the backward pump beam where a narrow period grating is developed. This grating is weaker than the grating formed by the interaction between the forward pump beam and the probe beam.

When a third beam, the backward pump, is allowed to interact in the same region, it scatters off the grating to generate the signal beam. Phase conservation precisely predicts the propagation direction of this beam, and hence, templates can be positioned and used for optical alignment. Since the scattered signal is a laser-like coherent beam measured against a dark background with a precisely known propagation direction, appropriate spatial filters can be added to reduce background noise levels. Hence, optical collection efficiency is high and one can obtain high S/N and excellent detection sensitivity levels. The signal beam intensity is given by $$I_{Signal} = \alpha^2 L^2 \frac{1}{1+\delta^2} \frac{4(I_{pump}/I_{sat})^2}{(1+4I_{pump}/I_{sat})^2} \quad (2)$$

where $\alpha_o$, the line center absorption coefficient, is given by:

$$\alpha_o = \omega \frac{\Delta N_o |\mu_{1,2}|^2 T_2}{2c\hbar\varepsilon} \quad (3)$$

and the saturation intensity, $I_{sat}$ is given by:

$$I_{sat} = \frac{\varepsilon_o c\hbar^2}{2T_1 T_2 |\mu_{1,2}|^2}(1+\delta^2) \quad (4)$$

More generally, Equation 2 can be represented as $$I_{signal} \propto \frac{3}{2} I_{probe} \pi \alpha_o^2 L^2 \left(\frac{I_{pump}}{I_{sat}}\right)^2 \quad (5)$$

where Iprobe and Ipump are the intensities of the grating-forming beams, Isat is the saturation intensity, α is the line center absorption coefficient, and L is the interaction length between the input beams. Unlike conventional absorption methods with a linear relationship between signal intensity and concentration, the wave-mixing signal has a quadratic dependence on analyte concentration (α2), and we have demonstrated parts-per-trillion (ppt) and parts-per-quadrillion (ppq) detection limits (23). The wave-mixing signal also a cubic dependence on laser power, hence, one can take advantage of low-power lasers, as described in this report. In wave mixing, Doppler broadening of the analyte line width is also effectively reduced due to the use of counter propagating input beams.

Laser wave mixing is well suited to a wide range of applications including trace analyses of gas, aqueous and solid samples, profile mapping of flames and plasmas, isotope-ratio measurements, optical data storage, and the empirical assessment of the theoretical models for atomic energy levels and hyperfine and isotope shift values. Wave mixing can be also interfaced to various popular commercially available atomization sources. Using a commercial graphite furnace atomizer, we obtain sub-parts-per-quadrillion (ppq) detection limits and we also match experimental hyperfine structures with those of theoretical profiles (23, 24).

The use of a relatively compact and portable high-resolution tunable external cavity diode laser allows a compact overall detector design with a small foot print. Compact tunable diode lasers offer several advantages over other tunable or fixed-wavelength light sources such as hollow-cathode lamps and bulky tunable laser sources such as pulsed dye laser systems. Unlike fixed-frequency sources such as conventional hollow-cathode lamps, a semiconductor diode laser is tunable over a few nanometers, enough to probe the entire isotope and hyperfine profiles of an element. Additional features, including low cost, durability, narrow line width (kHz range) and ease of use, make tunable diode lasers attractive as compared to bulky dye, OPO and Ti:Sapphire-based lasers available in the UV, visible and near-IR wavelength regions. Unlike other laser methods, wave mixing can efficiently use low power levels available from compact tunable lasers, and hence, it offers compact, rugged, all-solid-state, portable isotope detector designs.

Wave mixing offers strong signals, and hence, allows detection of cesium isotopes using relatively weak transition lines, e.g., transition line at 11,732.3 cm-1, instead of much stronger ground-state transition lines that are most commonly used by other methods. This in turn allows the use of more convenient tunable lasers and wavelength ranges (e.g., visible and near IR) instead of more bulky tunable UV lasers, making it possible to design more compact isotope detectors.

Wave mixing allows ultrasensitive sub-parts-per-quadrillion level detection using commercially available graphite furnace atomizers. Wave mixing allows fast real-time detection using commercially available inductively coupled plasma (ICP) atomizers. Since the ICP is a continuously firing atomizer, one can collect the wave-mixing signal at a much higher sampling rate as compared to those for the graphite furnace atomizer. Sensitive and compact detection of isotopes using off-the-shelf commercially available atomizers including but not limited to graphite furnace and inductively coupled plasma atomizers.

FIG. 1 shows a wave-mixing optical setup. The output beam from a commercially available external cavity diode laser (New Focus, Inc., Santa Clara, Calif.) is split into three separate beams using 30:70 and 70:30 (R/T) beam splitters. The beam splitter ratios are chosen in order to arrange more laser intensity to the two input beams that produce the strong grating, i.e., the forward pump beam and the probe beam. Laser power levels for these two beams are kept at 3.15 and 3.20 mW while the backward pump beam power is kept at 0.96 mW. The three input beams are directed into a modified graphite furnace (Varian, Inc., Mulgrave, Victoria Australia) that is removed from its spectrometer housing and placed on the optical bench at the intersection of the three input laser beams. The Quartz windows of the furnace are adjusted to minimize optical noise due to scattering. A XYZ translational stage is used for beam adjustments within the graphite tube and to optimize signal strength.

The external cavity diode laser wavelength is tunable from 833 nm to 853 nm with a total continuous-wave power of 12.9 mW. For detection limit studies, the laser power can be increased to 23 mW, however, wavelength tuning is more challenging at these laser diode current and power levels due to mode hopping. A 1000-mm focal-length lens is used to collimate the three beams into the furnace graphite tube. After passing through the graphite tube, a portion of the probe beam is reflected into a wavemeter (Burleigh Instruments, Fishers, N.Y., Model WA-20VIS) for continuous monitoring of the laser wavelength. The wave-mixing signal is then guided by a mirror through spatial, polarization and line filters into a simple photodiode that is mounted on a translational stage to ensure optimal signal collection. The backward pump beam is modulated at 1.3 kHz with a mechanical chopper (Stanford Research Systems, Inc., Sunnyvale, Calif., Model SR-540) and the signal is fed to a digital lock-in amplifier (Stanford Research Systems, Inc., Sunnyvale, Calif., Model SR-830DSP), an analog-to-digital converter, and finally to a personal computer for display and analysis. The optical alignment is relatively straightforward due to the use of alignment templates for the input beams and the signal beam. Due to the nature of the coherent laser-like signal beam and the spatial filters employed, the entire optical setup can be performed with the room lights on.

Analyte solutions are prepared from 99% optical grade CsCl (Sigma Aldrich, Milwaukee, Wis.) and diluted to volume with 0.1% HNO3 using ultra-pure doubly-deionized water. Throughout the sample preparation and treatment processes, care is taken to avoid Cs contamination from dissolved ions in the water and leaching from the walls of the glassware. Glassware is pretreated by soaking 72 hours in 50% HNO3 and rinsing thoroughly with ultra pure water. This is especially important for our detection limit studies due to the extremely low concentration levels being measured. Fresh cesium stock solutions are used since older solutions could result in much lower analytical signals due to cesium leaching into the storage glassware.

Before each analysis, sample and matrix (0.1% HNO3) solutions are loaded into sampler cups of the graphite furnace sampler assembly using a micropipette. High purity argon purge gas is used to prevent oxidation of the graphite tube and to sweep out residuals in each step up to the final atomization step. During the three-second atomization stage, the wave-mixing signal is collected with the lock-in amplifier and care is taken to isolate and minimize AC and RF noise sources.

Wave mixing-based measurement of atomic cesium allows reliable in-situ optical detection of radioactive cesium isotopes. Wave mixing allows reliable and effective monitoring of both environmental and nuclear cesium 137 isotopes. Wave mixing allows better isotope fingerprinting as compared to Geiger counters, i.e., minimum false positives. Wave mixing yields isotope information in seconds, not minutes, hours or days. High spectral resolution of wave mixing (Doppler-free and hyperfine specific) offers minimum chemical and spectral interference problems, and hence, minimum false positives and false negatives. Wave mixing offers reliable calculation of theoretical hyperfine profiles and excellent fit to experimental hyperfine profiles of isotopes, allowing reliable isotope ratio determinations. Wave mixing offers many advantages (ease of use, portability, minimum sample preparation steps, fast sample analysis time, better chemical specificity, less chemical interferences, less physical interference, higher signal-to-noise ratios, etc.) as compared to currently available methods including but not limited to neutron activation analysis (NAA), Gamma counting or other specialized instruments where high-energy particles are measured instead of the actual species of interest. These methods carry the inherent disadvantages of poor detection sensitivity and complicated and expensive setups as compared to a direct optical absorption-based technique.

Wave mixing not only offers very high spectral resolution for excellent chemical selectivity and specificity levels, but also excellent detection limits that are orders of magnitude (up to a million times) better than comparably isotope capable mass spectrometers. For example, we obtained a concentration detection limit of 3.75 ppq at S/N 2 for Cs, corresponding to a mass detection limit of $3.75 \times 10^{-17}$ g, 37.5 attograms or $1.7 \times 10^5$ atoms inside the laser probe volume.

Figure 8:
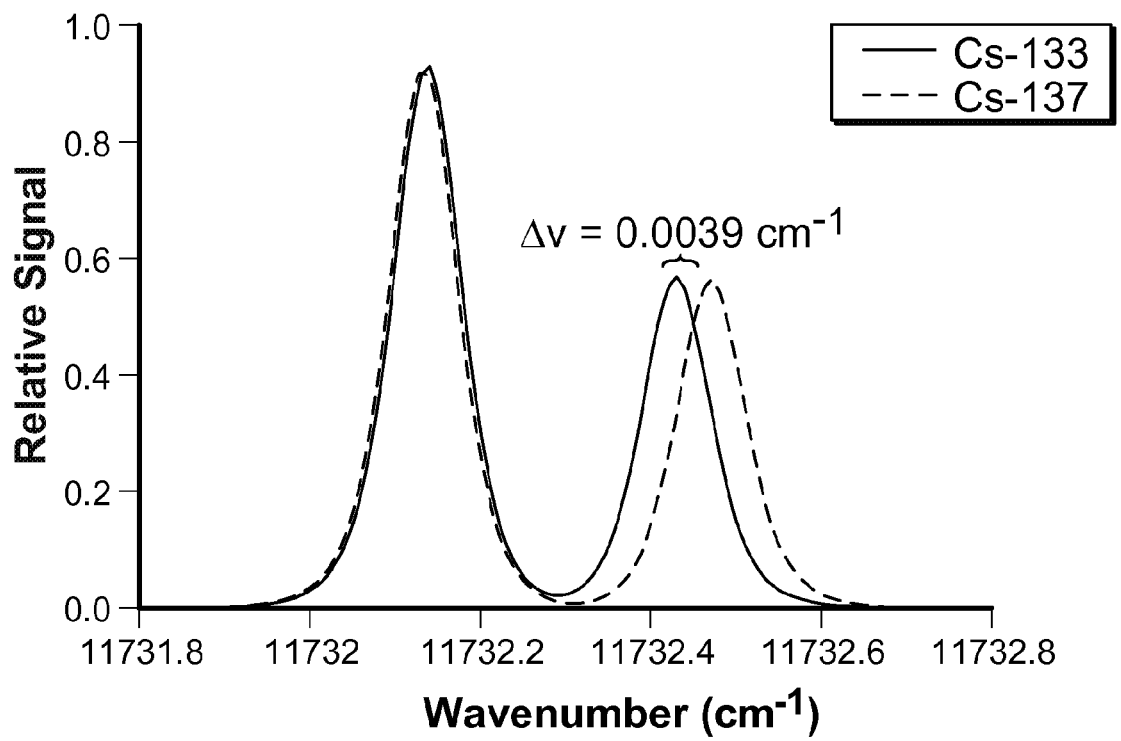
FIG. 8 shows an example of a simulated spectrum of radioactive cesium 137 isotope. A 50-50 mix of cesium 133 and cesium 137 isotopes is modeled to demonstrate the effectiveness of wave mixing in detecting the radioactive cesium 137 isotope.

A high content of cesium 137 may be encountered in the topsoil, litter, roots, grass or animal tissue in a nuclear fallout area and trace-concentration detection of the cesium 137 isotope is of great importance for the analysis of fallout products or nuclear waste. As shown in FIG. 8, the first peaks of both isotopes are indistinguishable from each other while the second peaks are significantly separated by 0.0039 cm-1. Nonlinear wave-mixing offers sub-Doppler line widths, and hence, high spectral resolution necessary to distinguish cesium 133 and cesium 137 and to directly detect cesium 137 isotopes.

Figure 2:
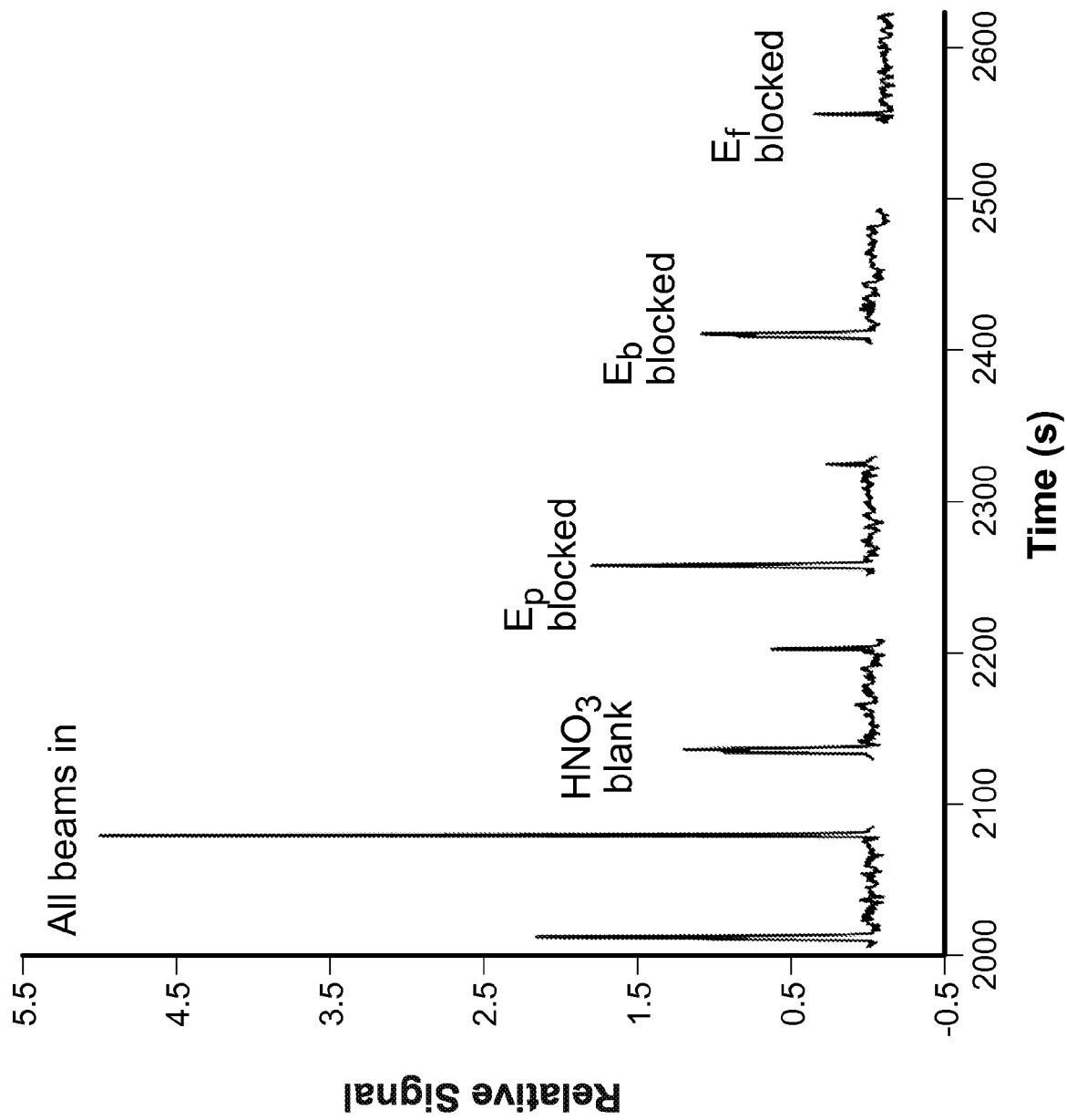
FIG. 2 shows an example of measurements of wave-mixing signal peaks in the graphite furnace for 20 ppb cesium. Subsequent firings of blanks or blocking one of the three input beams (probe, forward, backward) result in no signal peak.

FIG. 2 shows a typical wave-mixing signal for cesium in the graphite furnace. The first run is collected for a 20 ppb Cs analyte with all input beams directed into the furnace. The next spectrum is collected using the same experimental conditions except with only a blank solution deposited in the furnace graphite tube. While the cesium signal peak clearly stands out in the first trace, atomization of the blank HNO3 solution produces only a small peak due to some memory effect from previous firing runs. This residual Cs memory is easily removed by firing a few blank solution runs. Subsequent blank runs show background levels well within the baseline noise. Systematic, i.e., injection, peaks at the beginning of each run are due to random scattering of laser light from the reflective surface of the sample injector arm. To further verify the wave-mixing signal, a beam blocker is inserted temporarily in the path of each of the three input beams (i.e., forward Ef, backward Eb and probe Ep) to make sure that no signal is present upon atomization of the sample. Finally, the cesium analyte is replaced with a blank matrix solution to make sure that the Cs peaks are significantly and reproducibly higher than the blank peaks.

Figure 3:
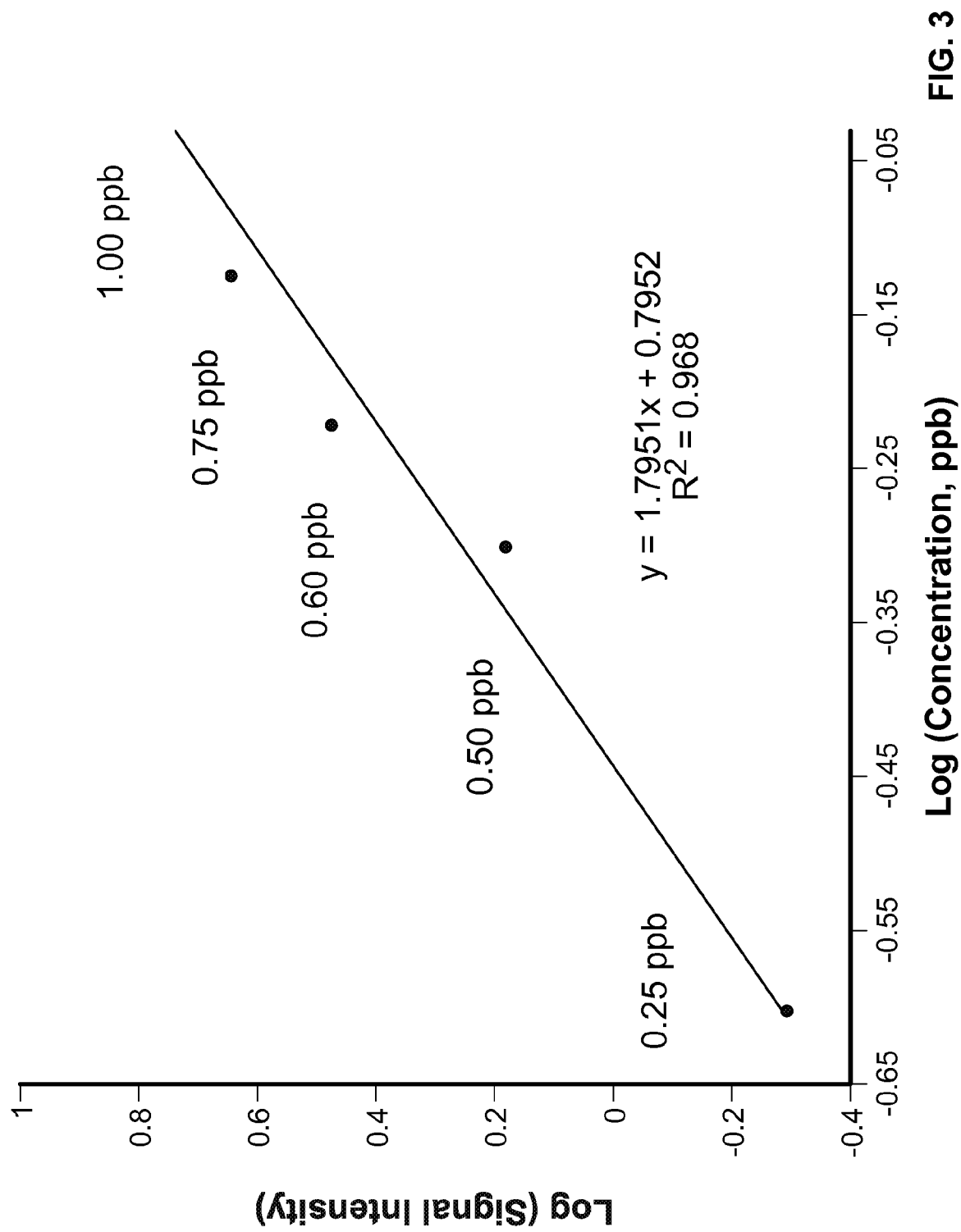
FIG. 3 shows a log-log plot of signal vs. concentration demonstrating a quadratic dependence with a slope of 1.8.

FIG. 3 shows further verification of the wave-mixing signal. A log-log plot of the signal intensity and analyte concentration yields a slope of 1.8, close to the expected slope of 2.0, as predicted by Equation 2. The measured slope (1.8) is slightly lower than the theoretical slope (2.0) due to residual optical background noise levels reaching the detector. FIG. 3 also illustrates a unique feature of wave mixing, i.e., its capability to monitor "smaller chemical changes" in analytes more dramatically and efficiently.

Figure 4:
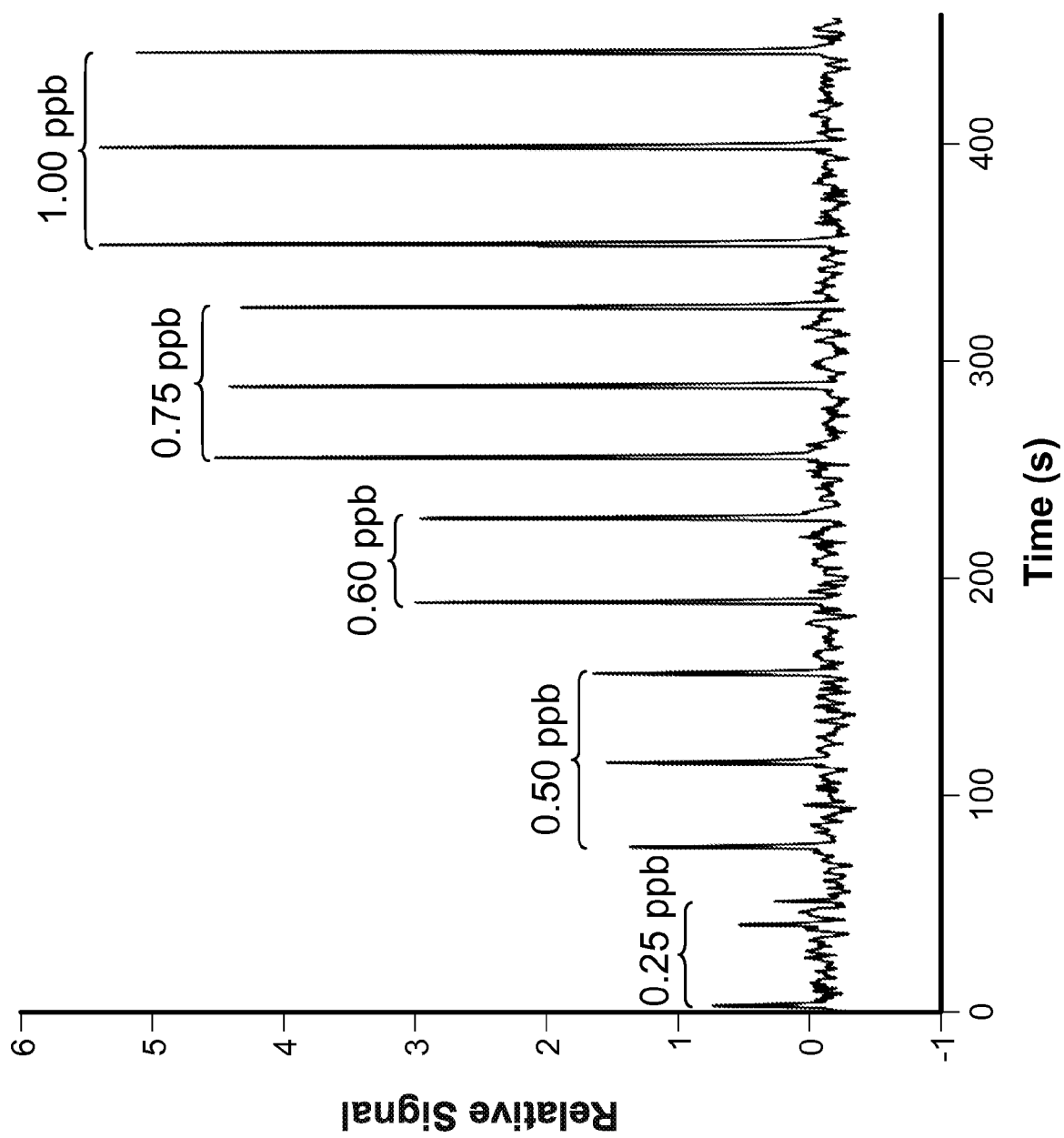
FIG. 4 shows an example of measurements of reproducible Cs wave-mixing signal peaks for a series of cesium concentrations from 0.25 to 1.0 ppb with three graphite runs in each step.

FIG. 4 shows reproducibility for multiple furnace firings using increasing cesium concentration levels. In order to minimize tube contamination and other undesirable memory effects, blank 0.1% HNO3 matrix firings are used between successive sample firings, resulting in blank firings buried well within the background noise of the scan and no further memory effects in subsequent sample runs. After obtaining the wave-mixing signal and lowering the limit of detection to parts-per-quadrillion levels, a hyperfine spectrum of cesium-133 is measured as described below.

In order to determine optimum conditions for the graphite furnace signal, different matrix and modifier solutions are tested to check if they offer any level of signal enhancement. The effect on signal by solution matrix is examined using 0.1% HNO3, 0.1% H2SO4 and 0.1% HCl matrix solutions. Signal intensities obtained with the sulfuric acid and hydrochloric acid matrices are virtually indistinguishable from one another, and they are both slightly lower than that obtained with the nitric acid matrix. The modifier solution is expected to prevent early loss of cesium during the pre-atomization stages of the furnace operation. Previous reports recommend the use of 0.1% H2SO4 in cesium samples in the graphite furnace for sensitivity enhancement (25). However, our preliminary study indicates that signal strengths, both in peak area and peak height, are not enhanced when using this modifier. Hence, a standard 0.1% nitric acid matrix, without any modifier, is used for all subsequent graphite-furnace runs.

Figure 5:
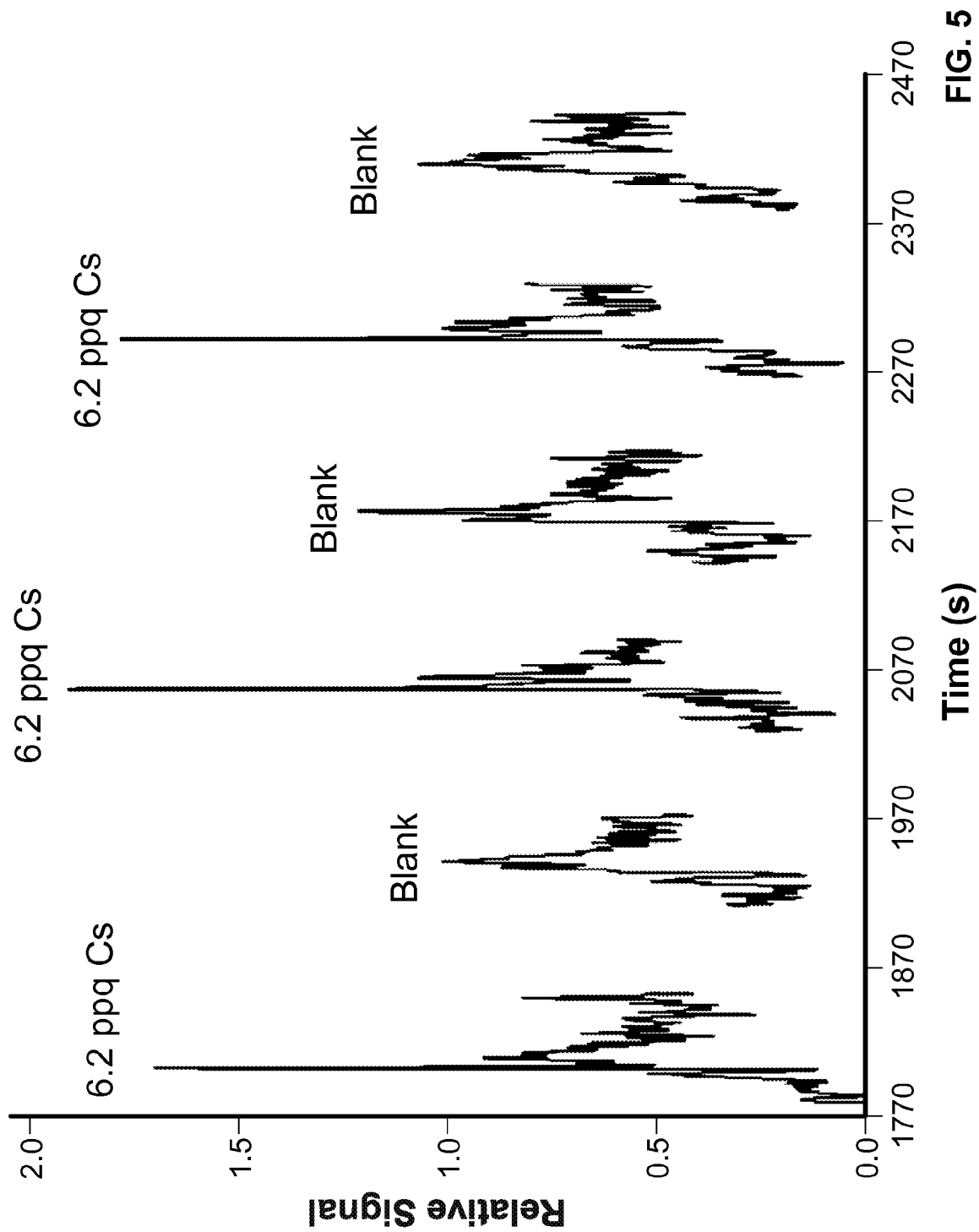
FIG. 5 shows an example of measurements of reproducible wave-mixing signals from 6.2 parts-per-quadrillion (ppq) cesium analytes in the graphite furnace.

FIG. 5 shows three reproducible wave-mixing signal peaks for a 6.2 parts-per-quadrillion Cs analyte. A preliminary concentration detection limit of 3.75 ppq at S/N 2 is determined for Cs in this graphite furnace setup. Taking into account the amount of sample used (10 μL), a preliminary mass detection limit of $3.75 \times 10^{-17}$ g, 37.5 attograms or $1.7 \times 10^5$ atoms is determined for Cs. The laser probe volume, i.e., overlap volume of the input laser beams, is very small and we estimate it to be 13.45 mm3. In addition, one must take into account other analyte loss processes such as adsorption into the graphite tube. Conservatively estimating this loss at 10%, the calculated number of Cs atoms responsible for the wave-mixing signal is only approximately 700 atoms. Our detection limits compare well with those previously reported for Cs, without using more powerful lasers and avalanche amplification steps as in other methods listed (15, 16, 25-32).

Figure 6:
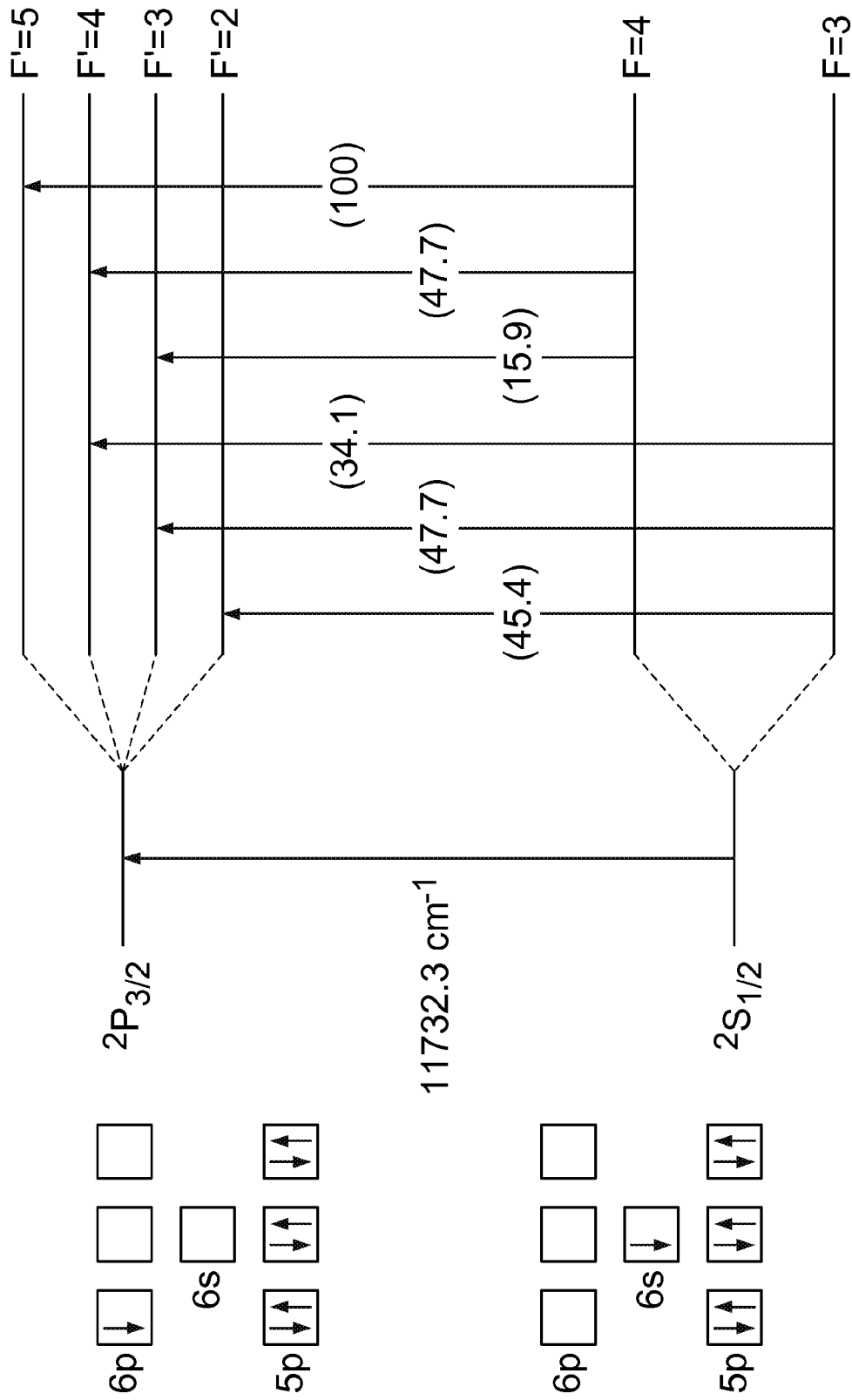
FIG. 6 shows the hyperfine splitting diagram for cesium. Two distinct fine structure bands are shown that arise from the F=3 and F=4 sublevels of the ground state. Each fine structure peak is expected to result from contributions from the hyperfine lines of cesium 133, which has a non-zero nuclear spin.

As shown in FIG. 6, the hyperfine structure of cesium shows two distinct fine splitting bands at 11,732.1 cm-1 and 11,732.4 cm-1 arising from the F=3 and F=4 sublevels of the 2S1/2 ground state. The lower energy band yields slightly higher peak intensity due to its larger hyperfine contribution to the total structure. Since cesium 133 is the only naturally abundant isotope, there is no isotope splitting contribution to the overall spectral profile.

Figure 7A:
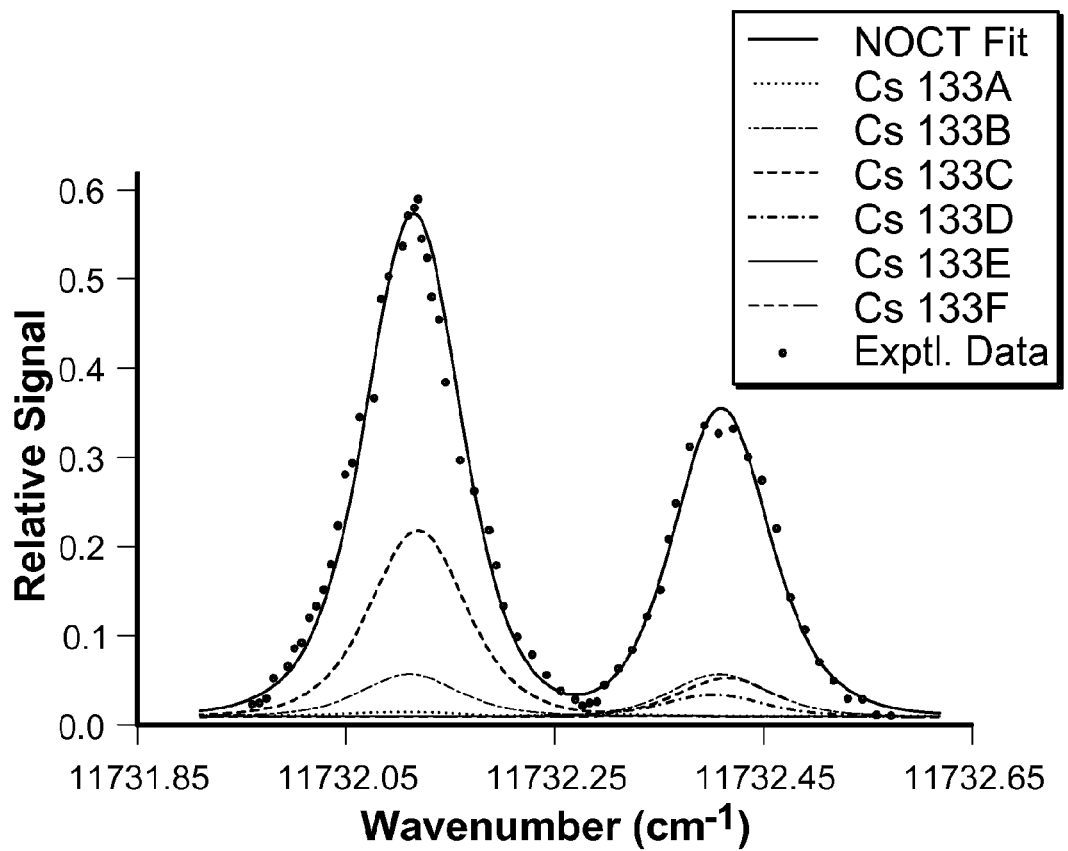
FIGS. 7a and 7b show examples of measured hyperfine spectrum of 30 ppt cesium collected in the graphite furnace. (a) Experimental data points are shown as dots overlaid on the expected profile calculated by the nonlinear optical coherence theory (NOCT), and (b) enlarged to show details.
Figure 7B:
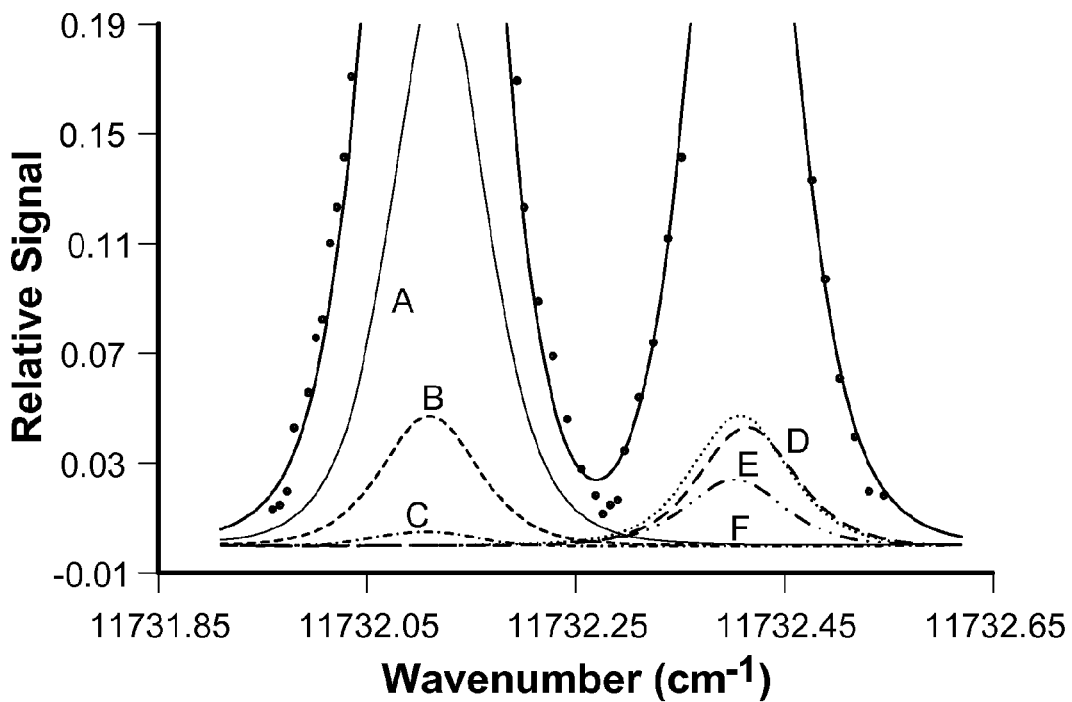

FIG. 7 shows experimental wave-mixing hyperfine spectrum collected for a 30 ppt Cs analyte solution. Each data point represents an average of two different graphite furnace firings at the same wavelength. This averaging allows correction for some deviations between firings including alignment drifts, electrical fluctuations and wavelength shifts. Between each sample firing, a blank solution of HNO3 is injected (not shown in the figure) to make sure there is no memory effect contributing to the wave-mixing signal. Overlaid on the experimental hyperfine spectrum is a theoretical hyperfine profile calculated based on our custom nonlinear optical coherence theory (NOCT) that accounts for the sub-Doppler nature of the expected experimental line widths. Using temperature increments of 250 K and pressure increments of 5 kPa, the experimental data in FIG. 7 is least squares fitted to that from the NOCT in order to determine the best temperature and pressure values.

Based on these calculations, temperature and pressure inside the laser probe volume are determined to be 2000 K and 145 kPa or 1.43 atm, respectively. As expected, the calculated analyte temperature is lower than the atomization temperature programmed and generated by the graphite furnace, since the laser probe location is a few millimeters away from the graphite tube walls. It is at these walls that the maximum temperature is expected during furnace firing (25). As the vapor plume is generated, the atom population is no longer at the graphite wall, and therefore, expected to be cooler. Temporary deviations from room pressure are expected from an analyte that is confined inside the small cavity of the notched partition graphite tube during the heating process. This confinement during the final temperature ramp stage in the graphite furnace yields a larger population of atoms that can interact with the laser beams.

Wave mixing-based measurement of atomic cesium also allows in-situ optical detection of radioactive cesium isotopes. FIG. 8 shows a simulated hyperfine spectrum for a 50-50 mixture of cesium 133 and cesium 137 isotopes in the graphite furnace. Such a high content of cesium 137 may be encountered in the topsoil, litter, roots, grass or animal tissue in a nuclear fallout area (33). Trace-concentration detection of the cesium 137 isotope is of great importance for the analysis of fallout products or nuclear waste. As shown in FIG. 8, the first peaks of both isotopes are indistinguishable from each other while the second peaks are significantly separated by 0.0039 cm-1. Nonlinear wave-mixing offers sub-Doppler line widths, and hence, high spectral resolution necessary to distinguish and directly detect cesium 137 isotopes.

Hyperfine Scans with the ICP atomizer. While accuracy is excellent for quick hyperfine scans in the graphite furnace, it is necessary to keep experimental conditions constant when a detailed hyperfine profile is scanned, e.g., over a relatively long time for 60 data points and 180 furnace firings, including blanks, due to the "intermittent" nature of the graphite furnace atomizer. For faster scans, an inductively coupled plasma (ICP) atomizer or another "continuous" atomizer can be used. A modified commercial ICP torch (RF Plasma Products, Inc., Voorhees, N.J., Model AMN 2500) is used to collect wave-mixing signals for cesium. All ICP runs are performed using 1000 ppm Cs stock solutions. Sample is continuously introduced by a peristaltic pump at a rate of 2.5 mL/min. Gas flow rates are maintained at 1.2 L/min, 0.5 L/min and 2.0 L/min for the plasma, nebulizer and auxiliary lines, respectively. To increase the cesium signal intensity, a 500 ppm solution of KC1 is used as the ionization suppressor. The lower ionization potential of potassium reduces cesium population loss due to ionization in the ICP. This results in a three-fold increase in observed wave-mixing signal for cesium.

As expected, the ICP RF power also has an effect on signal intensity. While our ICP plasma can be maintained over a range of 618 W to 878 W of RF power, the lowest setting (618 W) is used to further minimize cesium ionization loss, and therefore, enhance the wave-mixing signal strength. The use of potassium as an ionization suppressor and lower plasma power levels minimizes cesium ionization and maximizes atom population, resulting in a stronger wave-mixing signal.

Figure 9:
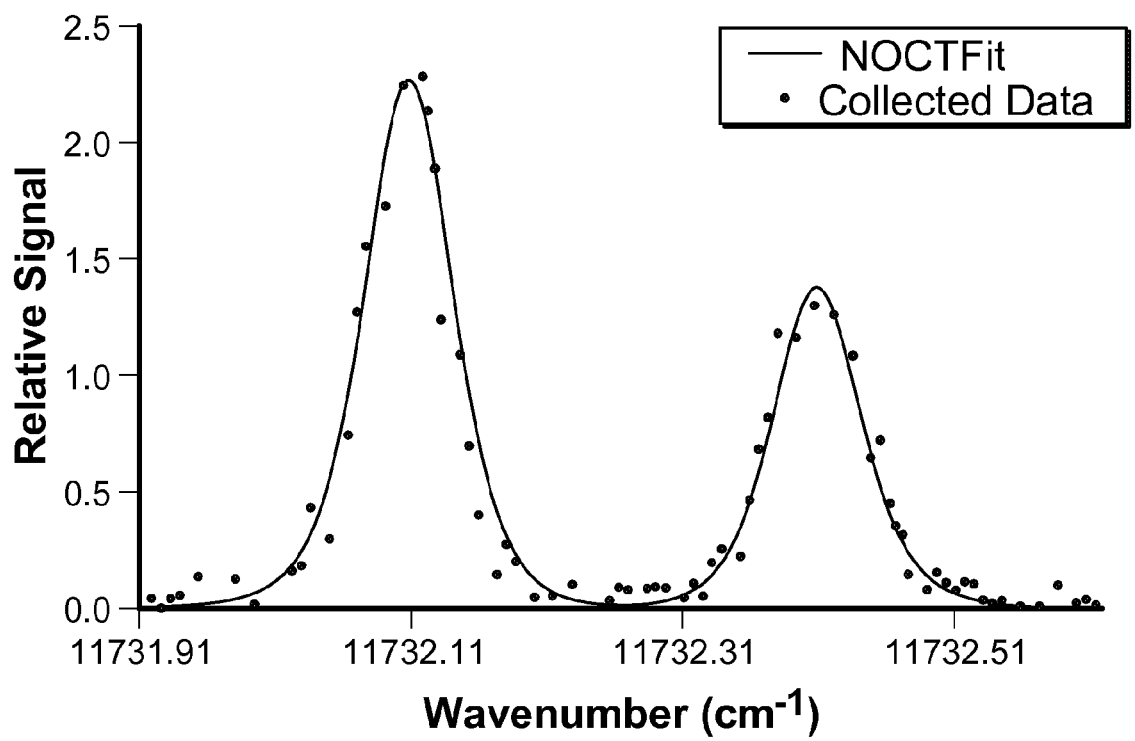
FIG. 9 shows an example of a hyperfine spectrum of cesium in the ICP. Experimental data shown as dots overlaid on the expected profile calculated by the nonlinear optical coherence theory (NOCT).

Comparisons of ICP and GF Atomizers. FIG. 9 shows a wave-mixing spectrum collected for a 1000 ppm Cs solution using the ICP atomizer. As expected, the ICP atomizer does not yield sensitivity levels as good as the graphite furnace, and hence, higher cesium concentration levels are used for these hyperfine measurements. Since the ICP is a continuously firing atomizer, one can collect the wave-mixing signal at a much higher sampling rate as compared to those for the graphite furnace. In FIG. 9, each data point represents the average of multiple signals collected over a 20 second window while the wavelength is kept constant. Although a detailed hyperfine scan in the graphite furnace takes longer, the scan shown in FIG. 9 takes fewer than 25 minutes in the ICP.

Experimental and theoretical hyperfine profile least-squares fittings indicate that the temperature inside the laser probe volume is approximately 3000 K for the ICP atomizer. As expected, this temperature is in the lower range available for an ICP plasma, since we use the coolest portion of the torch at the lowest RF power level possible. Similar temperatures have been reported for the argon-ICP atomizers (34, 35). Our least-squares fittings also yield an ICP pressure of 125 kPa, close to room pressure, as expected, from an unconfined ICP atomizer system.

The Cs hyperfine structure of the 2P3/2 state cannot be resolved, since the individual lines (150-250 MHz) are too close even for a sub-Doppler wave-mixing high-resolution method. However, one could use a low-pressure atomizer such as a hollow-cathode discharge to further minimize pressure broadening and enhance spectral resolution. With sub- Doppler resolution and minimum pressure broadening, one could resolve more crowded hyperfine profiles. Without more accurate measurements of shared transitions (hyperfine measurements) between these two levels, it is difficult to accurately determine the absolute frequency of the splitting between the ground-state levels. This is a possible reason for the slightly lower results determined for the fine splitting. Fine splitting for the ICP atomizer is calculated to be 9,143.6 MHz, slightly closer than the graphite furnace value, as compared to previously reported value at 9,193 MHz. Regardless, these values are well within the uncertainty of the averages used to measure the hyperfine splits.

The difference in line widths obtained using the ICP and the graphite furnace atomizers. By comparing FIG. 7 and FIG. 9, it is clear that the ICP scans produce peaks that are 20% narrower than those measured in the graphite furnace. The narrower ICP line widths are likely due to less collision with the argon buffer gas at higher cesium concentration levels, as compared to the ppt-level samples present in the graphite furnace. This effect has been reported for several systems including atomic oxygen spectra in the presence of argon in a discharge plasma cell (36).

The following sections provide various implementations of detection of biological and chemical substances in liquids using optical nonlinear wave mixing. Examples of a wave-mixing circular dichroism detector for chiral liquid chromatography are presented first.

A sensitive circular dichroism (CD) detector based on laser four-wave mixing is presented using separate injections of chemicals, enantiomers, onto a standard silica-based microbore high performance liquid chromatography (HPLC) separation column. Using the chiral HPLC column, a preliminary 'detected' mass detection limit of 180 pg is determined inside a laser probe volume of 200 pL, corresponding to a circular dichroism optical detection limit, $\Box A$, of $2.2\times10^{-5}$ for (−) camphorquinone. Detection sensitivity levels are dramatically improved when our forward wave-mixing circular dichroism detector is interfaced to a microbore system due to the lower mobile-phase flow rates and the smaller sample concentrations required for the analysis. Using the microbore HPLC column, a preliminary circular dichroism optical detection limit, $\Box A$, of $1.6\times10^{-6}$ and a preliminary concentration detection limit of $4.1\times10^{-4}$ M are determined for camphorquinone. This corresponds to a 'detected' mass detection limit of 33 pg for the chiral compound. Laser wave mixing offers better detection limits than conventional circular dichroism detection methods, and hence, offers many promising applications.

The present four-wave mixing-based circular dichroism (CD) detector offers orders of magnitude better detection sensitivity levels as compared to conventional non-laser-based or laser-based circular dichroism detectors. Wave-mixing CD detector can be interfaced to commonly available and widely popular microbore high performance liquid chromatography (HPLC) separation systems. The use of small laser detector probe volumes (200 pL) allows excellent 'detected' mass detection limits (180 pg) and significantly enhanced circular dichroism optical detection limits ($\Box A$ of $2.2\times10^{-5}$) for (−) camphorquinone. Detection sensitivity levels are dramatically improved when our forward wave-mixing circular dichroism (FWM-CD) detector is interfaced to a microbore system due to the lower mobile-phase flow rates and the smaller sample concentrations required for the analysis. Using the microbore HPLC column, a preliminary circular dichroism optical detection limit, $\Box A$, of $1.6\times10^{-6}$ and a preliminary concentration detection limit of $4.1\times10^{-4}$ M are determined for camphorquinone. This corresponds to a 'detected' mass detection limit of 33 pg for the chiral compound. Laser wave mixing offers better detection limits than conventional circular dichroism detection methods, and hence, offers many promising applications. Unique detection sensitivity advantages of wave-mixing CD detectors offer important applications in a wide range of fields previously thought impossible including those in pharmaceuticals, agrochemicals and biotechnology.

Currently available UV absorption detectors provide no information about the optical activity of the sample, and therefore, they do not compliment the selective nature of chiral HPLC. Conventional UV absorption detection methods do not allow characterization of detected molecules unless standards are available. Standards are often unavailable, especially with research involving original synthesis of new chiral compounds. Wave mixing allows effective combination of enantioselective HPLC with an enantioselective detector design.

For chiral-HPLC systems, refractive-index (RI) detections have been most commonly used for the determination of specific rotations of optically active samples. While RI detection methods are sufficient for some purposes, the technique suffers from problems related to sensitivity, selectivity and peak reproducibility. Wave mixing overcomes these limitations.

Unlike conventional "transmissive" CD methods, wave-mixing CD does not require specially designed flow cells with relatively long path lengths for efficient absorbance measurement. By using a square capillary attached to the end of the HPLC column, one can achieve significantly better CD AA detection limits in the low 10-6 range.

Enantioselective chemical analysis is becoming increasingly important in many facets of science, especially with respect to pharmaceuticals, agrochemicals and biotechnology. The importance of molecular stereochemistry has resulted in an enormous amount of research dealing with optically active compounds and analytical techniques for the resolution of enantiomers (1, 2). Chromatography has become an essential tool for the separation of enantiomers. There are numerous reviews (3, 4) that discuss the multitude of successful chiral separations and most of which employ high performance liquid chromatography (HPLC). Liquid chromatography is an attractive technique for chiral resolution due to its speed, high resolution, reproducibility and convenient applicability for molecules in solution. Furthermore, the flexibility of different HPLC mechanisms for enantiomer resolution allows for different molecules in various matrices to be separated based on the method best suited for that sample. Mechanisms of chiral HPLC separation can be divided into three general categories (5): (a) diastereomer formation, (b) chiral mobile phase complexing and (c) chiral stationary phase complexing (i.e., chiral columns). Over the past few years, it is the use of chiral stationary phases (CSP) that has had the greatest increase in use primarily due to the increased availability of CSPs and the ease of experimental implementation.

Although chiral HPLC as a separation technique has seen dramatic advancement and applications, detector technology for the method has many shortcomings, especially as the need for small sample volumes increases. Although UV absorption is the most widely used detection method for HPLC systems, it provides no information about the optical activity of the sample, and therefore, it does not compliment the selective nature of chiral HPLC. Conventional UV absorption detection methods do not allow characterization of detected molecules unless standards are available. Standards are often unavailable, especially with research involving original synthesis of new chiral compounds. Hence, the ideal system for chiral analysis would combine enantioselective HPLC with an enantioselective detector. For chiral-HPLC systems, refractive-index (RI) detections have been most commonly used for the determination of specific rotations of optically active samples. While RI detection methods are sufficient for some purposes, the technique suffers from problems related to sensitivity, selectivity and peak reproducibility.

One method that has become popular for chiral chemical analysis is circular dichroism (6). This technique measures the differential absorption of left and right circularly polarized light (CPL) of an optically active molecule. A molecule that has a certain "handedness" absorbs light that has a certain handedness, and the molecule absorbs differently than would a symmetric molecule. Circular dichroism (CD) has mostly been used for the analysis of samples in a "static" mode, i.e., the sample is stationary and confined to some type of sample container. The advancement of chiral HPLC has opened new opportunities for CD spectroscopy. It has been shown that CD can be used as an excellent detection method for HPLC (7) since it simultaneously yields both qualitative (peak sign) and quantitative (peak area) information about an eluting analyte. Selectivity is also enhanced because only the eluting analytes that absorb and those that are chiral can register a signal peak. Non-chiral and non-absorbing analytes are invisible to the detector. This allows simplification of chromatograms that consist of multiple chiral and non-chiral analytes and it is especially useful and effective when chemical impurities are high (8). Unlike polarimetric (i.e., dispersive) detection methods which have also been used as enantioselective detectors for HPLC, CD is sensitive to analyte absorption and, is thereby, a more selective detection method. Furthermore, the main advantage of CD detection over polarimetric devices for HPLC is its ability to directly determine the sample elution order without the need for standards in many cases (9).

In an alternative implementation, the two pump beams can be orthognally linearly polarized and one pump beam is modulated to change between the two orthogonally linear polarization states. As such, a method can be provided for using optical four wave mixing to detect circular dichroism of a sample material. This method includes operating a capillary cell to provide an analyte solution containing a sample material to be measured for circular dichroism; operating a pump laser to produce a pump laser beam at a pump laser wavelength; using optical components arranged to split the pump laser beam into a first pump beam in a first pump linear polarization and a second pump beam in a second pump linear polarization orthogonal to the first pump linear polarization in a four wave mixing configuration to overlap with each another at a location in the analyte solution at the capillary cell; operating a probe laser to produce a probe laser beam at a probe laser wavelength different from the pump laser wavelength; directing the probe laser beam to the location in the in the analyte solution at the capillary cell in a direction for the four wave mixing configuration where the probe laser beam, the overlapped first and second pump beams and a four wave mixing signal beam at the probe laser wavelength interact to convert energy from the first and second pump beams into the four wave mixing signal beam; modulating the first pump beam in the first pump linear polarization at a modulation frequency to be alternatively in the first pump linear polarization and in the second pump linear polarization; using an optical detector to receive light in a selected direction of the four wave mixing signal generated at the location in the analyte solution; and processing a detector output of the optical detector corresponding to the modulation frequency to measure different optical absorptions associated with the alternatively the first pump linear polarization and the second pump linear polarization and to determine circular dichroism of the sample material.

Although CD methods have been demonstrated in the past as useful HPLC detectors, there are problems associated with conventional CD detection methods. One fundamental problem for the conventional CD detection method, as with all absorption-based methods, is that it is a "transmissive" measurement, i.e., the signal is derived from measuring a small difference between two very large signals. Circular dichroism is measured by determining the difference between two absorption levels, one for right circularly polarized light (RCPL) and one for left circularly polarized light (LCPL). Optical absorption itself is a "difference" method, i.e., the ratio between the intensity of a beam of light before and after a sample. Hence, CD can be described as a "difference in a difference" or a "doubly transmissive" technique. Furthermore, CD signals are typically 2 to 3 orders of magnitude smaller than the absorption signal. Thus, transmissive CD detectors require a large dynamic range to effectively measure these small signals riding on very large background levels. Research towards the application of transmissive CD for detection in HPLC has mainly focused on increasing signal-to-noise ratios (S/N) by enhancing conventional instrumentation (10, 11), by introducing lasers as the light source (12, 13), or by developing unique CD methods (14). Fluorescence methods have also been developed (15) that yielded excellent detection sensitivity for analytes that fluoresce.

An optical detection method that is based on absorption, yet does not suffer from high background levels, is laser four-wave mixing (FWM). Four-wave mixing is a highly sensitive laser technique for measuring small absorbances in both gas and liquid analytes (16-19). It is a "dark background technique" because the signal is a coherent laser beam that propagates away from all input beams. The signal is present only if the analyte absorbs the excitation light. Hence, FWM is highly sensitive to weak optical absorptions and applicable to a wide array of samples and sample matrices, fluorescing or non-fluorescing analytes.

Specific examples of a FWM-CD optical detection device designed for sensitive chiral HPLC detection are provided below. We have investigated FWM as a unique method of measuring CD in various systems (20, 21) that use both continuous-wave and pulsed laser excitation sources to create both polarization and thermal gratings. Unlike transmissive CD methods, FWM-CD does not require specially designed flow cells with relatively long path lengths for efficient absorbance measurement. By using a square capillary attached to the end of the HPLC column, one can achieve AA detection limits in the low 10-6 range.

Wave mixing is uniquely and inherently effective when incorporating polarization modulated detection and signal-to-noise enhancement techniques. The polarization plane of the argon ion laser beams entering the sample is purified using three Glan-Thompson prism polarizers. One polarizer is placed near the laser head and one polarizer is used in each input beam path near the analyte cell. A Pockels cell is placed in one of the pump beams after the polarizer and it is driven by a variable frequency high-voltage waveform generator that is referenced to a lock-in amplifier for phase-sensitive detection of the signal. The linearly polarized laser beam entering the Pockels cell is converted into alternating left- and right-circularly polarized light (LCPL and RCPL) using a 100 Hz modulation frequency.

Figure 10:
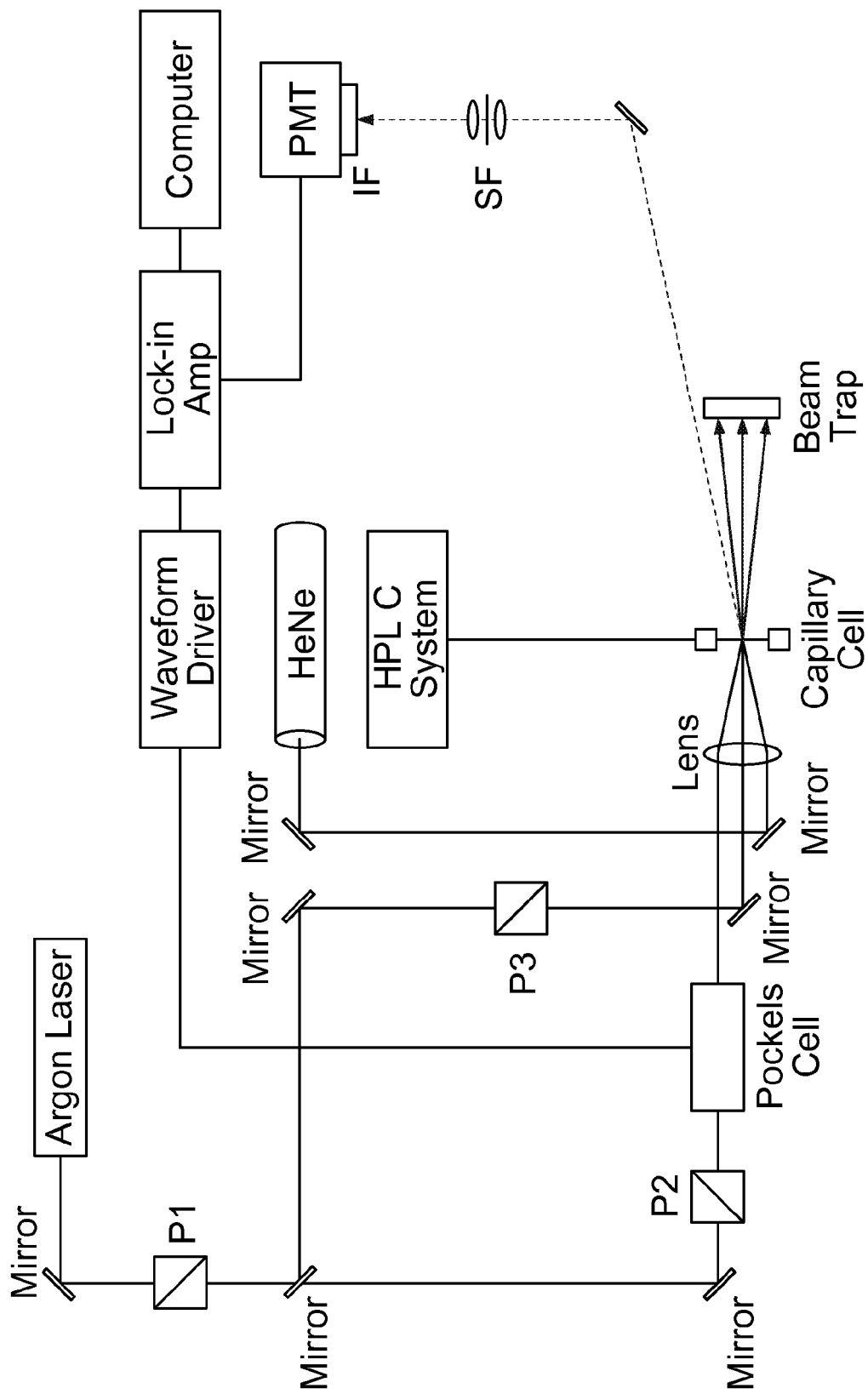
FIG. 10 shows an example of an optical detection device for four-wave mixing circular dichroism (FWM-CD) detection.

The optical arrangement for FWM-CD detection is shown in FIG. 10. The laser-induced gratings are formed by mixing two beams from an argon ion laser (Spectra Physics Model 171) operating at 474 nm. The laser output is split using a 50/50 beam splitter and recombined at the HPLC detector cell. The path length difference between the two beams is kept less than the coherence length of the argon ion laser (~5 cm) to maximize grating contrast. The polarization plane of the argon ion laser beams entering the sample is purified using three Glan-Thompson prism polarizers. One polarizer is placed near the laser head and one polarizer is used in each input beam path near the analyte cell. A Pockels cell (Lasermetrics, Model LMA-4) is placed in one of the pump beams after the polarizer and it is driven by a variable frequency high-voltage waveform generator that is referenced to a lock-in amplifier (Princeton Applied Research, Model 5702) for phase-sensitive detection of the signal. The linearly polarized laser beam entering the Pockels cell is converted into alternating left- and right-circularly polarized light (LCPL and RCPL) using 100 Hz modulation frequency.

A 1 mW He—Ne laser operating at 632 nm is used as the probe laser. All three input laser beams are focused on the analyte flow cell using a 10-cm focal length lens. The diameter of the focused beam spot is approximately 34 $\mu$m and the grating forming beams intersect in the sample cell with an angle of approximately 1°. The He—Ne laser probe beam is diffracted by the wave-mixing grating into two signal beams, one of which is directed though a blue color filter (for removing the pump laser light), a 100 $\mu$m spatial filter, a 632 nm laser line filter, and finally to a photomultiplier tube (Hamamatsu Corp., Model R928) for detection. The signal is sent to the lock-in amplifier and its output is recorded on an oscilloscope and a computer.

The chromatographic system consists of a piston pump (Pharmacia, LKB Model 2248) with a flow rate ranging from 10 $\mu$L/min. to 10 mL/min. and a solvent conditioner (Pharmacia, LKB Model 2156) for mobile phase degassing using He. A mobile phase consisting of 99% hexane and 1% 2-propanol is used. Two separate columns are used, one for enantiomer separation and one for microbore chromatography. Our chiral column (Chiral Technologies, Inc., Chiralpak AD) is an analytical type column (4.6 mm i.d., 25 cm long) and has an amylose carbamate derivative chiral stationary phase (10 $\mu$m particle size). The microbore column (1.0 mm i.d., 15 cm long) has a non-chiral silica stationary phase (Spherisorb Si, Phase Separations, Inc.). The detector cell is a 200 $\mu$m i.d. square-bore capillary tube (Wale Apparatus Co.) that is epoxied inside two pieces of PEEK tubing. The input end of the cell is attached to a zero dead volume connector which links the capillary cell to the end of the column. The laser probe volume is thus only approximately 3 cm from the column bed.

Figure 11:
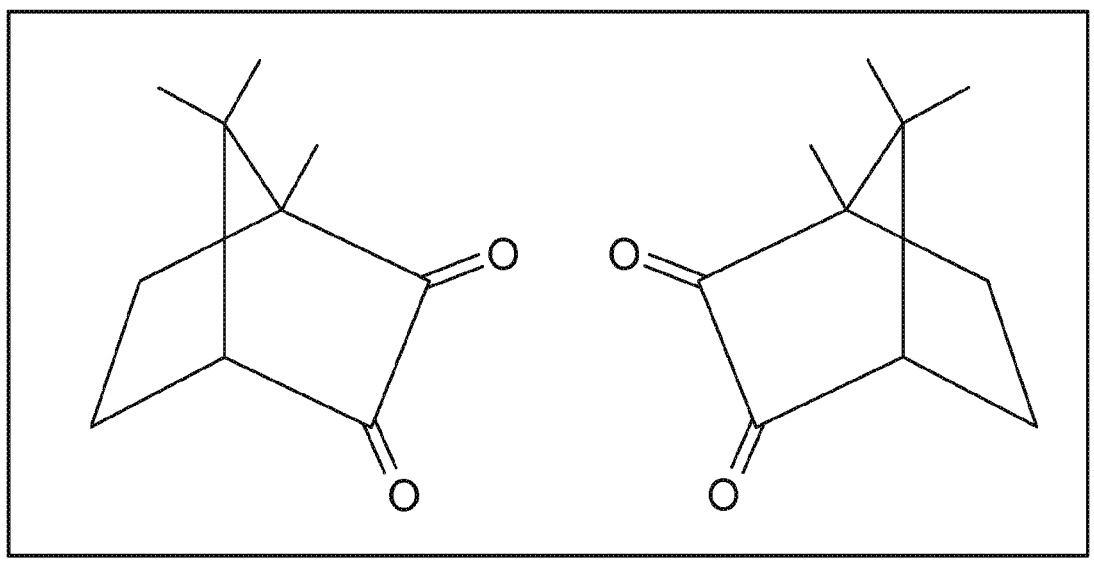
FIG. 11 illustrates an example of optically active (+) and (−) camphorquinone (CQ) used as analytes.

Injected samples consist of optically active (+) and (−) camphorquinone (CQ), as shown in FIG. 11 (Sigma Chemicals). Solutions of these enantiomers are prepared in the 99:1 hexane:2-propanol mobile phase, filtered (0.2 $\mu$m) and used immediately after preparation.

Conventional CD detectors measure a small difference between two intense light beams. Our wave-mixing CD detectors measure an absolute positive signal beam (a coherent laser-like beam) that has its own optical propagation direction, i.e., virtually no optical background noise and minimum interference problems.

The use of polarization modulation further enhances the wave-mixing S/N. The input laser beam that enters the Pockels cell is converted into alternating left- and right circularly polarized light (LCPL and RCPL) at a suitable modulation frequency. The signal that is proportional to analyte CD arises when an optically active analyte absorbs LCPL and RCPL differently, and hence, generating different levels of overall grating strengths for the different polarizations. The wave-mixing CD signal is then obtained based on the difference in the LCPL-induced wave-mixing signal and the RCPL-induced wave-mixing signal.

Figure 14:
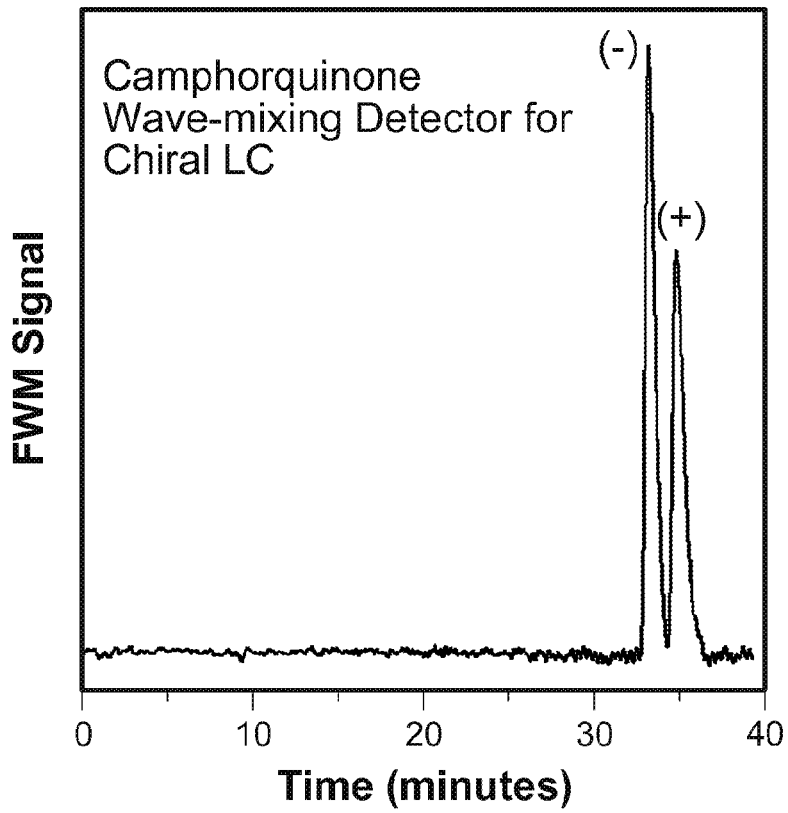
FIG. 14 shows an example of a chiral chromatogram with (−) and (+) camphorquinone enantiomers well resolved and detected by four-wave mixing (FWM).
Figure 15:
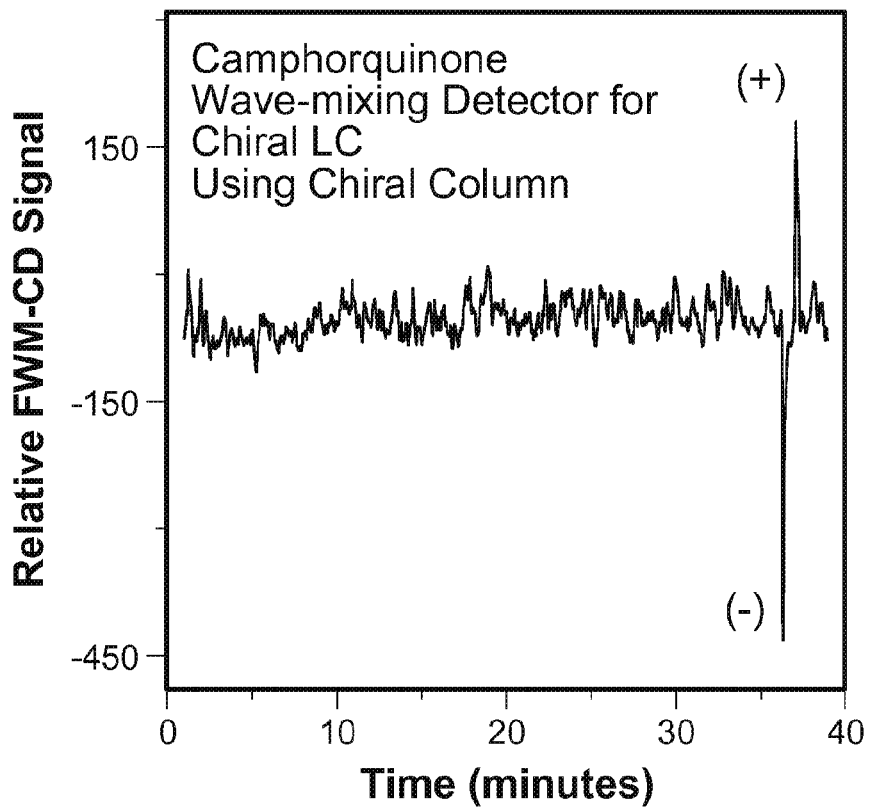
FIG. 15 shows an example of a chiral chromatogram with (−) camphorquinone (negative peak) and (+) camphorquinone (positive peak) detected by four-wave mixing circular dichroism (FWM-CD).

Unlike normal wave-mixing detection, the CD wave-mixing detection mode provides additional information on the chirality of the eluting analyte, and hence, yields better selectivity especially when multiple components of absorbing compounds and chiral compounds are present. As shown in FIG. 15, (−)camphorquinone elutes with a negative peak and (+)camphorquinone comes off the column about one minute later with a positive peak. The two chromatograms in FIG. 14 and FIG. 15 show that wave mixing and wave-mixing CD can be used effectively for chiral HPLC detection in a very small probe volume (200 pL).

Unlike all conventional "transmissive" CD detectors, wave-mixing CD yields strong signals even when using micrometer-short optical path lengths.

One of the wave-mixing CD advantages particularly relevant to HPLC chemical separation as compared to conventional "transmissive" CD methods is that wave-mixing CD is a "dark background" technique. A signal is generated only when an absorbing analyte is present in the laser probe volume. In addition, the generated coherent signal beam is spatially separated from all input beams with its own beam propagation direction. Hence, the signal is monitored at an angle from the strong input beams, yielding an almost dark-background detection technique with only a minimum background scattering from other optical components.

Wave mixing is inherently suitable for detection in ultra small probe volumes, and hence, it allows excellent interface to microbore separation chromatography, especially when using very slow flow rates.

The mechanisms for FWM-CD signal generation has been described previously in detail (16-21). A thermal grating is generated when two laser beams are crossed at a small angle inside an absorbing liquid. This temperature fluctuation results in a corresponding spatial modulation of analyte refractive index which scatters the probe beam. Wave-mixing circular dichroism measurements are made via (a) formation of the thermal gratings, (b) generation of the scattered coherent signal beam, (c) proper electro-optical polarization modulation of one of the input pump beams, and (d) appropriate demodulation of the output signal. The pump beam that enters the Pockels cell is converted into alternating left- and right circularly polarized light at a suitable modulation frequency. The signal that is proportional to analyte CD arises when an optically active analyte absorbs LCPL and RCPL differently, and hence, generating different levels of overall grating strengths for the different polarizations. The FWM-CD signal is then obtained based on the difference in the LCPL-induced wave-mixing signal and the RCPL-induced wave-mixing signal.

Experimentally it is difficult to generate 100% pure circularly polarized light. However, by careful alignment and control of a polarization modulation device, it is possible to maximize the purity. One of the most important procedures in FWM-CD detection is to ensure that the light polarization entering the Pockels cell is very pure. Hence, a Glan-Thompson prism polarizer is placed directly before the Pockels cell with the polarization axis aligned parallel with that of the electro optic crystal axis. The Pockels cell itself must be carefully positioned with respect to the laser beam, and mounted so that five degrees of freedom are available for precise and reproducible adjustment, i.e., horizontal and vertical translation, pitch and azimuth adjustments, and finally clockwise and counter-clockwise rotation of the crystal around the laser beam. Another variable that requires careful control is the applied modulation voltage. To modulate quarter-wave retardation of the 474 nm excitation light, the Pockels cell is switched between +1.46 kV and −1.46 kV by the variable frequency signal generator, causing the beam polarization to alternate between LCPL and RCPL. The frequency controller monitors the applied voltage for each cycle and it is necessary to confirm that these voltages are the same, since any offset in the applied voltage causes an artifact signal that either adds to or subtracts from a true CD signal (22). When all the parameters mentioned above are optimized, the system generates circular light with a purity level of better than 80% (i.e., ratio of minor and major axis of the polarization ellipse).

Figure 12:
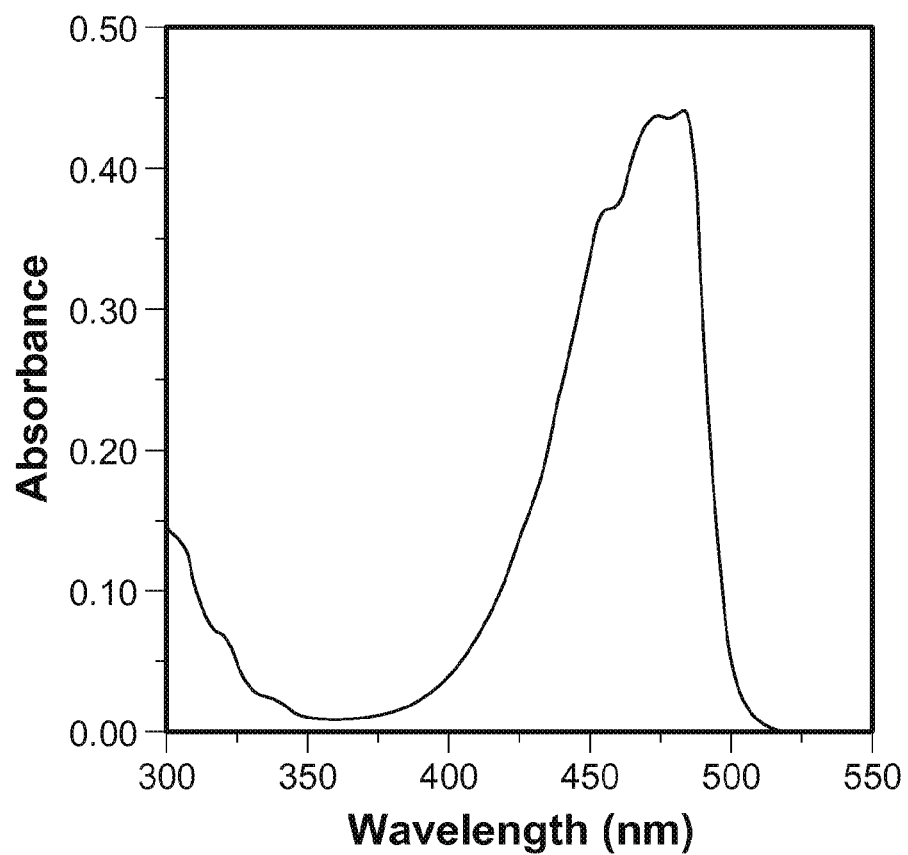
FIG. 12 shows an example of a conventional absorption spectrum of camphorquinone optical isomers.

The application of wave-mixing CD for enantioselective detection with chiral HPLC is demonstrated using camphorquinone optical isomers. Conventional optical absorption spectrum of camphorquinone is shown in FIG. 12. The excitation laser beams that form the laser-induced gratings in the sample have a wavelength of 474 nm, close to the maximum absorption of the sample. This maximizes the formation of thermal gratings that are produced via heating from radiationless relaxation of the light absorbing molecules. The probe laser beam has a wavelength of 632 nm, and therefore, it falls in a transparent region of the sample for absorption, fluorescence or phosphorescence (23). The use of a laser that probes the grating far outside of these interfering regions ensures that the only source of background noise at the detector is the scattering of the probe beam itself.

Figure 13:
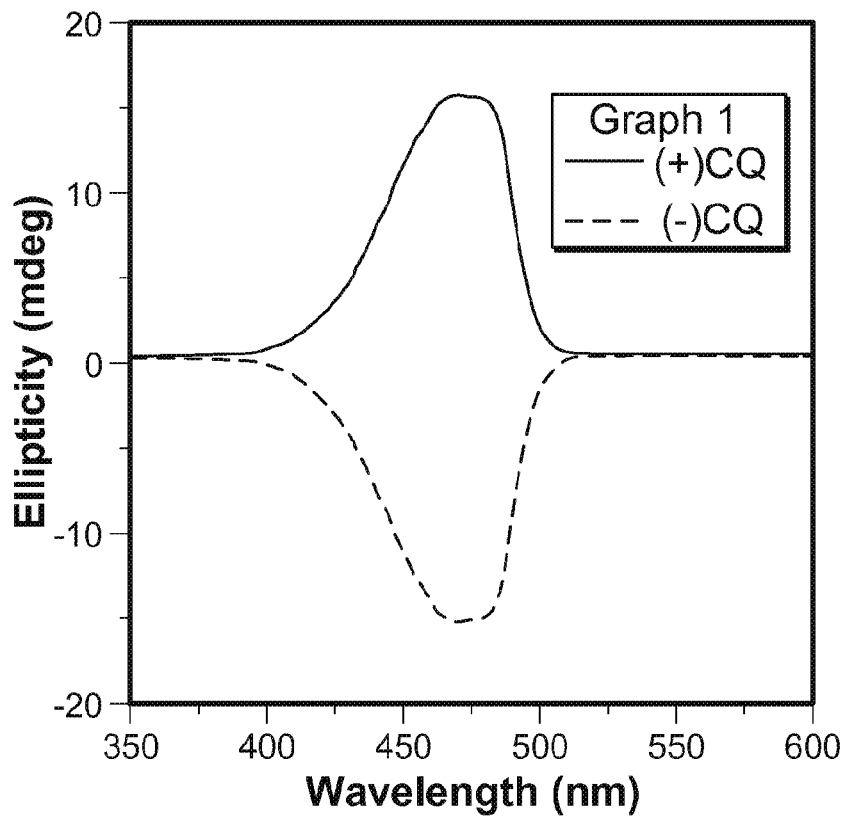
FIG. 13 shows an example of a conventional CD spectra of (+) and (−) camphorquinone enantiomers with equal but opposite peaks and ellipticity values.

FIG. 13 shows conventional CD spectra for (+) and (−) camphorquinone enantiomers, with equal but opposite peaks and ellipticity values of +/−15 mdeg, respectively. Like conventional optical absorption spectra, the CD band maxima for camphorquinone also falls near our laser excitation wavelength.

The enantiomeric separation is performed using normal phase HPLC on a chiral column which has a bonded amylose based chiral stationary phase. Separation of a camphorquinone racemic mixture into (+) and (−) enantiomers is first performed using normal wave-mixing detection (i.e., no polarization modulation). In this case, a mechanical chopper is used instead for amplitude modulation of the signal. The chopper is referenced to the lock-in amplifier at 100 Hz. FIG. 14 shows the chiral chromatogram with (−) and (+) camphorquinone enantiomers well resolved under the conditions used (250 □L/min, 99:1 hexane/2-propanol mobile phase).

With the chiral separation verified using normal wave-mixing detection, the experimental setup is then modified for FWM-CD detection. Polarization modulation is performed at 100 Hz and the HPLC conditions are kept the same as those used for the data shown in FIG. 14. The chromatogram shown in FIG. 15 is for an injection of a racemic mixture of camphorquinone at a concentration of 1×10-2 M. Unlike normal wave-mixing detection, the CD wave-mixing detection mode provides additional information on the chirality of the eluting analyte, and hence, yields better selectivity especially when multiple components of absorbing compounds and chiral compounds are present. As shown in FIG. 15, (−) camphorquinone elutes with a negative peak and (+) camphorquinone comes off the column about one minute later with a positive peak. The two chromatograms in FIGS. 5 and 6 show that FWM and FWM-CD can be used effectively for chiral HPLC detection in a very small probe volume (200 pL). Unlike all conventional transmissive CD methods, FWM-CD yields strong signals even when using micrometer-short optical path lengths.

One FWM-CD advantage that is particularly relevant to HPLC as compared to conventional transmissive CD methods is that FWM-CD is a "dark background" technique. A signal is generated only when an absorbing analyte is present in the laser probe volume. In addition, the generated coherent signal beam is spatially separated from all input beams with its own beam propagation direction. Hence, the signal is monitored at an angle from the strong input beams, yielding an almost dark-background detection technique with only a minimum background scattering from other optical components. The optical background noise level is much lower than those of conventional CD methods where the signal is monitored along the same direction as the input beam. Conventional CD spectropolarimetric methods typically have detection sensitivity levels that are poor, partly because of their reliance on the measurement of a small difference in two large "transmitted" intensities when the absorbance of a RCPL beam (or a LCPL beam) is determined.

In nonlinear FWM-CD, the absorbance signal for a RCPL beam (or a LCPL beam) is determined by measuring a "positive" signal intensity of a sharp coherent laser-like signal beam, against a virtually dark background. Background signal is not present during the chromatogram, except when an analyte elutes. This unique feature is especially useful when collecting long chromatograms since it helps minimize baseline drifts. In conventional CD methods, there is always light at the detector, so a background signal level is always present. Any variation in the light intensity could register a change in the overall dc signal level. This is not an issue with FWM-CD because the coherent signal beam is present only when the analyte is present and it propagates at an angle away from the pump and probe beams, allowing effective suppression of source-light-induced background scattering.

Figure 16:
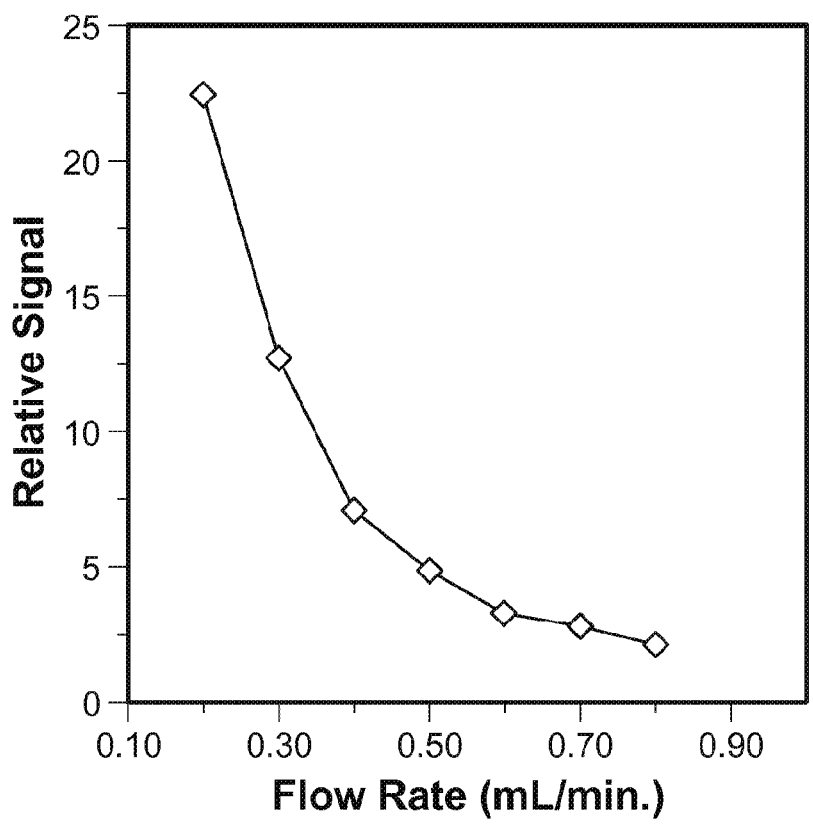
FIG. 16. Four-wave mixing circular dichroism (FWM-CD) signal is very strong at lower flow rates that are suitable for microbore or capillary chromatography.

Four-wave mixing is inherently suitable for detection in ultra small probe volumes, and hence, a FWM detector allows excellent interface to microbore chromatography. Microbore HPLC columns offer enhanced mass sensitivity levels and decreased solvent consumption compared to conventional analytical columns. Microbore or capillary chromatography is also more suitable for FWM detection, since the flow rates involved are much lower and well within the optimum range for FWM detection as shown in FIG. 16. Attenuation of a FWM signal at high flow or turbulence (which occurs more with continuous wave laser-excited FWM) is primarily caused by the diffusion processes that "wash out" the thermal grating inside the probe volume. When the flow rate increases, the thermal grating does not have sufficient time to reach its steady-state efficiency (24, 25). Microbore chromatography is commonly performed at very slow flow rates and requires detection in very small probe volumes. Therefore, a FWM detector is ideal for this type of separation method and chiral microbore columns are increasingly more widely available.

The FWM-CD detection system is demonstrated using separate injections of the analyte enantiomers onto a standard silica-based microbore column. Using the chiral column, a preliminary 'detected' mass detection limit of 180 pg is determined in a laser probe volume of 200 pL, corresponding to a CD detection limit, □A, of 2.2×10-5 for (−) camphorquinone. Detection sensitivity levels are dramatically improved when the FWM-CD detector is interfaced to the microbore system due to the lower mobile phase flow rates and the smaller sample concentrations required for the analysis. Using the microbore column, a preliminary CD detection limit, □A, of 1.6×10-6 and a preliminary concentration detection limit of 4.1×10-4 M (at S/N=2) are determined for camphorquinone. This corresponds to a 'detected' mass detection limit of 33 pg for the chiral compound.

The FWM-CD detector offers excellent detection sensitivity even when using very short sample path lengths (micrometer range). Furthermore, while the conventional CD signal has a "linear" dependence on $\Delta\epsilon$, the FWM-CD coherent signal beam intensity has a quadratic dependence on molar absorptivity. In addition, since the FWM-CD signal has a cubic dependence on excitation laser power, high photon density available from a laser can be efficiently used. Demand for sensitive analytical techniques for chiral molecules will continue to increase over the next decade, especially as the movement towards enantiomeric drugs proceeds (26). The FWM-CD detection method offers a wide range of potential applications since the detection sensitivity is excellent both for fluorescing and non fluorescing analytes even when using micrometer-level optical absorption path lengths. Possible future improvements include the use of ps pulsed lasers with adequate coherence lengths to take advantage of stronger transient gratings and the use of photoelastic and other polarization modulators to further enhance S/N.

In another aspect, a forward-scattering wave-mixing optical method is presented as an unusually sensitive "absorption-based" detector for liquid chromatography that offers good sensitivity, some inherent enhancement on peak resolution, small sample requirements and ease of use. Inside the analyte solution, the two input beams from the same laser source form thermally-induced refractive-index spatial gratings that in turn generate the forward-scattering wave-mixing signal. The intensity of the signal depends on input laser power, analyte properties such as absorption coefficient and concentration, and solvent properties such as refractive index/temperature coefficients. A common high performance liquid chromatography (HPLC) system is used to separate two important isomers in carotenoids, $\alpha$-carotene and $\beta$-carotene. The resolution of $\alpha$-carotene and $\beta$-carotene peaks detected by wave mixing is inherently better as compared to those detected by UV-visible absorption detectors. The peaks detected by wave mixing yield squared Gaussian profiles as compared to normal Gaussian profiles observed in UV-visible absorption detection. Using a probe volume of 113 pL, preliminary injected and detected $\beta$-carotene detection limits of 13 femtomoles and 1.47 attomoles, respectively, are determined. The wave-mixing signal has a quadratic dependence on absorption coefficient or analyte concentration, and hence, it offers some inherent peak resolution enhancement for $\alpha$-carotene and $\beta$-carotene. The signal also has a cubic dependence on input laser power, and therefore, the laser power is utilized very efficiently and one could use compact low-power lasers. The wave-mixing detection method is applicable to a wider range of analytes since it is based on optical absorption, not fluorescence, and it offers orders of magnitude better detection sensitivity levels as compared to those of conventional optical absorption detectors. Since the two input beams can be crossed or mixed inside a small probe volume, the detector probe volume can be very small. Based on these inherent properties and unique nonlinear features, this nonlinear optical detection method promises important advantages for a wide range of potential applications.

In the following sections, a novel forward-scattering wave-mixing optical method is presented as an unusually sensitive "absorption-based" detector for capillary-based separation methods, including liquid chromatography, that offer good sensitivity, some inherent enhancement on peak resolution, small sample requirements and ease of use. Wave mixing detection and separation resolution of similar chemicals, $\alpha$-carotene and $\beta$-carotene, are inherently better as compared to those detected by UV-visible absorption detectors. The peaks detected by wave mixing yield squared Gaussian profiles as compared to normal Gaussian profiles observed by UV-visible absorption detectors. The wave-mixing signal has a quadratic dependence on absorption coefficient or analyte concentration, and hence, it offers some inherent peak resolution enhancement for $\alpha$-carotene and $\beta$-carotene. The wave-mixing signal also has a cubic dependence on input laser power, and therefore, the laser power is utilized very efficiently, and one could use compact low-power lasers. The wave-mixing detection method is applicable to a wider range of analytes since it is based on optical absorption, not fluorescence, and it offers orders of magnitude better detection sensitivity levels as compared to those of conventional optical absorption detectors. Wave mixing offers unique advantages for detection and separation for a wide range of analytes including amino acids, proteins, nucleic acids, carbohydrates, drugs, metal-organic species and inorganic species for many applications. Wave-mixing advantages include excellent detection sensitivity levels, wide linear dynamic ranges, small sample requirements, low dead volume, ease of use, non-destructive analyses, and effectiveness for both fluorescing and non-fluorescing analytes while using micrometer-level absorption path lengths.

Wave mixing offers effective and reliable separation and detection of similar biomolecules, including but not limited to active carotenoids, $\alpha$-carotene and $\beta$-carotene, metabolic precursors of vitamin A that are essential for vision, cellular differentiation and embryological development. The antioxidant properties of carotenoids are thought to be responsible in part for human health protecting characteristics such as an enhanced immune response, inhibition of carcinogenesis and lowered incidence of cardiovascular disease. Because of their important role in nutrition and disease prevention, efficient separation and detection methods of these compounds at trace-concentration levels are needed for a wide range of applications.

While conventional UV-visible absorption peaks follow normal Gaussian profiles, the wave-mixing peaks yield squared Gaussian profiles. At the same peak height, the non-linear wave-mixing peaks are narrower than conventional UV-visible absorbance peaks, and hence, wave mixing offers inherently higher separation peak resolution.

High performance liquid chromatography (HPLC) offers powerful chemical separation capabilities for a wide range of analytes including amino acids, proteins, nucleic acids, carbohydrates, drugs, metal-organic species and inorganic species for many applications (1). With the increasing need for trace-concentration detection of more complex matrices, various improvements on HPLC detection techniques are needed. To take full advantage of the separation power of a HPLC system, one needs a detection system as powerful with desirable features such as good detection sensitivity, wide linear dynamic ranges, small sample requirements, low dead volume, ease of use and non-destructive analysis. Conventional UV-visible absorption detectors commonly used in HPLC offer good linearity, however, they offer poor concentration detection sensitivity levels and require relatively long optical absorption path lengths. Laser-induced fluorescence detection methods offer better detection sensitivity levels, however, they are applicable only for analytes that can fluoresce or can be labeled with fluorescing tags that require more time consuming steps. Detection methods based on nonlinear laser wave mixing offer excellent detection sensitivity levels and better separation efficiency for both fluorescing and non-fluorescing analytes while using micrometer-level absorption path lengths.

In a forward-scattering wave-mixing detection setup, two coherent input beams from the same laser are focused and mixed inside an absorbing analyte flowing through the capillary detector cell. The resulting thermal gratings scatter off a third beam from one of the input beams to generate a coherent signal beam. The wave-mixing signal has important characteristics including a cubic dependence on laser power, a quadratic dependence on analyte absorption coefficient and a quadratic dependence on the solvent refractive-index temperature coefficient (dn/dT). The signal is a collimated coherent light beam, and hence, signal collection efficiency is virtually 100%, a vast improvement over those of conventional optical methods such as fluorescence. The signal beam is visible to the naked eye, and hence, optical alignment is very simple and convenient. The laser-like properties of the signal also allow the use of highly efficient noise suppression and signal-to-noise (S/N) enhancement techniques that employ polarizers and spatial filters.

Unique characteristics of the nonlinear signal beam allow this wave-mixing technique to offer important advantages in various applications for both gas-phase and condensed-phase analytes. Using backward-scattering four-wave mixing optical configurations for gas-phase analytes, we have obtained sub-Doppler spectral resolution that is suitable for hyperfine structure measurements and isotope ratio analyses in a few different atomizers including hollow-cathode discharge plasmas, analytical flames and graphite furnace atomizers (2-8). For liquid analytes in continuously flowing cells, we have reported attomole-level detection sensitivity levels (9) that are comparable to those of laser-induced fluorescence methods while still offering detectability for both fluorescing and non-fluorescing analytes. In addition, we have used wave-mixing techniques to measure circular dichroism and optical rotation for chiral molecules (7, 8, 10). We have also demonstrated excellent detection sensitivity levels for wave-mixing detection of liquid analytes using low-power, compact, inexpensive diode lasers (11).

The following sections describe separation and detection of two of the most prevalent and active carotenoids, α-carotene and β-carotene, using capillary-column HPLC coupled with wave-mixing detection. α-Carotene and β-carotene are metabolic precursors of vitamin A which is essential for vision, cellular differentiation and embryological development.

Figure 17:
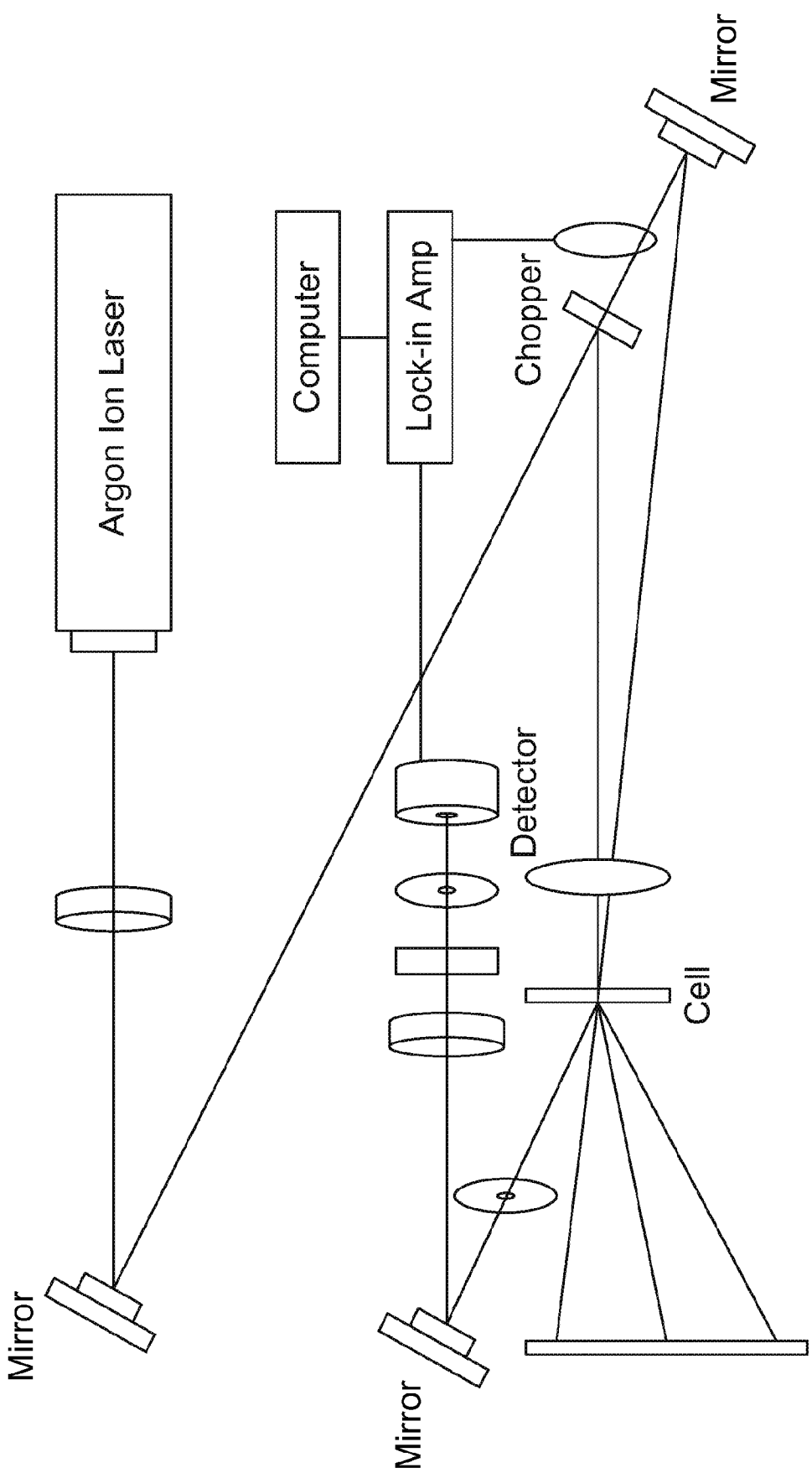
FIG. 17 shows an example of an optical detection device based on a nonlinear laser wave-mixing optical design.

As shown in FIG. 17, α-carotene and β-carotene are primarily C40 polyisoprenoid compounds that have an extensive conjugated double-bond system leading to a strong absorption of UV-visible light. In addition, the conjugated double-bond system enables these compounds to quench singlet oxygen and free radicals. The antioxidant properties of carotenoids are thought to be responsible in part for human health protecting characteristics such as an enhanced immune response, inhibition of carcinogenesis and lowered incidence of cardiovascular disease (12). Because of their important role in nutrition and disease prevention, efficient separation and detection methods of these compounds at trace-concentration levels are needed for a wide range of applications.

In this report, a preliminary injected detection limit of 13 femtomoles is determined for β-carotene using an injected volume of 1 μL and a preliminary detected mass detection limit of 1.47 attomoles is determined using a probe volume of 113 pL. Furthermore, HPLC peak profiles detected by wave mixing are compared to those detected by UV-visible absorption detection. While conventional UV-visible absorption peaks follow normal Gaussian profiles, the wave-mixing peaks yield squared Gaussian profiles, as expected. At the same peak height, the nonlinear wave-mixing peaks are narrower than conventional UV-visible absorbance peaks, and hence, wave mixing offers inherently higher peak resolution.

Unlike conventional "optical absorption" and "refractive-index" detectors widely used for HPLC, wave-mixing detectors do not require long optical path lengths (e.g., 1 cm). Excellent detection sensitivity levels can be obtained by wave mixing even when using path lengths that are orders of magnitude thinner (e.g., 0.05 mm).

Figure 18:
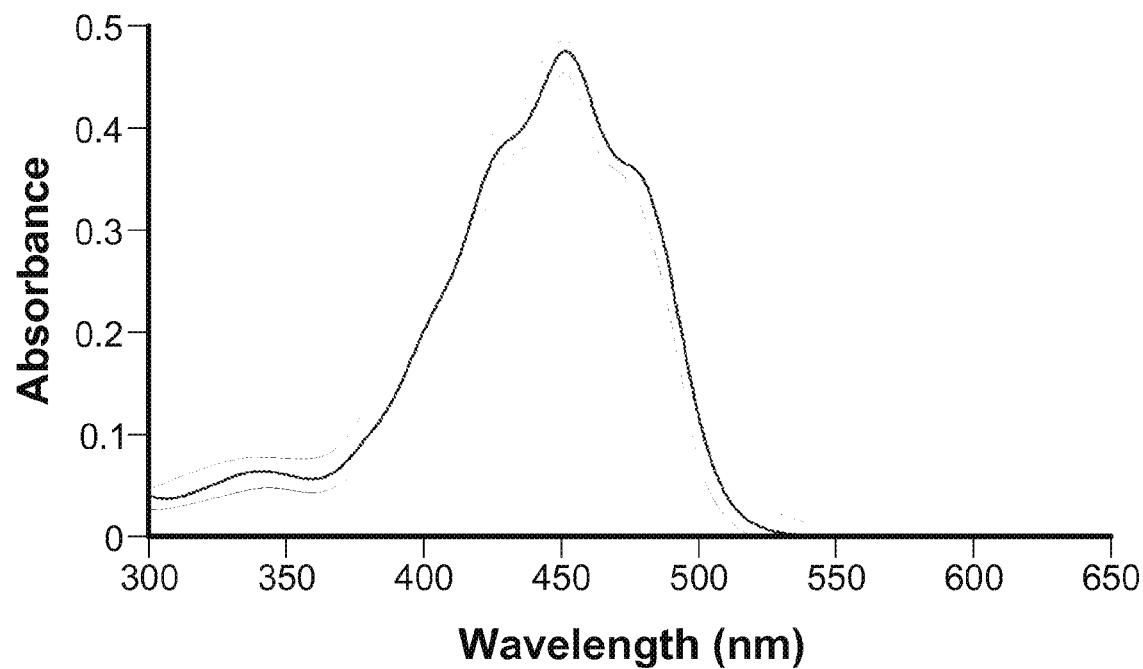
FIG. 18 shows an example of UV-visible absorption spectra of □-carotene and □-carotene components.

As shown in FIG. 18, the wave-mixing optical arrangement used here is similar to those described in our previous reports (9-11). A continuous-wave argon ion laser (454.5 nm) is filtered by a polarizer and then split by a beam splitter (30/70 R/T) to form the two input excitation beams. A single 10-cm focusing lens is then used to focus both input beams on a square capillary cell (0.2 mm path length). The laser power measured at the capillary cell is 25 mW. The diameter of the focused beam spot on the capillary cell is 13.4 μm, corresponding to a probe volume of 113 pL. The capillary cell is mounted inside a custom-built holder which in turn is mounted on a XYZ stage for precise optical alignment. An aperture is placed right after the sample cell to allow only the signal beam to pass through. The wave-mixing signal beam is then focused on a detector after passing through a polarizer, a pinhole and a high pass band filter. The output signal is amplified by a lock-in amplifier (Stanford Research Systems, Inc., Sunnyvale, Calif., Model SR810 DSP) which is referenced to a mechanical chopper modulating the probe beam at 200 Hz. A personal computer is used to digitize, collect and process the signal.

Figure 19:
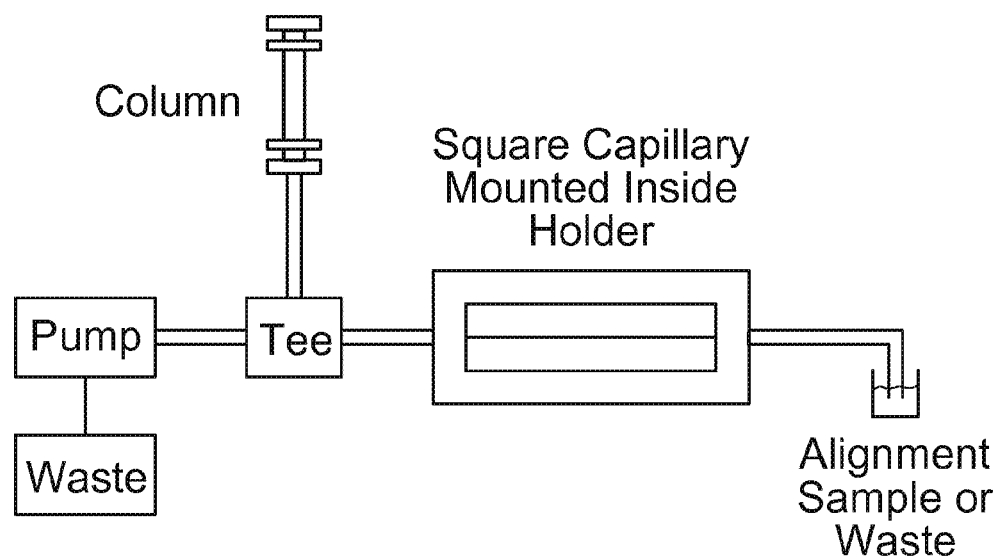
FIG. 19 shows an example of a wave-mixing detector cell and the alignment solution delivery system.

In this wave-mixing detection setup, a specially designed square capillary detector cell is used in order to minimize dead volume and simplify signal alignment procedures. FIG. 19 shows the detector cell and the alignment solution delivery system. The cell consists of a 0.2 mm square-bore capillary tube attached inside two pieces of polyvinyl chloride tubing. The capillary cell is connected to a zero dead volume tee connector which in turn is attached to the HPLC column. This tee connector allows direct connection of the cell to a peristaltic pump without the need to disconnect it from the HPLC system. Before a chromatographic run, the analyte cell is filled with an alignment solution using the peristaltic pump and then the optical alignment is optimized. After the wave-mixing signal is properly aligned and monitored by the detector, the flow is switched from the peristaltic pump to the HPLC system and the separation process is initiated.

The HPLC system consists of a pump (Pharmacia, LKB, Model 2248) with a flow rate range from 0.01 mL/min to 10 mL/min, a LC controller (Pharmacia, LKB, Model 2252) and a solvent conditioner (Pharmacia, LKB, Model 2156). The injector has a 1 μL sample loop. The HPLC column is a Zobax reversed-phase C18 capillary column (Microtechnology, Inc., San Jose, Calif., 0.32 mm i.d., 15 cm long). The mobile phase is a 48:40:12 (v/v/v) mixture of acetonitrile, methanol and methylene chloride and the mobile phase flow rate is 0.01 mL/min.

Stock solutions for α- and β-carotene are prepared by dissolving solid α- and β-carotene samples (Sigma, St. Louis, Mo.) in methylene chloride. The desired α- and β-carotene concentrations are then obtained by serial dilution in the mobile phase. All solutions are filtered through a 0.2-□m Nylon membrane syringe filter (Phenomenex, Torrance, Calif.) and degassed prior to use.

Figure 20:
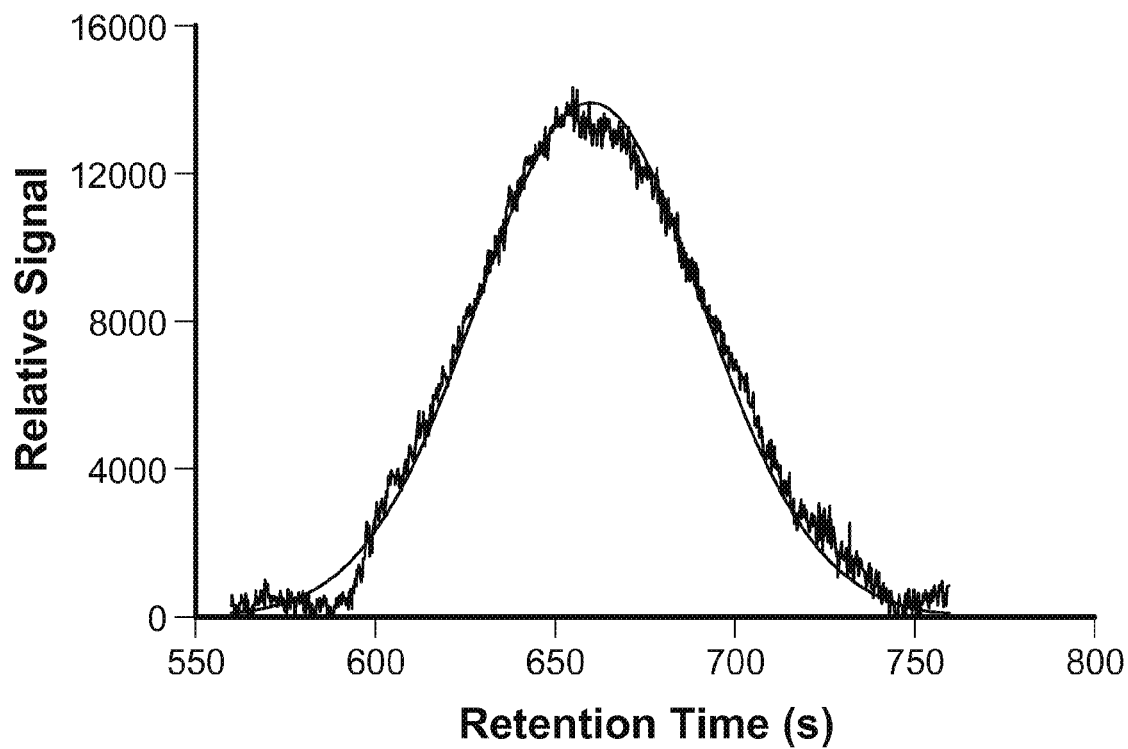
FIG. 20 shows an example of comparison of a simulated squared Gaussian peak and an experimental wave-mixing peak collected for $8.20 \times 10^{-7}$ M □-carotene.
Figure 21:
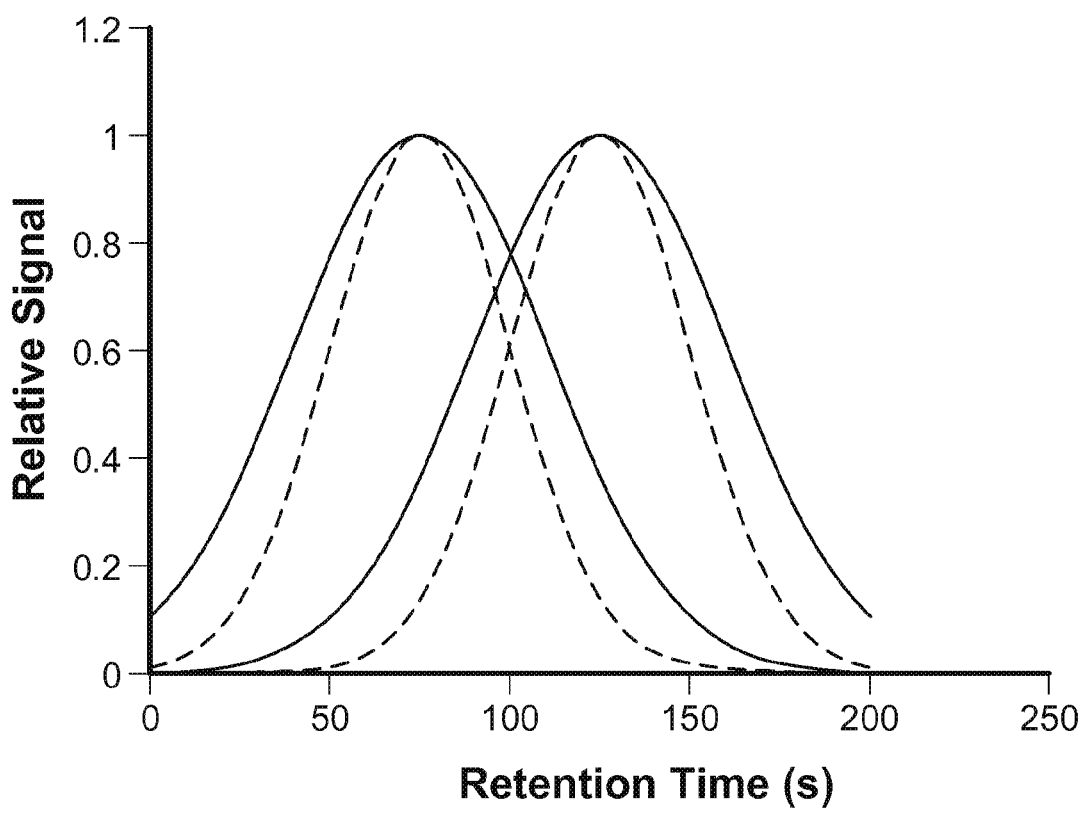
FIG. 21 shows an example of the resolution enhancement of a pair of squared Gaussian peaks compared to a pair of normal Gaussian peaks with identical retention times.

Since the nonlinear wave-mixing signal has a squared dependence on analyte concentration, the theoretical wave-mixing peak profile, i.e., a squared Gaussian profile, matches our experimental peak profile for β-carotene (FIG. 20). FIG. 21 shows two pairs of simulated unresolved peaks that follow normal Gaussian profiles and squared Gaussian profiles. At the same peak height, the squared Gaussian peaks are narrower than the normal Gaussian peaks, as expected. Hence, under identical HPLC separation conditions and identical retention times, the overlap of two squared Gaussian peaks is less than that of two normal Gaussian peaks. Therefore, wave mixing offers an inherently higher peak separation resolution under the same HPLC conditions.

Wave mixing is an optical absorption detection method. Compared to other absorption-based detection methods, wave mixing offers orders of magnitude better detection sensitivity levels, i.e., an "injected" concentration detection limit of 1.3×10-8 M for β-carotene (S/N of 2), an "injected" mass detection limit of 13 femtomoles, and a "detected" mass detection limit of 1.47 attomoles. The wave-mixing detection sensitivity, especially the mass detection sensitivity, is better or comparable to those previously reported using conventional absorption or fluorescence detectors for carotenoids separated by HPLC.

Our wave-mixing detector offers fluorescence-like detection sensitivity in a HPLC system, and yet, it can be used to detect a wider range of analytes including fluorescing and non-fluorescing molecules. Hence, this nonlinear absorption-based wave-mixing technique offers many potential advantages for sensitive analyses of biochemical and biomedical systems in a wide range of applications.

The wave-mixing signal can be described using the following equation $$I = k\left(\frac{b}{8\pi}\right)^2 I_{laser}^3 \frac{\lambda^2}{\sin^4[\theta/2]}\left(\frac{dn}{dT}\right)^2 \frac{\alpha^2}{K^2} \quad (1)$$

where I is the signal beam intensity, k is a constant, b is the sample thickness, Ilaser is the total input laser intensity, λ is the excitation wavelength, θ is the wave-mixing angle, dn/dT is the temperature coefficient of the refractive index, α is the absorption coefficient of the nonlinear medium, and K is the thermal conductivity. The signal has a cubic dependence on input laser power as shown in the equation. In order to have a good signal-to-noise ratio (S/N), the input laser power is optimized. When the laser power is increased to 40 mW, the signal intensity reaches a saturation level and the S/N is maximized. The laser power distribution between the pump and the probe input beams is also important. If both signal beams are needed, a 50:50 input intensity distribution is used to generate two equally intense signal beams. If only one strong signal beam is desired, the pump beam is made stronger than the probe beam using a distribution ratio of 70:30.

In order to further enhance the S/N, a mechanical chopper and a lock-in amplifier are used. The pump beam is usually not modulated by the chopper because (a) it is stronger, and hence, produces stronger background scattering noise, and (b) its propagation direction is closer to that of the signal beam than that of the probe beam. The signal is stronger at low modulation frequencies (e.g., 150 Hz) because of lower disturbance for the thermal gratings formed in the analyte, however, the background noise is higher at low modulation frequencies. The S/N is reasonably good at higher modulation frequencies. Since the lock-in amplifier has a built-in noise filter (sync filter) operating at a frequency lower than 200 Hz, we use a modulation frequency of 200 Hz, and a good separation of α- and β-carotene and excellent detection limits of β-carotene are achieved.

FIG. 20 shows comparison of a β-carotene peak experimentally collected by wave-mixing detection and a simulated squared Gaussian profile. Since the nonlinear wave-mixing signal has a squared dependence on analyte concentration as described in Equation 1, the theoretical wave-mixing peak profile, i.e., a squared Gaussian profile, matches our experimental peak profile for β-carotene, as expected.

FIG. 21 shows two pairs of simulated unresolved peaks that follow normal Gaussian profiles and squared Gaussian profiles. At the same peak height, the squared Gaussian peaks are narrower than the normal Gaussian peaks, as expected. Hence, under identical HPLC separation conditions and identical retention times, the overlap of two squared Gaussian peaks is less than that of two normal Gaussian peaks. Therefore, wave mixing offers an inherently higher peak separation resolution under the same HPLC conditions.

Figure 22:
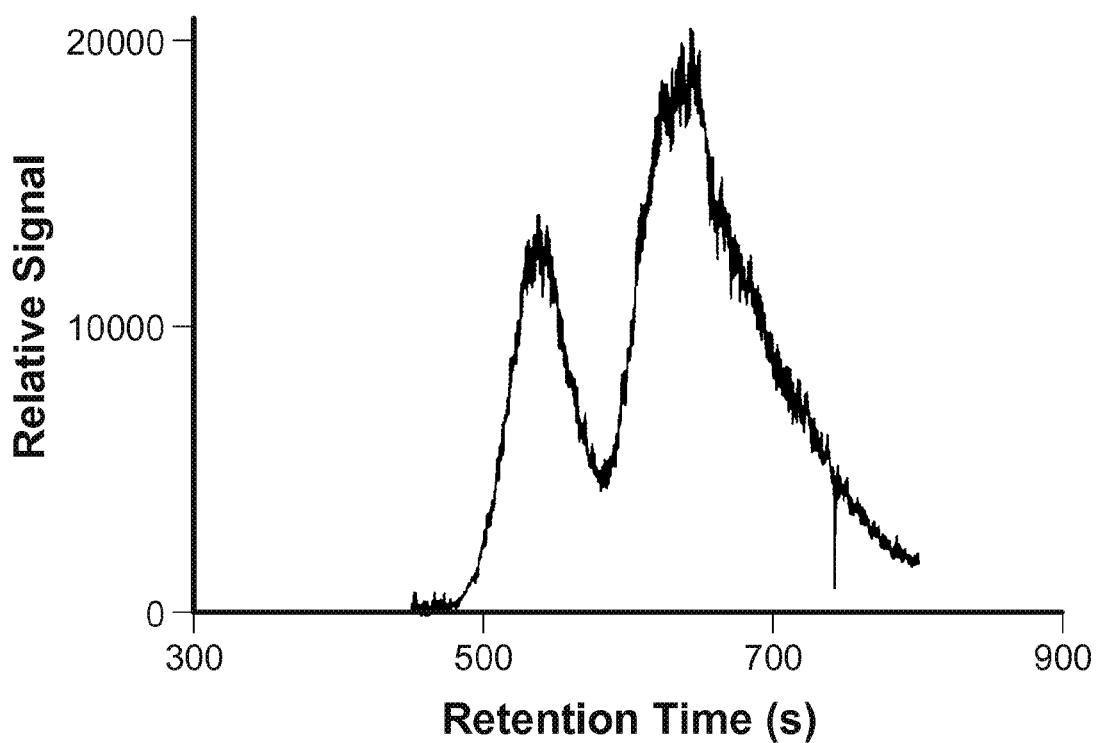
FIG. 22 shows an example of measured chromatogram of □-carotene and □-carotene detected by wave-mixing detection. Concentration of □-carotene and □-carotene used are $2.42 \times 10^{-6}$ M and $4.10 \times 10^{-6}$ M, respectively.

FIG. 22 shows a chromatogram of a mixture of 2.42×10-6 M α-carotene and 4.10×10-6 M β-carotene detected by wave mixing. The amounts of α-carotene and β-carotene injected into the capillary column are 2.42 picomoles and 4.10 picomoles, respectively. Compared to chromatograms detected by UV-visible absorption detection methods and other conventional laser-based or nonlaser-based HPLC detection methods, the nonlinear wave-mixing detection method offers intrinsically enhanced separation resolution when using identical HPLC separation conditions as described above.

Figure 23:
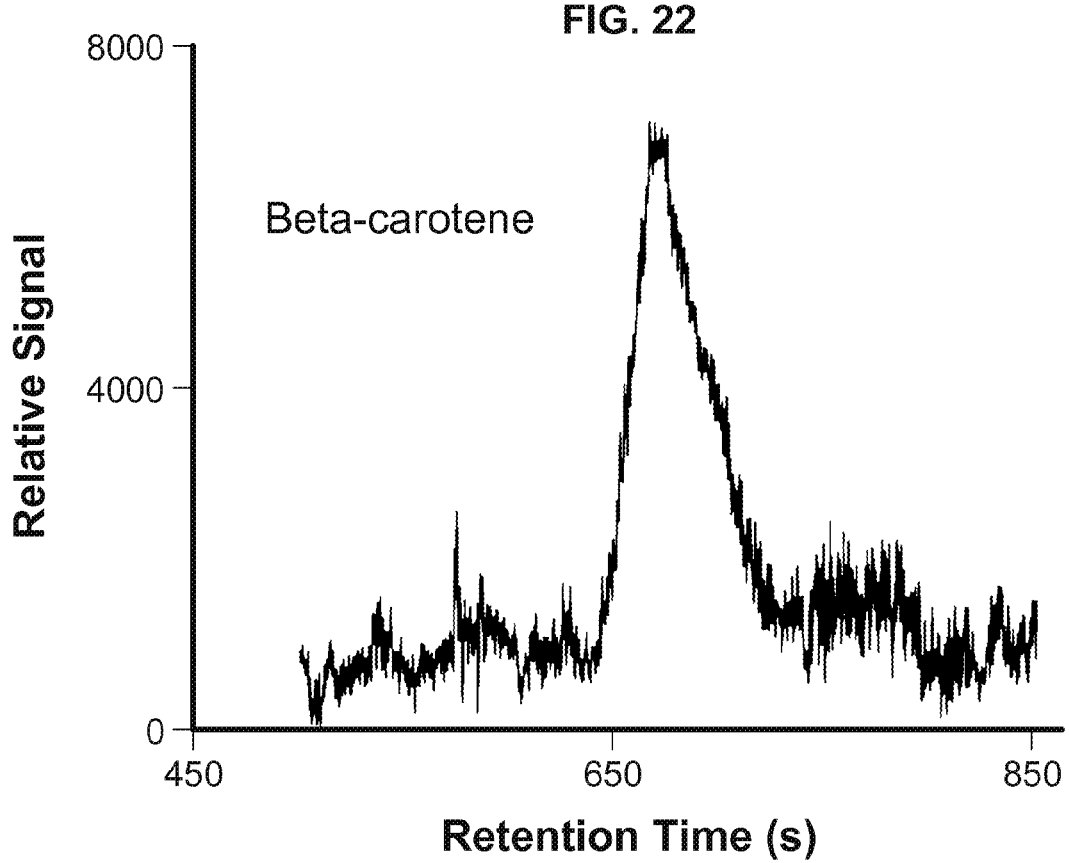
FIG. 23 shows an example of measured chromatogram of □-carotene at $8.2 \times 10^{-8}$ M. A preliminary injected concentration detection limit of $1.3 \times 10^{-8}$ M (S/N 2) and an injected mass detection limit of 13 femtomoles are determined. Based on the probe volume of 113 pL used, a detected mass detection limit of 1.47 attomoles is determined.

FIG. 23 shows a chromatogram of β-carotene at a trace-concentration level and a preliminary "injected" concentration detection limit of 1.3×10-8 M is determined for β-carotene (S/N of 2), which corresponds to a preliminary injected mass detection limit of 13 femtomoles. Using an estimated analyte probe volume, i.e., the overlap volume of the two input beams, of 113 pL, a preliminary "detected" mass detection limit of 1.47 attomoles is determined. The wave-mixing detection sensitivity, especially the mass detection sensitivity, is better or comparable to those previously reported using conventional absorption or fluorescence detectors for carotenoids separated by HPLC (12-17). Our wave-mixing detector offers fluorescence-like detection sensitivity in a HPLC system, and yet, it can be used to detect a wider range of analytes including fluorescing and non-fluorescing molecules. Hence, this nonlinear absorption-based wave-mixing technique offers many potential advantages for sensitive analyses of biochemical and biomedical systems in a wide range of applications.

In another aspect, this document provides an ultrasensitive "absorption-based" wave-mixing detector is presented for the detection of proteins and antibodies using a non-fluorescing chromophore label, Coomassie Brilliant Blue (CBB). The complexes are flowed through a 150 μm i.d. capillary cell and detected using a low-power He—Ne laser. The wave-mixing signal is detected after 10 minutes of room-temperature incubation for the antibody complex and 18 minutes for the protein complex. All solutions are prepared in an aqueous buffer without the addition of organic modifiers. Concentration detection limits of 3.4×10-19 M and 6.4×10-14 M (S/N 2) are determined for bovine serum albumin (BSA) and human Papillomavirus (HPV) antibody, respectively. Based on the small laser probe volume used (i.e., overlap volume of the two input beams), mass detection limits of 1.7×10-22 mol and 2.6×10-17 mol are determined for bovine serum albumin and human Papillomavirus antibody, respectively. Wave-mixing advantages include rapid analyses, small sample/reagent requirements and lower costs. The analytes can be analyzed in pure buffer without the use of organic modifiers to enhance signal levels. This is advantageous since one can keep everything at physiological conditions. Laser wave mixing is also a more universal detection method since both fluorescing and non-fluorescing analytes can be detected at excellent sensitivity levels. Samples may be labeled with non-fluorescing chromophores, not just fluorophores. In laser wave-mixing detection, a large absolute positive signal is measured against a virtually dark background. The coherent laser-like signal beam, unlike the incoherent fluorescence signal, can be collected and detected conveniently. Hence, optical background noise levels are expected to remain the same even when detecting real samples. The wave-mixing signal has a quadratic dependence on concentration, and hence, it is more sensitive to smaller changes in analyte properties, and hence, wave mixing is especially effective for sensor and diagnostics applications.

Wave mixing offers ultrasensitive "absorption-based" detection of proteins and antibodies including but not limited to bovine serum albumin (BSA) and human Papillomavirus (HPV) using a non-fluorescing chromophore label, Coomassie Brilliant Blue (CBB). Wave mixing allows sensitive detection of proteins and antibodies in various applications including the study of disease markers in early stages, well in advance of any external symptoms. For example, the most important risk factor for cervical cancer is infection with human Papillomavirus (HPV), which is among a group of more than 70 types of viruses that are species-specific. Currently, a Pap smear is the established way to test for cervical cancer, however, they are sometimes ambiguous due to the lack of detection sensitivity.

Many sensitive diagnostic tests for HPV infection require sample amplification steps and these extra steps are necessary especially when the starting material is limited or the analyte concentration is not adequate for the detection method available. Sample amplification steps are not only time-consuming but they may also cause problems such as cross contamination of interfering substances, resulting in false positives. Laser wave mixing allows sensitive detection without the use of amplification steps.

Wave mixing detection sensitivity levels are order of magnitude better than those of currently available detection methods, e.g., we obtained concentration detection limits of 3.4× 10-19 M and 6.4×10-14 M (S/N 2) for bovine serum albumin (BSA) and human Papillomavirus (HPV) antibody, respectively. These correspond to mass detection limits of 1.7×10-22 mol and 2.6×10-17 mol, respectively.

Unlike conventional methods, wave mixing offers rapid analyses, small sample/reagent requirements and lower costs. The analytes can be analyzed in pure buffer without the use of organic modifiers to enhance signal levels. This is advantageous since one can keep everything at physiological conditions.

Unlike popular fluorescence detection methods, wave mixing allows the use of non-fluorescing labels or tags for biomolecules, e.g., Coomassie Brilliant Blue (CBB) dye. Currently, the most commonly used detection method for CBB-based protein studies is conventional optical absorption using a UV-visible spectrophotometer. Although it is simple and convenient, the detection sensitivity level of conventional absorption is poor (micrograms or mg/L) and wave mixing offers orders of magnitude better detection sensitivity levels.

Sensitive detection methods, especially those based on optical absorption, are needed for detection of proteins and antibodies in various applications including the study of disease markers. Some diseases produce biomolecules that are present in the body well in advance of any external symptoms. Reliable methods for detecting these marker compounds at very low concentration levels are needed to enable earlier disease diagnosis. When found and treated early, cervical cancer can often be cured. The most important risk factor for cervical cancer is infection with human Papillomavirus (HPV). Papillomaviruses are among a group of more than 70 types of viruses that are species-specific. They produce tumors that contain variable amounts of infectious virus and high-risk HPV types include HPV-16 and HPV-18 (1, 2).

Currently, a Pap smear is the established way to test for cervical cancer. Although these tests are quick, they are sometimes ambiguous due to the lack of detection sensitivity. More sensitive diagnostic tests for HPV infection require sample amplification steps (3, 4). These extra steps are necessary especially when the starting material is limited or the analyte concentration is not adequate for the detection method available. Sample amplification steps are not only time-consuming but they may also cause problems such as cross contamination of interfering substances, resulting in false positives. Laser wave mixing allows sensitive detection without the use of amplification steps.

Coomassie Brilliant Blue (CBB) dye was first introduced as an effective tool for protein studies (5). This assay is popular because it is fast, inexpensive and specific for protein and antibodies. The use of CBB allows measurement of proteins and polypeptides with molecular weights greater than 3000-5000 Da, depending on the charged groups that bind to the dye (6). CBB does not bind to small molecular-weight molecules, and hence, interference is minimal (7) and it could be easily compensated by adding the interference agent to the control blank (5, 8). It is widely used as a marker for protein positions in electrophoretic gels and in various studies including proteins in urine (9), renal function (10), glomerular disease and tubular damage (9), cerebrospinal fluid protein content (11) and protease activity studies (12). Currently, the most commonly used detection method for CBB-based protein studies is conventional optical absorption using a UV-visible spectrophotometer. Although it is simple and convenient, the detection sensitivity level of conventional absorption is poor (micrograms or mg/L) (5, 7, 13, 14). Other protein detection methods use fluorescent dyes, instead of non-fluorescing chromophores, to bind with protein (15). Fluorescence-based detection methods offer better detection sensitivity levels as compared to conventional absorption-based methods, however, they require fluorophores, and some dyes give high background levels. Mass spectrometry is also useful, but it is not as cost effective and not widely available in many laboratories (16). Isoelectric focusing is also used to detect proteins, but detection sensitivity is also limited (17).

In the following sections, laser wave mixing is presented as an ultrasensitive method for detecting antibodies and proteins labeled with CBB in a flowing capillary cell. Wave mixing is an absorption-based laser method that offers excellent detection sensitivity levels for both liquid and gas analytes (18-25). Wave mixing offers many advantages for the detection of proteins and antibodies including small sample requirements, low consumption of reagents, shorter analysis times, no need to use organic modifiers, and a broader range of useable labels including both fluorophores and non-fluorescing chromophores.

The wave-mixing signal has a quadratic dependence on analyte concentration and a cubic power dependence on laser power as shown in the following equation (22-23)

$$I_s \propto I_1^2 I_2 \left( \frac{\lambda^2}{\sin^4\left(\frac{\theta}{2}\right)} \right) Q\left( \frac{\alpha^2}{\kappa^2} \right) \qquad (1)$$

where I1 and I2 represent the signal intensities from the probe and pump beams traveling in the forward direction, and the probe beam I1 has a lower intensity than that of the pump beam I2 The solvent parameter Q is the squared derivative of refractive index with respect to temperature, $Q=(dn/dT)^2$. The parameter □ represents laser wavelength used, □ is the absorption coefficient and k is the thermal conductivity. Since the wave-mixing signal has a quadratic dependence on concentration, absorption path length and temperature gradient of the refractive index, it is more sensitive for measuring smaller changes in analyte properties as compared to conventional absorption or fluorescence methods.

Taking advantage of the cubic dependence on laser power, we have demonstrated that the power levels available from compact portable lasers are adequate to generate a strong wave-mixing signal. Using only a 5-mW He—Ne laser, concentration detection limits of $3.4\times10^{-19}$ M and $6.4\times10^{-14}$ M (S/N 2) are determined for BSA protein and HPV antibody, respectively. Based on the small laser probe volume used (i.e., overlapping volume of the two input beams), mass detection limits of $1.7\times10^{-22}$ mol and $2.6\times10^{-17}$ mol (S/N 2) are determined for BSA protein and HPV antibody, respectively.

Unique nonlinear properties of wave mixing allow the use of a simple, inexpensive, low-power He—Ne laser as the light source for the detection of proteins and antibodies, whether one is using a fluorescing or a non-fluorescing label for biomolecules.

Figure 24:
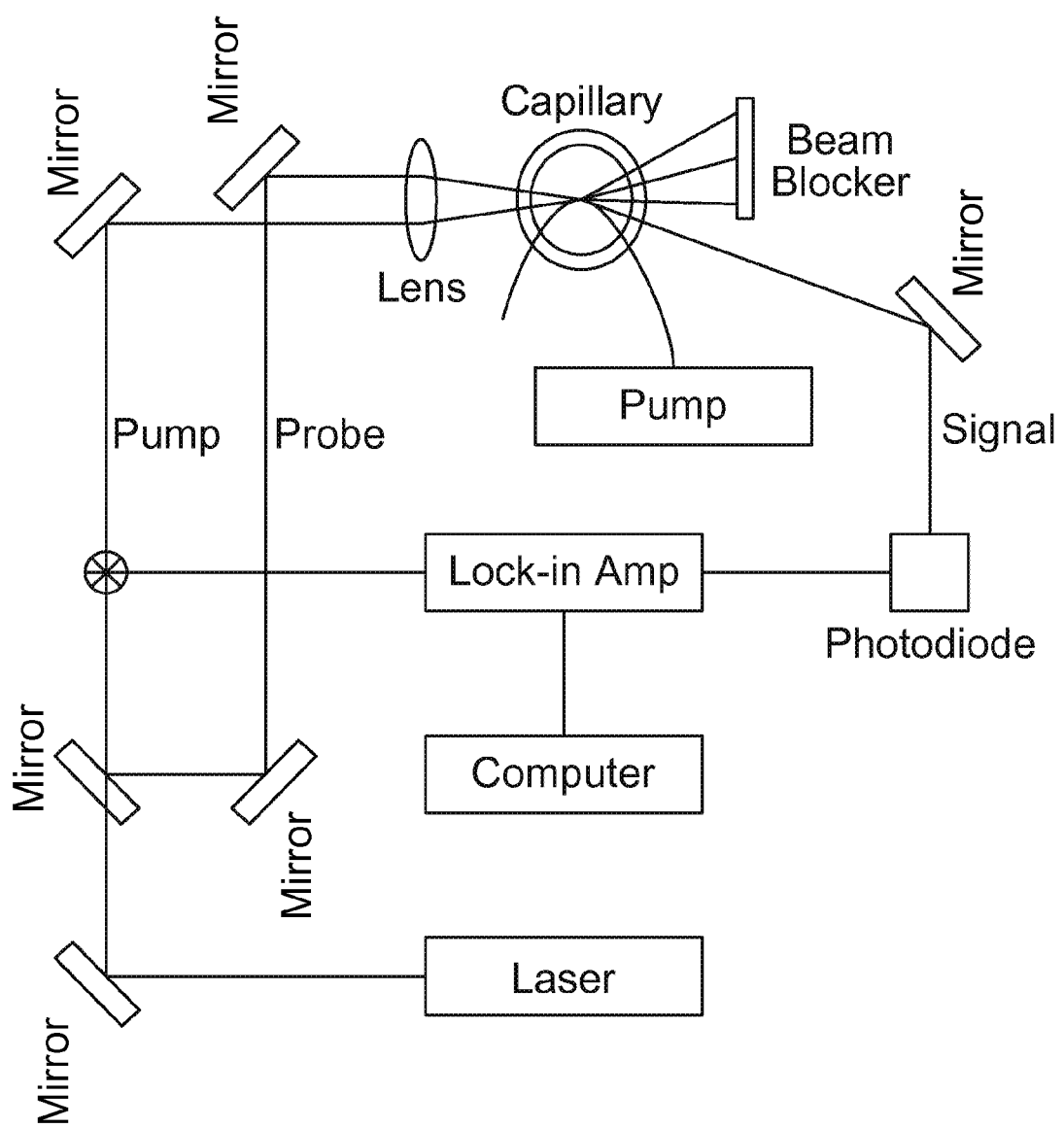
FIG. 24 shows an example of an optical detection device for using wave-mixing for CBB-protein detection.

As shown in FIG. 24, a He—Ne laser (Uniphase, Model 1125P) operating at 632.8 nm with a power of 5 mW is used as the excitation light source. The output of the laser beam is split by a 70/30 R/T beam splitter which forms two input excitation beams. The reflected beam from the beam splitter has the higher laser intensity, and therefore, serves as the pump beam and the probe beam. The transmitted beam serves only as the pump beam. An optical chopper (Stanford Research Systems, model SR541) modulates the amplitude of the pump input beam at 200 Hz. The chopper is interfaced to a lock-in amplifier (Stanford Research Systems, model SR810 DSP) and the signal is digitized by a computer. The two input excitation beams travel equal distances before they are focused and mixed at the capillary cell, creating a small laser probe volume. The two signal beams created by the analyte are coherent laser-like beams and they propagate in the forward direction. The stronger signal beam is directed into a photodiode detector (ThorLabs, Inc., Model PD55) after passing through a spatial filter and a focusing lens. The wave-mixing detector cell is a 150 □m i.d. capillary cell (Polymicro Technologies, Inc.) connected to a peristaltic pump (Rainin Instrument) to flow the analyte at 2.5 mL/min. An alignment dye solution, $1\times10^{-3}$ M Nile blue (Aldrich, 37,008-8), is used to optimize the wave-mixing optical setup.

A benchtop UV-visible spectrophotometer (Hewlett Packard, Model 8452A) is used for conventional optical absorption measurements. Disposable polystyrene cuvettes with a 1-cm path length are used. The instrument is blanked against the specific buffer system used. The CBB stock solution is prepared according to manufacturer instructions (Bio-Rad Laboratories, 500-0006) at 0.1 mg/mL. The tris HCl buffer solution (0.50 M, pH 4) is prepared in deionized doubly-distilled water and filtered (Whatman 44 ashless filter). Commercially available BSA samples (Boehringer Mannheim, 100 360) and mouse anti-human Papillomavirus Type 16 samples (US Biological, P3105-15) are used. All protein and antibody stock solutions are prepared by dissolving a weighed amount of protein in pH 4 tris HCl buffer solution. The stock solutions are then serially diluted down to working concentrations. All solutions are made fresh each day. Different mixing ratios for CBB-protein and CBB-antibody are used with different incubation times. Unless otherwise noted, 200 μL of CBB is mixed with 800 μL of BSA and incubated for 20 min. For the detection limit studies, a 15 min. incubation time is used. For the time studies, a specific amount of CBB is pipetted into a 2 mL plastic vial containing the protein solution, mixed by vortexing and incubated at room temperature before each measurement. The CBB-HPV antibody sample consists of 75 □L of CBB and 400 □L of $3.6\times10^{-9}$ M HPV. The CBB-BSA sample consists of 25 □L of CBB and 800 μL of $1.15\times10^{-12}$ M BSA.

Figure 26:
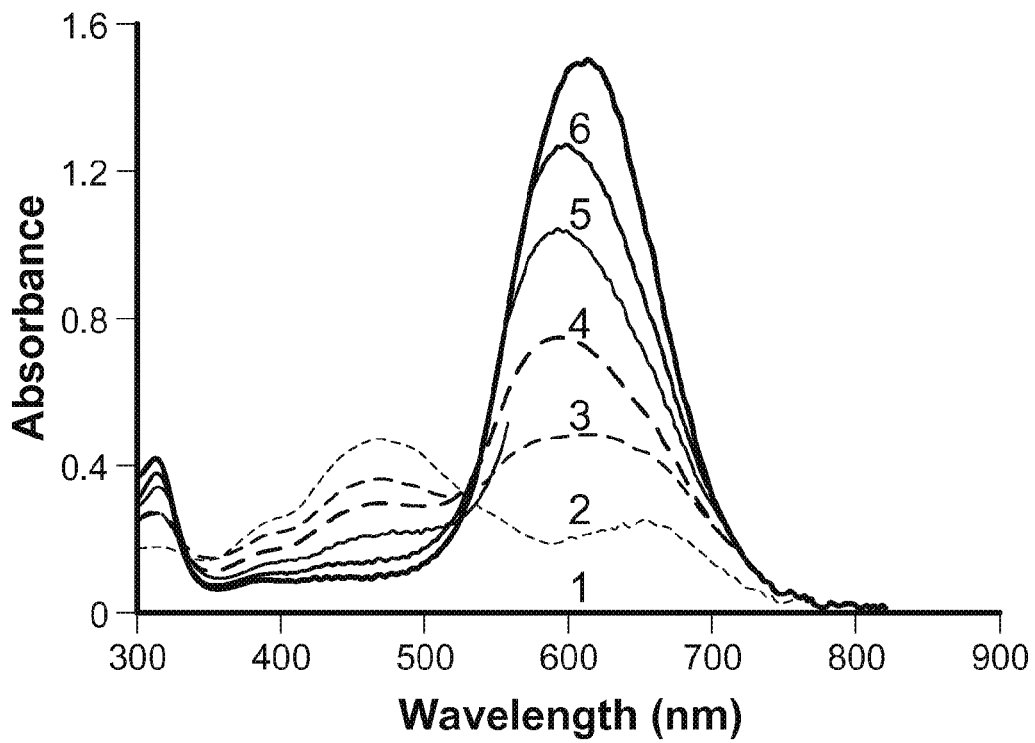
FIG. 26 shows an example of a conventional UV-visible absorption profiles of CBB ($2.4 \times 10^{-7}$ M) in buffer with different concentration levels of BSA protein: (1) only buffer, (2) $2.4 \times 10^{-7}$ M, (3) $6.1 \times 10^{-7}$ M, (4) $1.5 \times 10^{-6}$ M, (5) $5.1 \times 10^{-6}$ M, and (6) $3.2 \times 10^{-5}$ M.

Wave mixing can detect and distinguish small differences in optical absorption of CBB label with and without the biomolecule of interest added. Taking advantage of the quadratic dependence on analyte properties in wave mixing detection, one can distinguish minor changes better than conventional "linear" methods. As shown in FIG. 26, it is difficult for conventional UV-visible spectrophotometers to measure protein concentration levels below $1\times10^{-7}$ M. However, our absorption-based wave-mixing detector is orders of magnitude more sensitive than convention optical absorption methods, and hence, one can measure protein absorption shifts at very low concentration levels for many biomedical samples.

Wave mixing allows the use of simple, inexpensive and off-the-shelf components such as a simple peristaltic pump to pull, instead of push, the analyte in order to ensure all-glass contact with the analyte.

Figure 27:
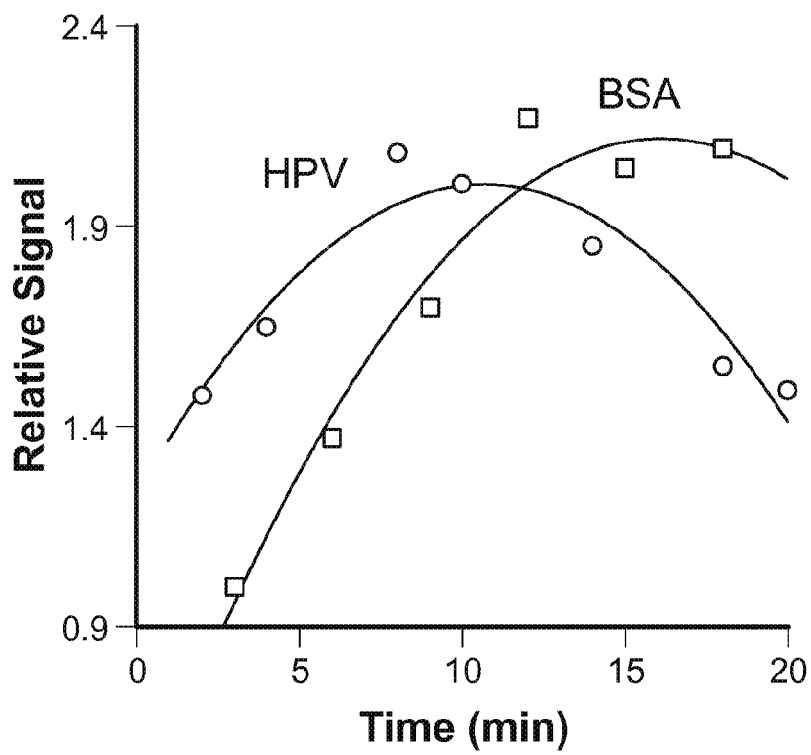
FIG. 27 shows an example where the wave-mixing signal increases as CBB binds with protein. A maximum signal is observed at 10 min. for CBB-HPV antibody and at 18 min. for CBB-BSA.

Wave mixing allows fast and almost real-time detection, as shown in FIG. 27, where the wave mixing signal is shown to be sensitive enough to almost immediately detect CBB-protein binding. No extended incubation times are required for sensitive wave-mixing detection. This is especially advantageous when performing multiple assays to obtain higher throughput.

The wave-mixing signal is generated instantaneously, and hence, wave mixing can be used to monitor fast dynamic events (i.e., it does not even have fluorescence lifetime delays as in fluorescence methods).

Laser wave mixing offers excellent detection sensitivity levels and yet it is applicable to both non-fluorescing chromophore and fluorophore labels. Our enhanced detection limits will help in detecting cancer precursors at much lower concentration levels as compared to other methods.

Since the wave-mixing laser probe volume is small (nL to pL), it is inherently suitable for interfacing to microfluidic and microarray devices. Different biomolecules, proteins, antibodies, etc., could be distinguished from one another when the wave-mixing detection system is interfaced to a microchip-based electrophoresis system or a capillary-based separation system.

The CBB reagent exists in the cationic, neutral and anionic forms. The anionic form complexes with proteins and antibodies. Protonation of the dye structure, upon binding to protein, occurs at one of the two tertiary amines, followed by protonation at the other, effectively causing a hypsochromic shift (8). This dye-to-protein interaction is mainly contributed to the arginine amino acids rather than the primary amino groups of the protein. Other basic (His, Lys) and aromatic residues (Try, Tyr and Phe) give slight binding responses. The dye-protein binding behavior is attributed to Van der Waals forces and hydrophobic interactions (8). There are some known interferences caused by compounds like bases, detergents and others that affect the reaction equilibria between the three dye forms (8). Many known interferences in the samples can be compensated for by adding the interference agent to the control blank, thus still allowing accurate determination of proteins (5).

Figure 25:
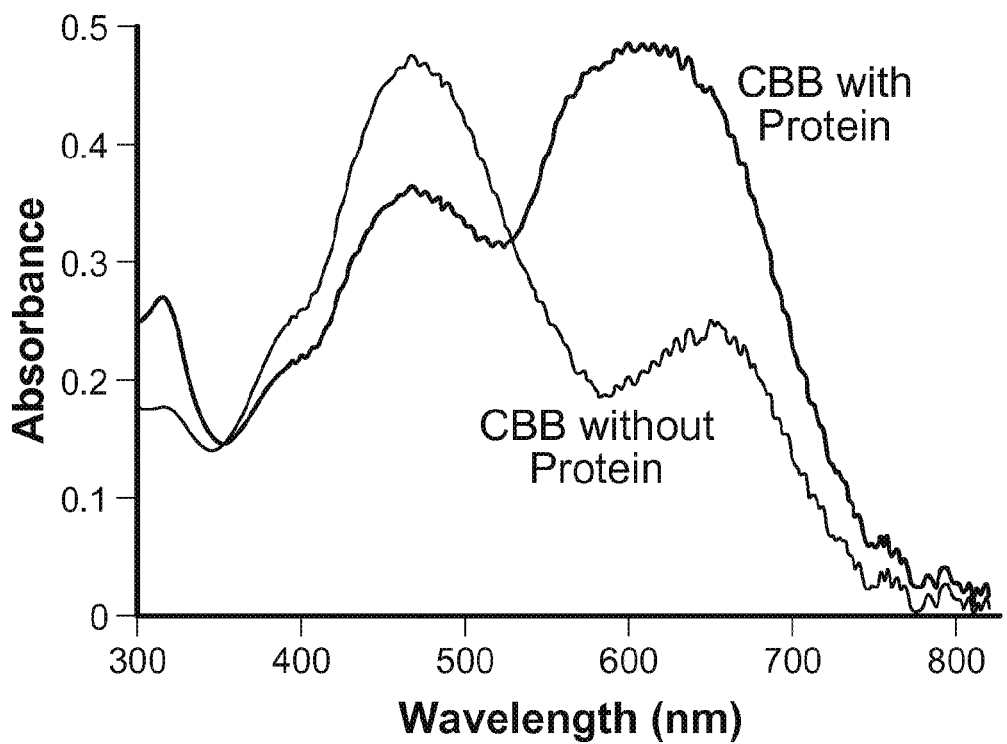
FIG. 25 shows an example of the absorption shift of CBB due to protein binding. Concentration of BSA protein and CBB are both $2.4 \times 10^{-7}$ M.

FIG. 25 shows UV-visible absorption spectra of CBB with and without protein added. The dye normally has an absorption maximum at 465 nm. Upon binding to a specific protein or antibody, the absorption maximum shifts to 590 nm (8). This absorption shift can be monitored to determine the amount of protein or antibody bound to the dye. The dye alone has a significant absorption peak at the same wavelength as the new peak due to protein complexation. This background can be effectively minimized by using appropriate CBB-protein ratios.

FIG. 26 shows CBB optical absorption profiles at different protein concentration levels. The CBB-BSA complex absorption is measured using a conventional UV-visible spectrophotometer. The magnitude of the absorption peak shift is proportional to the protein concentration level. As shown in FIG. 26, it is difficult for conventional UV-visible spectrophotometers to measure protein concentration levels below $1\times10^{-7}$ M. On the other hand, our absorption-based wave-mixing detector is orders of magnitude more sensitive than convention optical absorption methods, and hence, one can measure protein absorption shifts at very low concentration levels of many biomedical samples.

The laser wave-mixing optical setup is optimized first by securely mounting the glass capillary cell on a XYZ translational stage using rubber O-rings to avoid any movement of the capillary that can affect the wave-mixing thermal gratings. The two input beams are directed, focused and mixed inside the analyte solution within the capillary channel using a XYZ translational stage in order to maximize the sharpness of the gratings and to minimize light scattering off the capillary walls. This optimization step is relatively easy since the signal is visible to the naked eye when the alignment solution is present. The XYZ translational stage offers easy alignment of the optimum location of the capillary with respect to the input beams (X and Z directions). It also allows easy positioning of the cell at or near the focused point of the input beams (Y direction). To verify the stability of the optical setup, the alignment dye is reintroduced to the system and signal verified before and after protein runs. The capillary cell is rinsed thoroughly with ethanol to remove any residues from previous analyte runs.

A peristaltic pump is used to pull, instead of push, the analyte in order to ensure all-glass contact with the analyte. As expected, any low flow rates above the static mode yields slightly enhanced wave-mixing signal since the analyte solution within the laser probe volume is refreshed. At much higher flow rates, the wave-mixing signal is slightly attenuated due to some thermal grating wash-out effect. An optimal flow rate for this wave-mixing setup is determined to be 2.5 mL/min where the analyte is adequately refreshed while the thermal gratings remain sharp. Although there is an optimum flow rate, the wave-mixing setup yields excellent signal levels over a wide range of commonly used flow rates for many applications.

FIG. 27 shows dependence of CBB-BSA and CBB-HPV antibody signals on incubation time. As mentioned above, the CBB-HPV antibody sample consists of 75 μL of CBB and 400 μL of $3.6\times10^{-9}$ M HPV antibody and the CBB-BSA sample consists of 25 μL of CBB and 800 μL of $1.15\times10^{-12}$ M BSA. As soon as the solutions are mixed, wave-mixing signals are monitored and recorded at different time intervals. The CBB-HPV antibody complex signal is maximized at 10 min. and the CBB-BSA complex signal at 18 min. based on the least-squared fit analysis. The CBB-HPV antibody signal reaches the maximum faster than the CBB-BSA signal, most likely due to the higher molecular weight of HPV antibody that results in a faster binding rate with CBB. Once the maximum signal is reached, a signal decrease is observed due to aggregation of the CBB-protein complex. This aggregation effect has been observed before in this type of assays (5). It is apparent from FIG. 4 that wave mixing is sensitive enough to almost immediately detect CBB-protein binding. No extended incubation times are required for sensitive wave-mixing signal detection. This is especially advantageous when performing multiple assays to obtain higher throughput.

The CBB-protein ratio plays an important role in the binding reaction and detection sensitivity levels. Enough protein must be present to bind with CBB so that an absorption shift is observed. However, if too much CBB is present, it increases the background level unnecessarily. Studies are performed to obtain the optimal ratios for CBB-BSA and CBB-HPV. Protein concentration is held constant at $1\times10^{-12}$ M BSA and the CBB amount is varied by a factor of 5/3. As expected, a small addition of CBB changes the wave-mixing intensity and the incubation time since the presence of more CBB molecules allows faster and increased protein-dye complexation. After 15 minutes of incubation time, the absorption begins to decrease due to the precipitation of CBB-protein complex (25 μL protein with 15 μL CBB) (13). For this amount of CBB, it is protein dependent, and thus, the ratio is different for CBB-HPV antibody complexation. The optimal ratios are determined to be 1:20 for CBB-BSA (i.e., 25 μL CBB to 500 μL BSA), and 1:5.3 for CBB-HPV antibody (75 μL mole CBB to 400 μL HPV).

Figure 28:
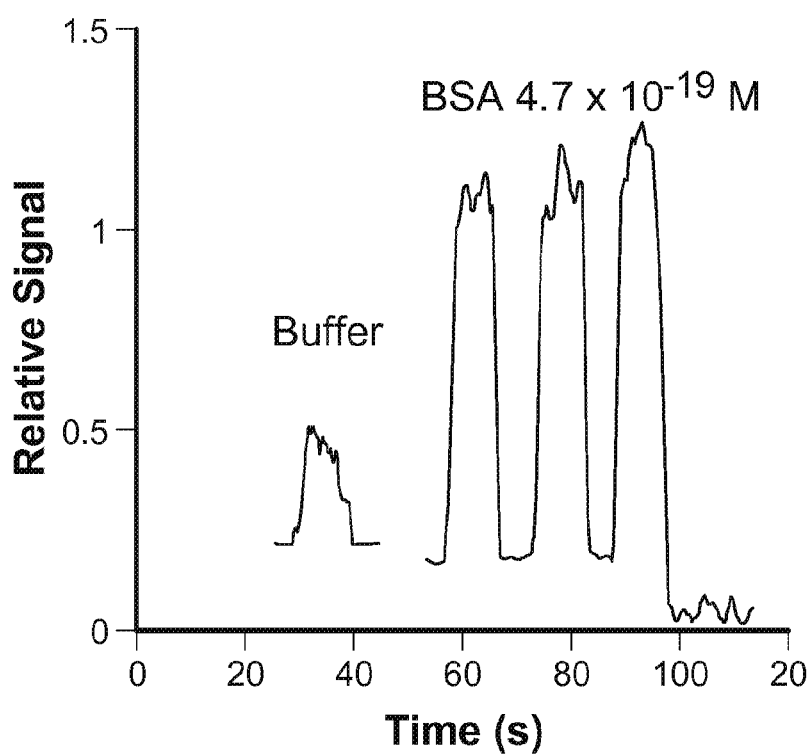
FIG. 28 shows an example of a sensitive detection of CBB-BSA protein complex using wave mixing.

The wave-mixing detection sensitivity is verified by running a series of BSA analytes ranging in concentration from $1\times10^{-19}$ M to $3\times10^{-16}$ M using the optimal CBB-BSA binding ratio. FIG. 5 shows the wave-mixing signal of BSA at the $4.7\times10^{-19}$ M concentration level. The CBB-BSA wave-mixing signal is collected in three reproducible signal intervals using a beam blocker to block and unblock the signal three times, as shown in FIG. 28. The wave-mixing signal is also compared to a blank solution which consists of the buffer and the CBB reagent at the same concentration levels as those in the analyte. Although the blank solution does not contain any protein, a small background signal is observed since CBB itself absorbs slightly at the wavelength used, as shown in FIG. 25. A concentration detection limit of $3.4\times10^{-19}$ M, $2.3\times10^{-17}$ g/mL or 23 attogram/mL (S/N 2) is determined for BSA. Based on the laser probe volume used (500 μL), a mass detection limit of $1.7\times10^{-22}$ mol or $1.2\times10^{-17}$ g (S/N 2) is determined for BSA (68 kDa). This corresponds to about 100 molecules of BSA protein present at any one time inside the small laser probe volume within the fast flowing capillary channel.

Figure 29:
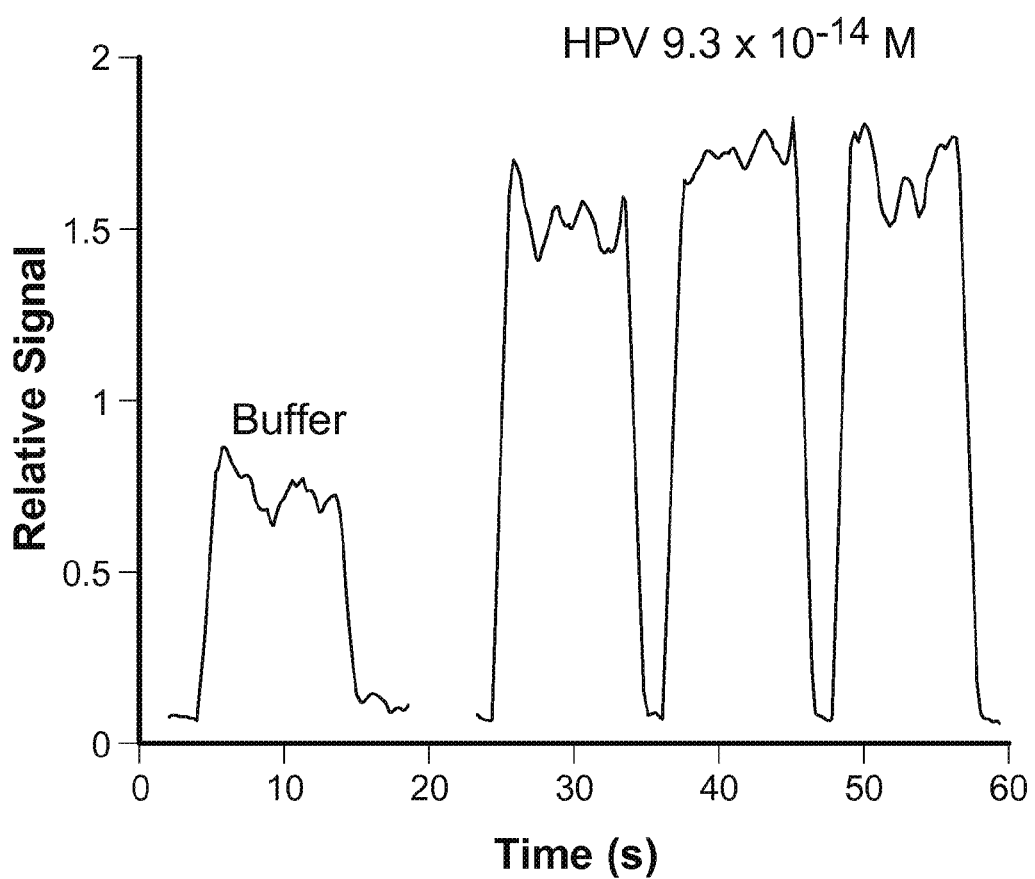
FIG. 29 shows an example of a sensitive detection of CBB-HPV antibody complex using wave mixing.

The wave-mixing detection sensitivity is also verified for HPV antibody by running a series of HPV antibody analytes ranging in concentration from $1\times10^{-15}$ M to $1\times10^{-8}$ M in a similar manner using the optimal CBB-HPV antibody binding ratio. FIG. 29 shows the wave-mixing signal at the $9.3\times10^{-14}$ M HPV antibody concentration level. A concentration detection limit of $6.4\times10^{-14}$ M or $9.6\times10^{-12}$ g/mL (S/N 2) is determined for HPV. Based on the laser probe volume used (400 μL), a mass detection limit of $2.6\times10^{-17}$ mol or $3.8\times10^{-12}$ g (S/N 2) is determined for HPV antibody (150 kDa). Hence, laser wave mixing offers comparable or better detection sensitivity levels than those of other currently available detection methods for proteins including laser-based fluorescence methods. Laser wave mixing offers excellent detection sensitivity levels and yet it is applicable to both non-fluorescing chromophore and fluorophore labels. Our enhanced detection limits will help in detecting cancer precursors at much lower concentration levels as compared to other methods. Our detection limits could be further improved by minimizing optical background noise levels more efficiently using polarization modulated detection techniques, as we have done previously. The wave-mixing signal is generated instantaneously, and hence, wave mixing can be used to monitor fast dynamic events (i.e., it does not even have fluorescence lifetime delays as in fluorescence methods). Since the laser probe volume is small (nL to pL) and one can adjust it conveniently by using an appropriate lens, it is inherently suitable for interfacing to microfluidic and microarray devices. As demonstrated for other biomedical applications in our laboratory, different biomolecules, proteins, etc., including HPV antibody, could be distinguished from one another when the wave-mixing detection system is interfaced to a microchip-based electrophoresis system or a capillary-based separation system.

Wave mixing can also be used to provide a sensitive absorption-based detector for anthracycline antibiotics, daunorubicin and doxorubicin, using a capillary electrophoresis chemical separation system. Unlike conventional absorption methods, this nonlinear absorption method can detect very thin analytes (50 $\mu$m) efficiently. At the same peak height, the wave-mixing CE peak is narrower than a conventional CE peak, and hence, compared to other laser-based or non-laser-based CE on-column detection methods, our wave-mixing detection method offers intrinsically enhanced separation resolution even when using identical CE separation conditions. In this unusually sensitive "absorbance" detection method, two input laser beams interact to produce a thermally induced grating from which coherent laser-like wave-mixing signal beams are created. Using our sensitive "absorbance" on-column CE detector, we report a preliminary concentration detection limit of $9.9 \times 10\text{-}10$ M using a 50 $\mu$m i.d. capillary column. The corresponding "injected" mass detection limit is $9.1 \times 10\text{-}18$ mol using an injection volume of 9.2 nL. The corresponding preliminary "detected" mass detection limit inside the 12-pL detector probe volume is $1.2 \times 10\text{-}20$ M. Our absorption-based wave-mixing detector offers fluorescence-like detection sensitivity levels in a CE system and it can used to detect a wider range of fluorescing and non-fluorescing analytes. Hence, this nonlinear laser-based technique offers important advantages for sensitive absorption detection of biochemical and biomedical analytes in a wide range of applications.

In the sections below, wave mixing is presented as a reliable and sensitive absorption-based detector for anthracycline antibiotics, daunorubicin and doxorubicin, using a capillary electrophoresis chemical separation system. Unlike conventional "absorption" methods that require a relatively long (1 cm) optical absorption path length, this nonlinear absorption method can detect very thin analytes (50 $\mu$m) efficiently.

At the same peak height, the wave-mixing CE peaks for antibiotics are narrower than conventional CE peaks, and hence, compared to other laser-based or non-laser-based CE on-column detection methods, our wave-mixing detection method offers intrinsically enhanced separation resolution even when using identical CE separation conditions.

Wave-mixing detection sensitivity levels are orders of magnitude better than those from currently available methods. We obtained a concentration detection limit of $9.9 \times 10\text{-}10$ M, an "injected" mass detection limit of $9.1 \times 10\text{-}18$ mol, and a "detected" mass detection limit of $1.2 \times 10\text{-}20$ M.

Our absorption-based wave-mixing detector offers fluorescence-like detection sensitivity levels in a CE chemical separation system and it can be used to detect a wider range of fluorescing and non-fluorescing analytes. Hence, this nonlinear laser-based technique offers important advantages for sensitive absorption detection of biochemical and biomedical analytes in a wide range of applications.

Capillary electrophoresis (CE) is an effective analytical tool for many applications including analysis of metabolites and drugs, analysis of natural products and proteins, and DNA sequencing. It offers high separation efficiency, short analysis time, small sample and buffer requirements, and convenient direct on-column detection. Due to small detector volumes (<nL) and short light absorption path lengths (<50 $\mu$m) available, on-column detection in capillary electrophoresis demands sensitive detection methods that can use short light path lengths efficiently. The most commonly used on-column detection methods for capillary electrophoresis are UV-visible absorption, conventional fluorescence and laser-induced fluorescence methods. Conventional UV-visible absorption detectors offer good linearity but they lack detection sensitivity. Laser-induced fluorescence offers good detection sensitivity, but they are applicable only to compounds that can fluoresce or can be labeled with fluorescing tags.

An unusually sensitive laser-based "absorbance" detection method based on forward-scattering wave mixing offers excellent detection sensitivity for small absorbance measurements while using short absorption path lengths (50 $\mu$m). In this nonlinear laser detection method, two coherent input laser beams are focused and mixed inside an absorbing analyte. The resulting thermal gratings scatter off incoming photons from the two input beams to produce wave-mixing signal beams. The signal has important nonlinear characteristics including its cubic dependence on laser power and its quadratic dependence on solute absorption coefficient. The coherent laser-like properties of the signal beam allow virtually 100% optical signal collection efficiency with excellent S/N. Since the signal is visible to the naked eye even at low concentration levels, optical alignment is simple and convenient.

We have demonstrated effective use of nonlinear wave-mixing methods in various applications for both gas- and liquid-phase analytes using a wide range of lasers including low-power diode lasers. In gas-phase media, the backward-scattering wave-mixing optical arrangement yields sub-Doppler spectral resolution and it allows hyperfine structure measurements and isotope ratio analyses in various atomizers including hollow-cathode discharge plasmas, flames and graphite furnaces (1-4). For continuously flowing liquid analytes, we have reported attomole-level detection sensitivity (5) that is comparable or better to those of laser-based fluorescence detection methods, and yet our detection system is applicable to both fluorescing and non-fluorescing analytes. In addition, we demonstrated circular dichroism and optical activity measurements at trace-concentration levels using nonlinear wave mixing (6-8).

The separation and detection of anthracycline antibiotics, daunorubicin (DAU) and doxorubicin (DOX) were demonstrated by using a capillary electrophoresis system interfaced to an absorption-based nonlinear wave-mixing detector. The studies of anthracyclines and the determination of DAU and DOX mostly involve HPLC and capillary electrophoresis (9-14) and excellent detection limits have been reported using fluorescence-based detection methods. Using our sensitive "absorbance" on-column CE detector, we achieved a preliminary concentration detection limit of $9.9 \times 10\text{-}10$ M at S/N of 2 using a 50-$\mu$m i.d. capillary column. The corresponding preliminary "injected" mass detection limit is $9.1 \times 10\text{-}18$ mol using an injection volume of 9.2 nL. The corresponding preliminary "detected" mass detection limit inside the 12-pL laser probe volume is $1.2 \times 10\text{-}20$ M.

Wave mixing is inherently suitable for interfacing to micro-channel, capillary and microfluidic chemical separation systems for high throughput analyses while still offering excellent detection sensitivity levels. The input laser beams can be interfaced to small micro-channels and capillary tubes with 50 μm or smaller inside diameters.

Figure 30:
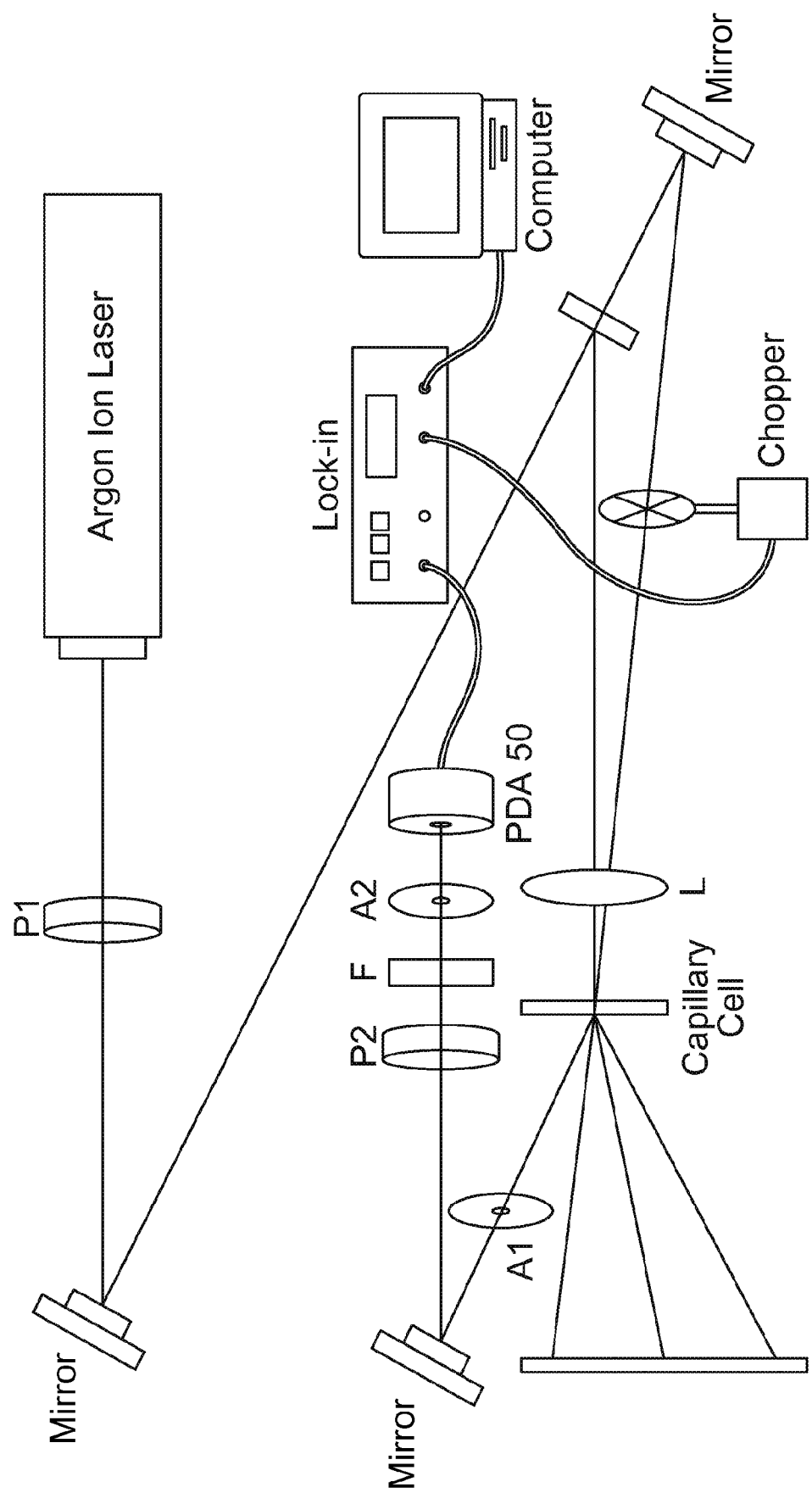
FIG. 30 shows an example of an optical detection device for capillary electrophoresis wave-mixing detection of anthracycline drugs. P1, P2, polarizers; L1, L2, focusing lenses; A1, A2, apertures; F, filter.

FIG. 30 shows a simple and easy-to-align forward-scattering wave-mixing on-column detector for CE. The laser source is a continuous-wave argon ion laser operating at 476.5 nm. The laser passes through a polarizer and then a 70:30 beam splitter to form the pump beam and the probe beam. In order to maximize wave-mixing grating contrast, the path length difference between the pump and the probe is adjusted so that it is shorter than the coherence length of the laser. These two input beams are then focused on the capillary using a 7-cm focal length lens. The capillary is positioned in a donut-shaped mount and controlled by a XYZ translational stage for precise optical alignment. An aperture is placed right after the capillary to allow only the signal beam to pass through. The coherent laser-like signal beam is then filtered by a polarizer and an aperture and then focused by a 20-cm focal length lens on a photodiode. The photodiode signal is processed by a lock-in amplifier (Stanford Research Systems, Inc., Sunnyvale, Calif., Model SR810 DSP) which is referenced to a mechanical chopper modulating the probe beam at 200 Hz. The signal is finally digitized by a computer.

Our custom-built CE system consists of a power supply (Glassman High Voltage, Inc., Whitehouse Station, N.J., Model PS/MJ30P0400-11) with voltage and current monitors, two electrodes, two buffer vials, and a piece of capillary. For safety considerations, the anode is kept into a Plexi-Glass box. The cathode is placed on the side arm of the box in order to maintain the same height for the two buffer vials and to reduce the total length of the capillary. The laser beams are interfaced to the uncoated fused silica capillary (Polymicro Technologies, Inc., Phoenix, Ariz., 75 cm total length, 45 cm effective length). Capillary tubes with different dimensions are used in this study including those with 50 μm i.d./363 μm o.d., 75 μm i.d./363 μm o.d., 100 μm i.d./363 μm o.d., and 180 μm i.d./340 μm o.d. A 1-cm wide detection window is created for on-column detection by burning off the coating and cleaning with methanol. The capillary is back filled with an alignment solution for optical alignment using a vacuum pump (Barnant Company, Barrington, Ill., Model 400-1901). Before CE separation runs, the capillary is flushed with 0.1 M NaOH, DI water, and the running buffer for 20 minutes each, followed by the buffer at separation voltage for about 30 min. The analytes are injected electrokinetically at the anodic end at 12 kV for 5 s.

The running buffer consists of acetonitrile and 100 mM, pH 4.2, sodium dihydrogen phosphate buffer (70/30, v/v). It is filtered with a Nylon membrane filter (Phenomenex, Torrance, Calif.) and degassed with a sonicator. The analyte stock solutions are prepared by dissolving solid DAU and DOX analytes (Calbiochem, La Jolla, Calif.) in DI water. Different analyte concentrations are prepared by diluting the stock solution with the running buffer, followed by filtration with a Nylon membrane filter and degassing with a sonicator.

The basic anthracycline structure yields optical absorption around 250 nm and 480 nm when coupled to an amino sugar. Although DAU and DOX exhibit stronger absorption at 250 nm, this UV wavelength is not convenient for trace analysis of these two drugs in real-time drug monitoring sessions due to the presence of strong interferences from other entities in the biological matrix and the intrinsically higher background noise levels associated with this wavelength range. Conventional absorption-based detection methods must use the stronger transition line in order to obtain reliable signal strengths. However, wave mixing offers much stronger signals and higher S/N, and hence, one can afford to use the weaker transition line near 480 nm and still obtain excellent detection sensitivity levels.

The use of a convenient visible laser excitation line (476.5 nm in our optical setup) allows one to design a more user friendly detector for anthracyclines as compared to those detectors employing UV light sources. Wave mixing affords strong signals from these clinically important anticancer drugs by just monitoring native absorption using the weaker transition line in the visible wavelength range.

Figure 32:
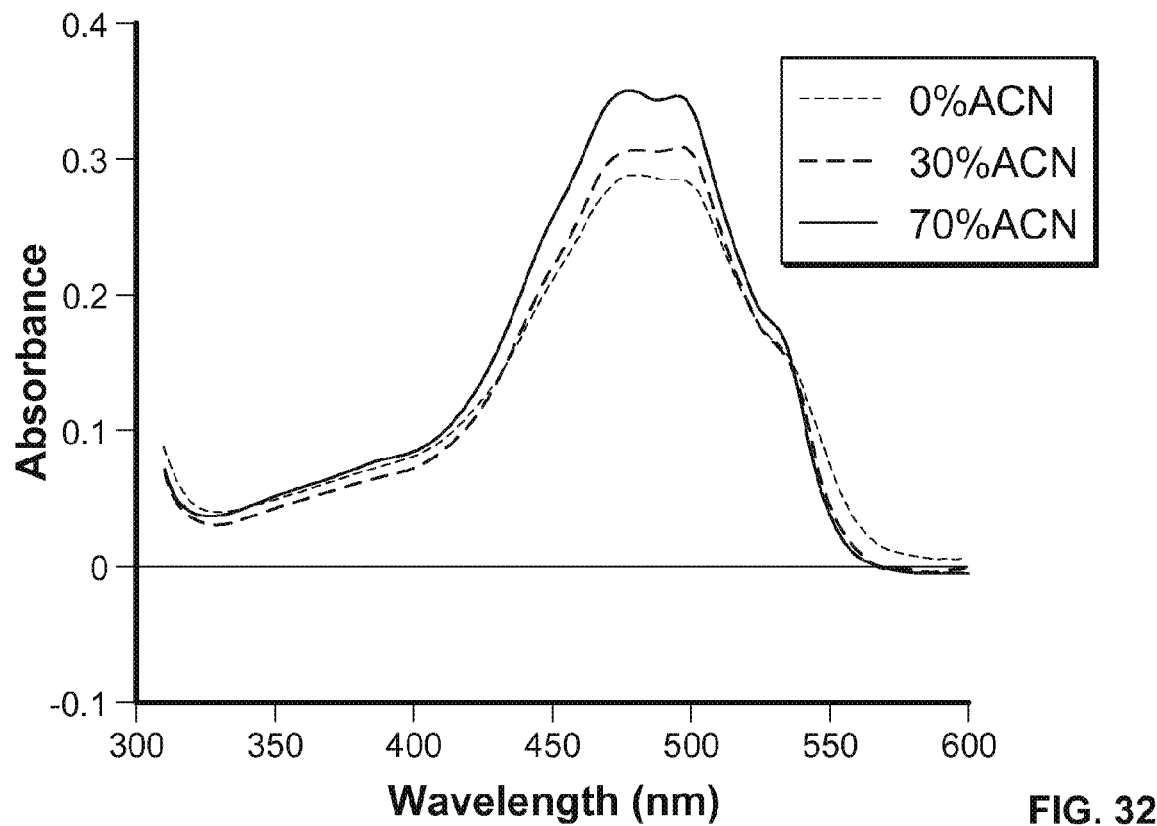
FIG. 32 shows an example of absorption spectra of $2.7 \times 10^{-5}$ M DAU in a phosphate CE buffer modified with (a) 0% acetonitrile, (b) 30% acetonitrile and (c) 70% acetonitrile.

As shown in FIG. 32, the use of a higher percentage of acetonitrile (ACN) organic modifier in the CE separation buffer (solvent) not only improves CE chemical separation of DAU and DOX, it also enhances the buffer solvent thermo-optical properties, resulting in a stronger wave-mixing signal.

Figure 33:
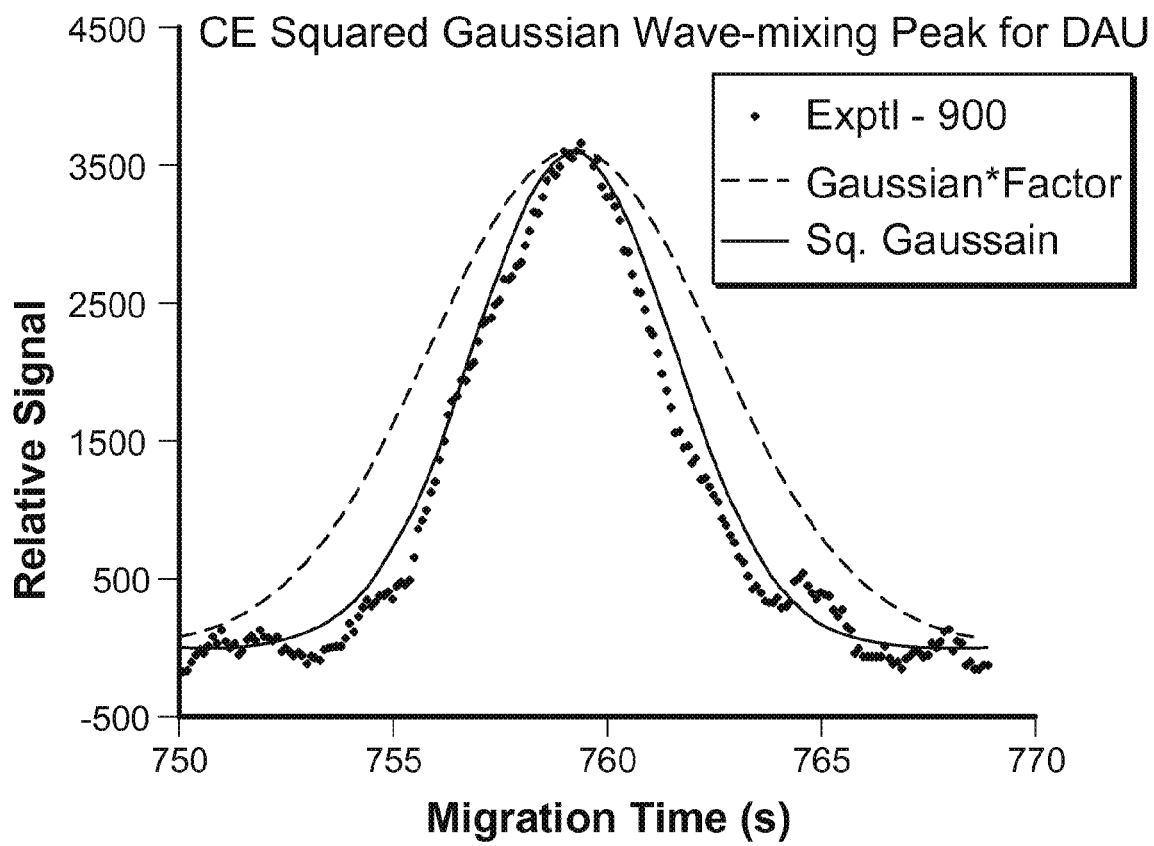
FIG. 33 shows an example of comparison of CE peak profiles: (a) theoretical Gaussian profile, (b) theoretical squared Gaussian profile and (c) experimental wave-mixing signal profile.

The wave-mixing signal has a quadratic dependence on analyte concentration, and hence, the wave-mixing peak profile has a squared Gaussian profile. As shown in FIG. 33, our experimental wave-mixing peak profile for DAU closely matches to the expected squared Gaussian profile. The conventional CE absorption or fluorescence signal, resulting from one-photon excitation, has a linear dependence on analyte concentration, and hence, the conventional CE peak follows a normal Gaussian profile, as shown in FIG. 33. At the same peak height, the wave-mixing CE peak is narrower than a conventional CE peak, and hence, compared to other laser-based or non-laser-based CE on-column detection methods, our wave-mixing detection method offers intrinsically enhanced separation resolution even when using identical CE separation conditions.

Even when using a weak transition line, wave mixing offers detection sensitivity levels (an injected mass detection limit of $9.1 \times 10^{-18}$ mol) that are better than those previously reported for laser-based absorbance or fluorescence determination of anthracyclines separated by high-performance liquid chromatography (HPLC) or CE.

The basic anthracycline structure consists of a tetracyclic quinoid moiety that yields optical absorption around 250 nm and 480 nm when coupled to an amino-sugar (15). Although DAU and DOX exhibit stronger absorption at 250 nm, this UV wavelength is not convenient for trace analysis of these two drugs in real-time drug monitoring sessions due to the presence of strong interferences from other entities in the biological matrix (15) and the intrinsically higher background noise levels associated with this wavelength range.

Figure 31:
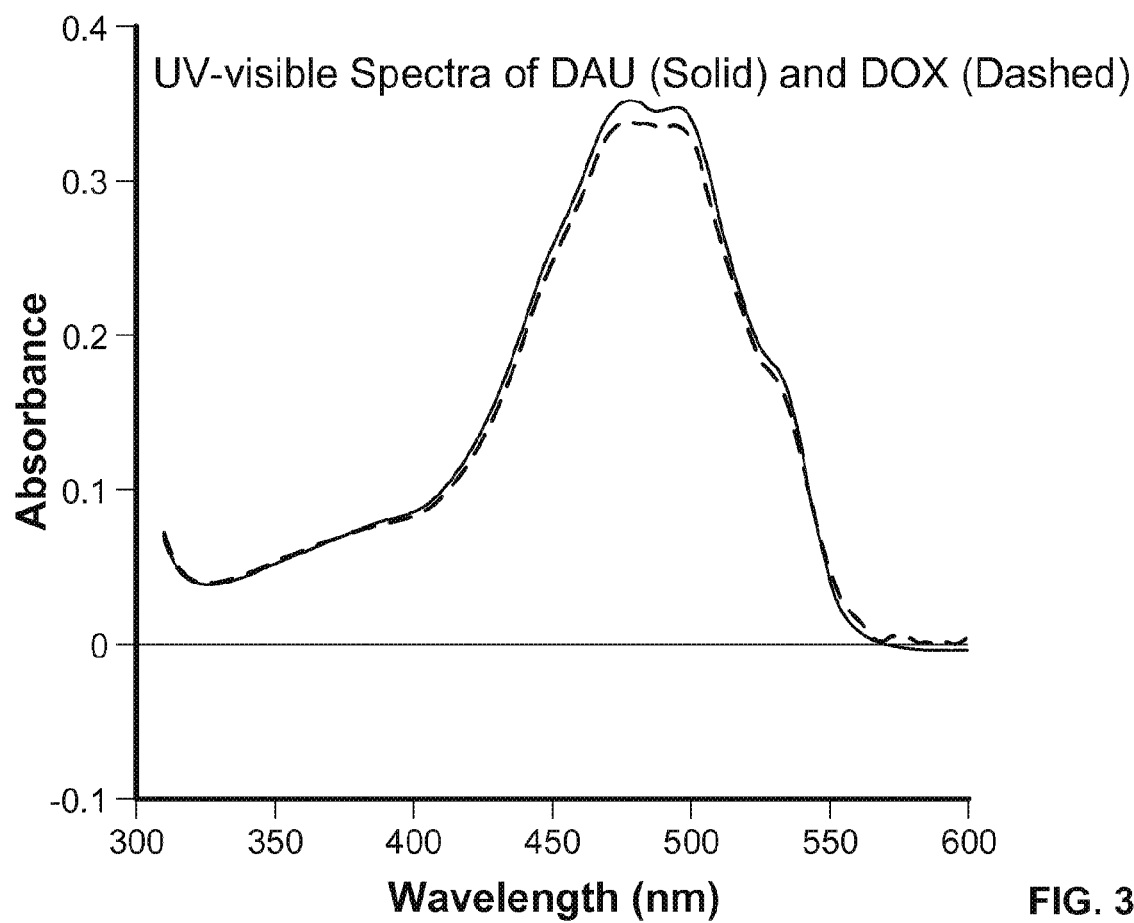
FIG. 31 shows an example of absorption spectra of (a) $2.7 \times 10^{-5}$ M DAU and (b) $2.8 \times 10^{-5}$ M DOX in a 100 mM phosphate buffer/acetonitrile solvent binary mixture (30:70, v/v) at pH 4.2.

FIG. 31 shows the UV-visible absorption spectra of DAU and DOX in a 100 mM phosphate buffer-ACN solvent (30:70, v/v). The wavelength maximum in the visible range for both drugs is 476.5 nm. Our argon ion laser provides several wavelengths (457.9 nm, 476.5 nm, 488 nm, 515 nm, etc.) and we use the 476.5 nm argon ion line to probe both anthracyclines. At this wavelength, the absorption coefficients of DAU and DOX in the selected binary buffer system are $1.3 \times 10^4$ M$^{-1}$ cm$^{-1}$ and $1.2 \times 10^4$ M$^{-1}$ cm$^{-1}$, respectively. These two clinically important anticancer drugs exhibit substantial native absorption in the visible wavelength range, and therefore, they are used as analytes in our nonlinear wave-mixing "absorption-based" detection system.

Since the migration of analyte species is based on electrophoresis and electroosmosis effects, aqueous electrolyte buffer systems are usually used in CE systems. However, organic or mixed organic-aqueous buffers offer some advantages in CE including increased solubility for solutes that show poor solubility in water, reduced Joule heating, and enhanced separation resolution. It has been demonstrated that the use of ACN organic modifier in an aqueous phosphate buffer reduces the interaction of anthracycline analytes with the capillary wall (16), reduces Joule heating and enhances separation efficiency. Hence, a mixture of aqueous phosphate buffer and ACN organic solvent (30:70, v/v) is used as a binary buffer electrolyte system in our CE system to separate DAU and DOX.

Since the wave-mixing signal has a quadratic dependence on the refractive index change with temperature (dn/dT) of the solvent, a solvent with good thermo-optical properties should be used, when possible. The dn/dT value for water is low (0.14×10-4 mW-1 cm at 20° C.) and organic solvents have higher dn/dT values, ranging from 1.9×10-4 mW-1 cm (methanol) to 5.9×10-4 mW-1 cm (carbon tetrachloride). Hence, the addition of an organic modifier in an aqueous buffer enhances the dn/dT value, resulting in a stronger wave-mixing signal. Furthermore, the absorption coefficients of the two anthracyclines under study increase as the ratio of organic solvent to water in the buffer system is increased, resulting in a stronger wave-mixing signal.

As shown in FIG. 32, the absorption coefficient of DAU increases from 6.43×103 M-1 cm-1 in a pure aqueous phosphate buffer to 1.29×104 M-1 cm-1 in a binary buffer containing 70% ACN. Hence, the use of a higher percentage of ACN organic modifier in the CE buffer not only improves CE separation of DAU and DOX, it also enhances the buffer thermo-optical properties, resulting in a stronger wave-mixing signal.

FIG. 33 compares theoretical and experimental wave-mixing CE peak profiles to that expected from a conventional CE system. Since the multi-photon wave-mixing signal has a quadratic dependence on analyte concentration, the theoretical wave-mixing peak profile has a squared Gaussian profile. As shown in FIG. 4, our experimental wave-mixing peak profile for DAU closely matches to the expected squared Gaussian profile. The conventional CE absorption or fluorescence signal, resulting from one-photon excitation, has a linear dependence on analyte concentration, and hence, the conventional CE peak follows a normal Gaussian profile, as shown in FIG. 4. At the same peak height, the wave-mixing CE peak is narrower than a conventional CE peak, and hence, compared to other laser-based or non-laser-based CE on-column detection methods, our wave-mixing detection method offers intrinsically enhanced separation resolution even when using identical CE separation conditions.

Figure 34:
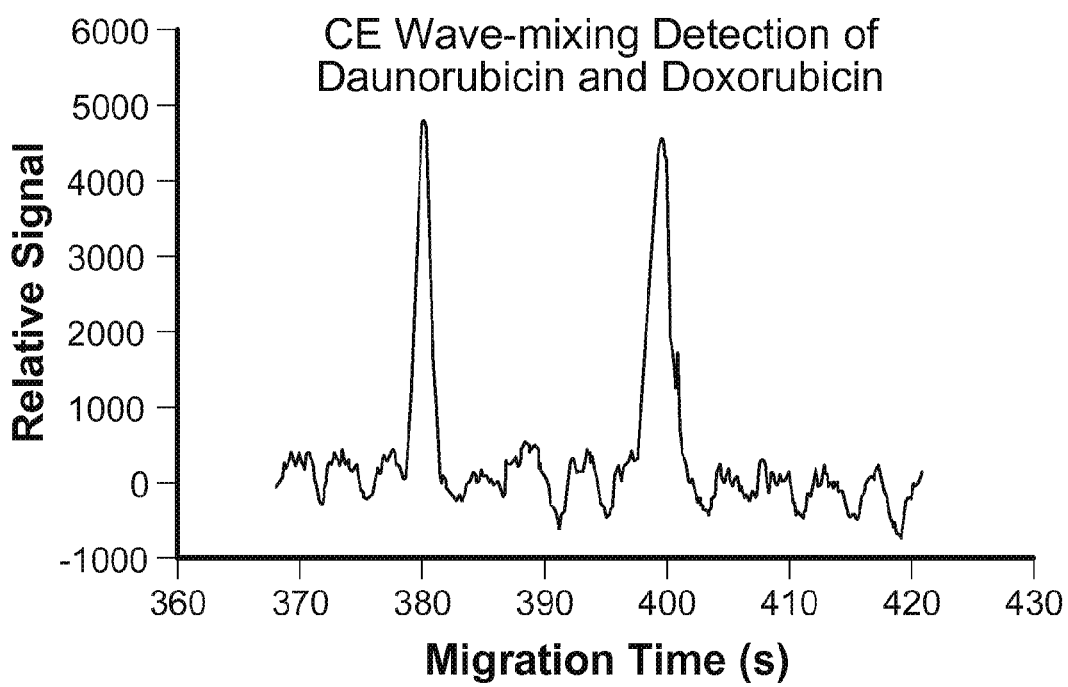
FIG. 34 shows an example of capillary electropherogram of a mixture of (a) $6.7 \times 10^{-8}$ M DAU and (b) $7.0 \times 10^{-8}$ M DOX separated in a 100 mM phosphate buffer/acetonitrile solvent binary mixture (30:70, v/v) at pH 4.2. Injection, 5 s at 12 kV; separation, 24 kV, 10.6 µA; capillary dimensions, 72 cm total length, 50 µm i.d., 45 cm effective length.

FIG. 34 shows an electropherogram of a mixture of 6.7× 10-8 M DAU and 7.0×10-8 M DOX using a phosphate buffer-ACN mixture (30:70, v/v). The amounts of DAU and DOX injected into the CE system are 0.60 femtomole and 0.63 femtomole, respectively, and the two drugs are well resolved.

Figure 35:
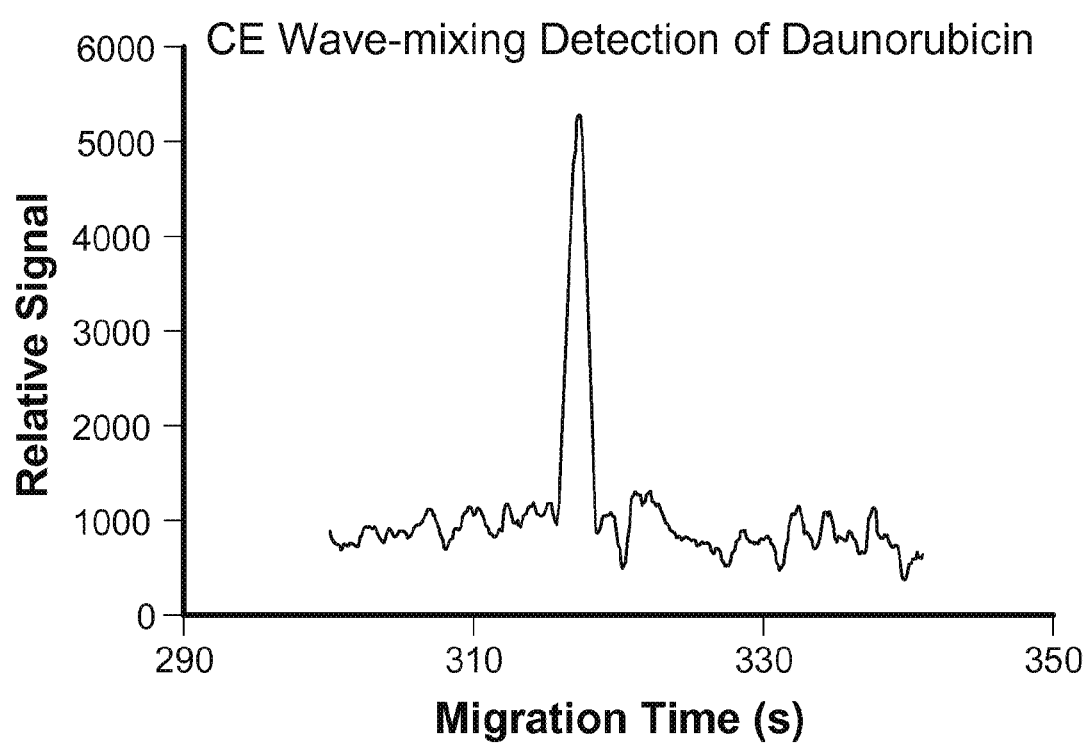
FIG. 35 shows an example of a capillary electropherogram of $3.9 \times 10^{-9}$ M DAU in a 100 mM phosphate buffer/acetonitrile solvent binary mixture (30:70, v/v) at pH 4.2. Injection, 5 s at 12 kV; separation, 30 kV, 13 µA; capillary dimensions, 75 cm total length, 50 µm i.d., 45 cm effective length.

FIG. 35 shows an electropherogram of DAU at a trace concentration level. The preliminary "injected" concentration detection limit for DAU is determined to be 9.9×10-10 M at S/N of 2, which corresponds to an injected mass detection limit of 9.1×10-18 mol. As illustrated in Table 2, our wave-mixing detection sensitivity level, especially the mass detection sensitivity, is comparable or better than those previously reported for laser-based absorbance or fluorescence determination of anthracyclines separated by high-performance liquid chromatography (HPLC) or CE.

TABLE 2

Comparison of laser-based detection methods for Anthracycline.

| Analytical Method | Injection Volume (μL) | Analyte | Molar Detection Limit (injected) (mol/L) | Mass Detection Limit (injected) (mole) | Ref. |
|---|---|---|---|---|---|
| HPLC-Fluorescence 474 nm | 1000 | DOX | $8.6 \times 10^{-10}$ | $8.6 \times 10^{-13}$ | 17 |
| HPLC-Fluorescence 480 nm | 400 | DOX | $8.6 \times 10^{-10}$ | $3.4 \times 10^{-13}$ | 18 |
| HPLC-Fluorescence 480 nm | 30 | DOX | $2.4 \times 10^{-10}$ | $7.2 \times 10^{-15}$ | 10 |
| HPLC-Absorbance 490 nm | 200 | DAU | $1.7 \times 10^{-8}$ | $3.5 \times 10^{-12}$ | 19 |
| CE-Fluorescence 476.5 nm | 0.014 | DAU | $8.9 \times 10^{-11}$ | $1.2 \times 10^{-18}$ | 16 |
| CE-Wave Mixing 476.5 nm | 0.0092 | DAU | $9.9 \times 10^{-10}$ | $9.1 \times 10^{-18}$ | This Work |

While this document contains many specifics, these should not be construed as limitations on the scope of any invention or of what may be claimed, but rather as descriptions of features that may be specific to particular embodiments of particular inventions. Certain features that are described in this document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, the separation of various system components in the embodiments described above should not be understood as requiring such separation in all embodiments.

Only a few implementations and examples are described and other implementations, enhancements and variations can be made based on what is described and illustrated in this document.

What is claimed is:

1. A method for using optical four wave mixing to detect cesium isotopes under ambient conditions, comprising:
    operating an atomizer under ambient conditions without a high vacuum chamber to vaporize an analyte solution containing a sample to be measured for presence of one or more cesium isotopes;
    operating a tunable diode laser to produce a laser beam tuned at a set of wavelengths within a laser frequency tuning range for interacting with the sample in the atomizer, wherein at least one wavelength in the set of wavelengths corresponds to a transition line at 11732.3 cm$^{-1}$ between 6s $^2S_{1/2}$ and 6p $^2P_{3/2}$ states of a cesium isotope instead of a stronger ground-state transition line of a cesium isotope;

using optical components arranged to split the laser beam from the tunable diode laser into a first pump beam, a second pump beam and a probe beam in a four wave mixing configuration and to direct the probe beam and the first and second pump beams to overlap with one another at a location in the vaporized analyte solution produced by the atomizer;

using an optical detector to receive light in a selected direction of a four wave mixing signal generated at the location in the vaporized analyte solution; and processing spectral components of a detector output of the optical detector corresponding to different wavelengths within the laser frequency tuning range to determine presence of one or more cesium isotopes in the sample based at least on a wavelength within the laser frequency tuning range corresponding to a non-ground-state transition line of a cesium isotope.

2. The method as in claim 1, comprising:
modulating one of the first and second pump beams at a modulation frequency; and
using a lock-in amplifier to process the detector output of the optical detector to extract the four wave mixing signal at different wavelengths within the laser frequency tuning range and to reject noise.

3. The method as in claim 1, wherein:
tuning the tunable diode laser to laser wavelengths for a cesium transition of 6s $^2S_{1/2} \to\, ^2P_{3/2}$ at 11,732.3 cm$^{-1}$ to obtain measurements of the spectral components of the detector output of the optical detector.

4. The method as in claim 1, wherein:
the optical components are arranged to split the laser beam from the tunable diode laser into the probe beam and the first and second pump beams in a configuration for backward scattering four wave mixing.

5. A device for using optical four wave mixing to detect cesium isotopes under ambient conditions, comprising:
an atomizer that vaporizes an analyte solution containing a sample to be measured for presence of one or more cesium isotopes under ambient conditions;
a tunable diode laser that produces a laser beam tuned at a set of wavelengths within a laser frequency tuning range for interacting with the sample in the atomizer, wherein at least one wavelength in the set of wavelengths corresponds to a transition line at 11732.3 cm$^{-1}$ between 6s $^2S_{1/2}$ and 6p $^2P_{3/2}$ states of a cesium isotope instead of a stronger ground-state transition line of a cesium isotope;
optical components arranged to split the laser beam from the tunable diode laser into a first pump beam, a second pump beam and a probe beam in a four wave mixing configuration and to direct the probe beam and the first and second pump beams to overlap with one another at a location in the vaporized analyte solution produced by the atomizer;
an optical detector that is positioned to receive light in a selected direction of a four wave mixing signal generated at the location in the vaporized analyte solution; and
a signal detection module that processes spectral components of a detector output of the optical detector corresponding to different wavelengths within the laser frequency tuning range to determine presence of one or more cesium isotopes in the sample based at least on a wavelength within the laser frequency tuning range corresponding to a non-ground-state transition line of a cesium isotope.

6. The device as in claim 5, wherein:
the atomizer is a graphite furnace atomizer.

7. The device as in claim 5, wherein:
the atomizer is an inductively coupled plasma atomizer.

8. The device as in claim 5, wherein:
the signal detection module includes a computer.

9. A method for using optical four wave mixing to detect circular dichroism of a sample material, comprising:
operating a capillary cell to provide an analyte solution containing a sample material to be measured for circular dichroism;
operating a pump laser to produce a pump laser beam at a pump laser wavelength;
using optical components arranged to split the pump laser beam into a first pump beam in a first pump linear polarization and a second pump beam in a second pump linear polarization orthogonal to the first pump linear polarization in a four wave mixing configuration to overlap with each another at a location in the analyte solution at the capillary cell;
operating a probe laser to produce a probe laser beam at a probe laser wavelength different from the pump laser wavelength;
directing the probe laser beam to the location in the analyte solution at the capillary cell in a direction for the four wave mixing configuration where the probe laser beam, the overlapped first and second pump beams and a four wave mixing signal beam at the probe laser wavelength interact to convert energy from the first and second pump beams into the four wave mixing signal beam;
modulating the first pump beam in the first pump linear polarization at a modulation frequency to be alternatively in a right circularly polarized light state and a left circularly polarized light state;
using an optical detector to receive light in a selected direction of the four wave mixing signal generated at the location in the analyte solution; and
processing a detector output of the optical detector corresponding to the modulation frequency to measure different optical absorptions associated with the alternatively right circularly polarized light state and left circularly polarized light state and to determine circular dichroism of the sample material.

10. The method as in claim 9, comprising:
coupling a microbore high performance liquid chromatography (HPLC) separation column to the capillary cell to separate different chemical components in the analyte solution to be present in the capillary cell.

11. The method as in claim 9, wherein:
the four wave mixing configuration is a forward scattering four wave mixing configuration.

12. A device for using optical four wave mixing to detect circular dichroism of a sample material, comprising:
a capillary cell to provide an analyte solution containing a sample material to be measured for circular dichroism;
a pump laser to produce a pump laser beam at a pump laser wavelength;
pump optical components arranged to split the pump laser beam into a first pump beam in a first pump linear polarization and a second pump beam in a second pump linear polarization orthogonal to the first pump linear polarization in a four wave mixing configuration to overlap with each another at a location in the analyte solution at the capillary cell;
a probe laser to produce a probe laser beam at a probe laser wavelength different from the pump laser wavelength;

one or more pump optical components that direct the probe laser beam to the location in the analyte solution at the capillary cell in a direction for the four wave mixing configuration where the probe laser beam, the overlapped first and second pump beams and a four wave mixing signal beam at the probe laser wavelength interact to convert energy from the first and second pump beams into the four wave mixing signal beam;

a polarization modulation unit that modulates the first pump beam in the first pump linear polarization at a modulation frequency to be alternatively in a right circularly polarized light state and a left circularly polarized light state;

an optical detector to receive light in a selected direction of the four wave mixing signal generated at the location in the analyte solution; and a signal processing module processing a detector output of the optical detector corresponding to the modulation frequency to measure different optical absorptions associated with the alternatively right circularly polarized light state and left circularly polarized light state and to determine circular dichroism of the sample material.

13. The device as in claim 12, comprising:

a microbore high performance liquid chromatography (HPLC) separation column coupled to the capillary cell to separate different chemical components in the analyte solution to be present in the capillary cell.

14. A method for using optical four wave mixing to detect circular dichroism of a sample material, comprising:

operating a capillary cell to provide an analyte solution containing a sample material to be measured for circular dichroism;

operating a pump laser to produce a pump laser beam at a pump laser wavelength;

using optical components arranged to split the pump laser beam into a first pump beam in a first pump linear polarization and a second pump beam in a second pump linear polarization orthogonal to the first pump linear polarization in a four wave mixing configuration to overlap with each another at a location in the analyte solution at the capillary cell;

operating a probe laser to produce a probe laser beam at a probe laser wavelength different from the pump laser wavelength;

directing the probe laser beam to the location in the analyte solution at the capillary cell in a direction for the four wave mixing configuration where the probe laser beam, the overlapped first and second pump beams and a four wave mixing signal beam at the probe laser wavelength interact to convert energy from the first and second pump beams into the four wave mixing signal beam;

modulating the first pump beam in the first pump linear polarization at a modulation frequency to be alternatively in the first pump linear polarization and in the second pump linear polarization;

using an optical detector to receive light in a selected direction of the four wave mixing signal generated at the location in the analyte solution; and processing a detector output of the optical detector corresponding to the modulation frequency to measure different optical absorptions associated with the alternatively the first pump linear polarization and the second pump linear polarization and to determine circular dichroism of the sample material.

\* \* \* \* \*